(12) United States Patent
Annoura et al.

(10) Patent No.: US 7,732,583 B2
(45) Date of Patent: Jun. 8, 2010

(54) GLYCOLIPIDS AND SYNTHETIC METHOD THEREOF AS WELL AS THEIR SYNTHETIC INTERMEDIATES, AND SYNTHETIC INTERMEDIATES, AND SYNTHETIC METHOD THEREOF

(75) Inventors: Hirokazu Annoura, Nagaokakyo (JP); Kenji Murata, Ibaraki (JP); Takashi Yamamura, Kokubunji (JP)

(73) Assignee: Japan as represented by President of National Center of Neurology and Psychiatry, Kodaira-shi, Tokyo (JP)

( * ) Notice: Subject to any disclaimer, the term of this patent is extended or adjusted under 35 U.S.C. 154(b) by 177 days.

(21) Appl. No.: 10/545,421

(22) PCT Filed: Feb. 13, 2004

(86) PCT No.: PCT/JP2004/001566

§ 371 (c)(1),
(2), (4) Date: Aug. 12, 2005

(87) PCT Pub. No.: WO2004/072091

PCT Pub. Date: Aug. 26, 2004

(65) Prior Publication Data

US 2006/0074235 A1    Apr. 6, 2006

(30) Foreign Application Priority Data

Feb. 14, 2003    (JP)    ............................. 2003-037397

(51) Int. Cl.
*C07G 3/00*    (2006.01)
*C07H 17/00*    (2006.01)
*C07H 17/02*    (2006.01)
*A61K 31/70*    (2006.01)
*A01N 43/04*    (2006.01)

(52) U.S. Cl. .................................................... 536/18.6
(58) Field of Classification Search ........................ None
See application file for complete search history.

(56) References Cited

U.S. PATENT DOCUMENTS 5,936,076 A * 8/1999 Higa et al. ................. 536/17.9

FOREIGN PATENT DOCUMENTS

| EP | 0 988 860 A1 | 3/2000 |
|---|---|---|
| WO | 93/05055 A1 | 3/1993 |
| WO | 94/09020 A1 | 4/1994 |
| WO | WO 98/16235 | 4/1998 |
| WO | 03/016326 A1 | 2/2003 |

OTHER PUBLICATIONS

Figueroa-Perez et al. Carbohydrate Research 328 (2000) 95-102.*
Wild et al. Liebigs Ann. 1995, 755-764.*
Schmidt et al. Carbohydrate Research vol. 174, Mar. 15, 1988, abstract.*
Kobayashi et al. Tetrahedron Letters, vol. 35, No. 51, pp. 9573-9576.*
Toshima et al. Chem. Rev. 1993, 93, 1503-1531.*
Miyamoto, K. et al., "A synthetic glycolipid prevents autoimmune encephalomyelitis by inducing $T_H 2$ bias of natural killer T cells", Nature, Oct. 4, 2001, vol. 413, No. 6855, pp. 531-534.
Ayad, T et al., "A new diorganiozinc-based enantio-selective access to truncated D-*ribo*-phytosphingosine", Tetrahedron Letters, Jan. 13, 2003, vol. 44, Issue 3, pp. 579-582.
Morita, M. et al., "Structure-Activity Relationship of α-Galactosylceramides against B16-Bearing Mice", Journal of Medicinal Chemistry, Jun. 9, 1995, vol. 38, No. 12, pp. 2176-2187.
Brossay, L. et al., "Cutting Edge: Structural Requirements for Galactosylceramide Recognition by CDI-Restricted NK T Cells", Journal of Immunology, Nov. 15, 1998, vol. 161, No. 10, pp. 5124-5128.
Chiu, H., et al., "A Facile Synthesis of Phyto-sphingosine from Diisopropylidepe-D-mannofuranose", Journal of Organic Chemistry, Jul. 11, 2003, vol. 68, No. 14, pp. 5788-5791.
Kawano, T. et al., "Natural killer-like non-specific tumor cell lysis medicated by specific ligand-activated Vα14 NKT cells", Proceedings of the Natural Academy of Sciences of the USA, May 12, 1998, vol. 95, No. 10, pp. 5690-5693.

(Continued)

*Primary Examiner*—Shaojia Anna Jiang
*Assistant Examiner*—Layla Bland
(74) *Attorney, Agent, or Firm*—Drinker Biddle & Reath LLP

(57) ABSTRACT

Novel glycolipid derivatives, where the substituent of the sphingosine base part is a short carbon chain alkyl group, substituted or unsubstituted cycloalkyl group, substituted or unsubstituted aryl group or substituted or unsubstituted aralkyl group and efficient synthetic methods for practical mass production of the same and intermediates useful for the synthesis of these compounds.

Glycolipids having the formula (I):

where $R^3$ indicates a substituted or unsubstituted $C_1$ to $C_7$ linear alkyl group, substituted or unsubstituted cycloalkyl group, substituted or unsubstituted aryl group, or substituted or unsubstituted aralkyl group and $R^8$ indicates a substituted or unsubstituted $C_1$ to $C_{35}$ alkyl group, substituted or unsubstituted aryl group or substituted or unsubstituted aralkyl group are chemically synthesized.

4 Claims, No Drawings

OTHER PUBLICATIONS

Kidd, P. PhD., Th1/Th2 Balance: The Hypothesis, its Limitations, and Implications for Health and Disease,: Alternative Medicine Review, vol. 8, No. 3, 2003, pp. 223-246.

Yamamura, Takashi, "Notoshinkei," vol. 53, 2001, pp. 707-713.

Murata et al., "Total Synthesis of an Immunosuppressive Glycolipid, (2S,3S,4R)-1-O- (α-D-Galactosyl)-2-tetracosanoylamino-1,3,4-nonanetroil", *J. Org. Chem.*, vol. 70, No. 6, 2005, pp. 2398-2401.

Miyake, S. "NKT Saibo to Jikkenteki Jikio Men'ekisei No Sekizuien", Inflammation & Immunology, Aug. 20, 2002, vol. 10, No. 5, pp. 501-506.

Miyake, S. "NKT Saibo Toshishitsu Ligand ni yoru Jiko Men'ekisei Shikkan Seigo", Annual Review Men'eki 2003, Dec. 5, 2002, pp. 71-77.

Costantino et al., "Immunomodulating Glycophingolipids: an Efficient Synthesis of a 2'-deoxy-α-galactosyl-GSL", *Tetrahedron, Elsevier Science Publishers*, Amsterdam, NL, vol. 58, No. 2, Jan. 7, 2002, pp. 369-375, XP004330613.

Akimoto et al., "Synthesis and Stereochemistry of Agelasphin-9b", *Tetrahedron Letters*, vol. 34, No. 35, 1993, pp. 5593-5596, XP002554487.

Schmidt et al., "Synthesis of $_{D\text{-}ribo}$-and $_{L\text{-}lyxo}$-Phytosphingosine: Transformation Into the Corresponding Lactosyl-Ceramides", *Carbohydrae Research, Elsevier Science Publishers B. V.*, Amsterdam, vol. 174, 1998, pp. 169-179, XP002554488.

Plettenburg et al., "Synthesis of α-Galactosyl Ceramide, A Potent Immunostimulatory Agent", *J. Org. Chem.*, vol. 67, No. 13, 2002, pp. 4559-4564, XP002554489.

\* cited by examiner

GLYCOLIPIDS AND SYNTHETIC METHOD THEREOF AS WELL AS THEIR SYNTHETIC INTERMEDIATES, AND SYNTHETIC INTERMEDIATES, AND SYNTHETIC METHOD THEREOF

TECHNICAL FIELD

The present invention relates to novel glycolipid derivatives and their synthetic methods as well as to their synthesis intermediates and their synthetic methods.

BACKGROUND ART

Autoimmune diseases, both for visceral organ or neuronal cells, are defined as "diseases where the destruction of one's own cells triggers the production of one's own antibodies against the destroyed cells or their ingredients and the destruction by one's own leucocytes is continued". Further, as typical autoimmune diseases, for example, multiple sclerosis, myasthenia gravis, chronic rheumatoid arthritis, systemic lupus erythematosus, Sjögren syndrome, systemic scleroderma, insulin-dependent diabetes, idiopathic thrombocytopenic purpura, Hashimoto's thyroiditis, Basedow's disease (Graves' disease), pernicious anemia, Addison's disease, atrophic gastritis, hemolytic anemia, ulcerative colitis, etc. are known.

For treatment of autoimmune diseases, steroid hormones, immunosuppressants, etc. are widely used, but at the time of use, sufficient cautions are required over side-effects. Safety and highly effective drug has not yet been found. On the other hand, regarding the cause of autoimmune diseases, the involvement of T-cells has been pointed out. This is believed to arise when the helper T-cell type 1 (Th1)/helper T-cell type 2 (Th2) immune balance is lost. For example, it has been reported that before the relapse of one of the autoimmune diseases, multiple sclerosis, the production of the Th1 type cytokines IFN-γ, IL-12, etc. is observed and that the administration of IFN-γ increases the frequency of relapse of multiple sclerosis. That is, in conditions of multiple sclerosis and other autoimmune diseases, the shift of the Th1/Th2 immune balance toward Th1 bias may be considered to play a central role (P. Kidd, *Altern. Med. Rev.* 2003, 8, 223: Takashi Yamamura, *Notoshinkei,* 2001, 53, 707). On the other hand, as Th2 type cytokines shifting the Th1/Th2 immune balance toward Th2 bias, IL-4, IL-5, IL-10 are known, but their administration of itself causes the appearance of systemic side-effects, and clinical application of itself is therefore believed to be substantially impossible.

NKT cells are lymphocytes which express both NK cell markers (i.e., NKT receptors) and T-cell antigen receptors (TCR). T-cells recognize peptides bonded to major histocompatibility complexes (MHC), while NKT cells recognize glycolipids bonded to the CD1d molecules and produce a large amount of cytokines in an extremely short period of time, when stimulated from TCR.

For example, the (2S,3S,4R)-1-O-(α-D-galactosyl)-2-(N-hexacosanoylamino)-1,3,4-octadecanetriol (α-GalCer) having the formula (XIV):

is the first substance reported, as a ligand presented by the monomorphic CD1d expressed on dendritic cells and activating the NKT cells expressing T-cell receptors having semi-invariant α-chains (Vα14). It has been shown that it has a powerful antitumor activity and immunization action (see T. Kawano et al., *Proc. Natl. Acad. Sci. USA.* 1998, 95, 5690). Recently, the novel glycolipid OCH discovered by Yamamura et al. is a derivative in which the carbon chain of the sphingosine base part of α-GalCer is shortened and a ligand which similarly bonds to CD1d to stimulate the NKT cells, but α-GalCer causes NKT cells to produce IFN-γ and IL-4, while OCH more selectively promotes the production of IL-4 and shifts the Th1/Th2 immune balance toward Th2 bias (see K. Miyamoto et al., *Nature* 2001, 413, 531). Further, OCH effected in oral administration in a mouse experimental autoimmunological encephalomyelitis (EAE) model, and therefore, so is expected to be a new medicine in the area of autoimmune diseases. For the synthetic method of glycolipids as represented by α-GalCer, the Wittig reaction, as the key step, is in general used for constracting the carbon chain of the sphingosine base part (see M. Morita et al., *J. Med. Chem.* 1995, 38, 2176). However, the glycolipid having the formula (I) is a derivative, in which the carbon chain of the sphingosine base of α-GalCer is shortened, and therefore, so similar synthetic procedures like with α-GalCer proved to give low yields. Further, the glycolipid having the formula (I) was originally obtained by purification using ion exchange resin or HPLC, then converting into freeze dried materials. However, by the above method, large-scale facilities are required at the time of large-scale synthesis, and therefore, not only is there a problem of synthetic costs, there is also the major problem that the quality of the products may not be stable. Therefore, an efficient synthetic method for the large-scale production of the compounds having the formula (I) has not been known yet. Further, the synthesis of a glycolipid, where the substituent of the sphingosine base part is a substituted or unsubstituted cycloalkyl group, substituted or unsubstituted aryl group, or substituted or unsubstituted aralkyl group has not yet been reported.

DISCLOSURE OF THE INVENTION

Under the above background, the objectives of the present invention are to provide novel glycolipids having an immunosuppressive action useful for the treatment of autoimmune diseases and efficient synthetic methods for economically mass producing the same.

Another objective of the present invention is to provide glycolipids in good quality improved in physical properties. A further objective of the present invention is to provide the synthetic intermediates useful for the preparation of these compounds and their synthetic method.

The inventors succeeded in the efficient synthesis of glycolipids having formula (I):

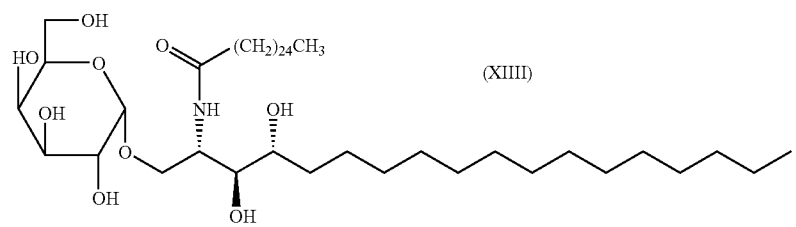

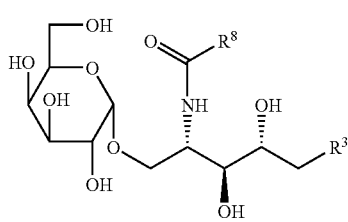
(I)

wherein $R^3$ indicates a substituted or unsubstituted $C_1$ to $C_7$ linear alkyl group, substituted or unsubstituted cycloalkyl group, substituted or unsubstituted aryl group, or substituted or unsubstituted aralkyl group, $R^8$ indicates a substituted or unsubstituted $C_1$ to $C_{35}$ alkyl group, substituted or unsubstituted aryl group, or substituted or unsubstituted aralkyl group, where the substituent of the Sphingosine base part is a substituted or unsubstituted short carbon chain type linear alkyl group, substituted or unsubstituted cycloalkyl group, substituted or unsubstituted aryl group, or substituted or unsubstituted aralkyl group and further found that hydrates of the glycolipids having the formula (I) give stable crystals improved in physical properties, whereby the objective of the present invention was achieved.

That is, the present invention, there is provided a synthetic method of a glycolipid derivative comprising:

reacting a compound having the formula (II):

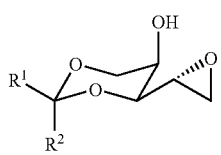
(II)

wherein $R^1$ and $R^2$ independently indicate a hydrogen atom, substituted or unsubstituted alkyl group, substituted or unsubstituted aryl group, or substituted or unsubstituted aralkyl group, or $R^1$ and $R^2$ bond together to indicate a propylene group, butylene group, pentylene group, or hexylene group, whereby a cyclic system is formed. with any one of the alkyl metal reagents of formula (IIIa), (IIIb), (IIIc), and (IIId):

(R³)₂CuM,     (IIIa)

R³M/CuX,     (IIIb)

R³M/BF₃,     (IIIc)

R³M     (IIId)

where $R^3$ indicates a substituted or unsubstituted $C_1$ to $C_7$ linear alkyl group, substituted or unsubstituted cycloalkyl group, substituted or unsubstituted aryl group, or substituted or unsubstituted aralkyl group, M indicates Li, MgCl, MgBr or MgI and X indicates a chlorine atom, bromine atom, iodine atom or fluorine atom to obtain a compound having the formula (IV):

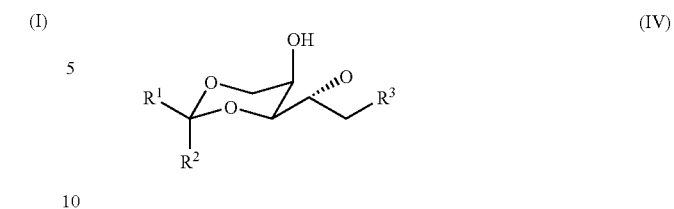
(IV)

wherein $R^1$, $R^2$ and $R^3$ are as the same defined above, reacting the compound having the formula (IV) with an alkylsulfonyl halide, arylsulfonyl halide, aralkylsulfonyl halide, alkylsulfonic acid anhydride, arylsulfonic acid anhydride, or aralkylsulfonic acid anhydride to obtain a compound having the formula (V):

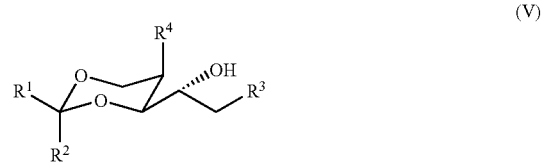
(V)

where $R^1$, $R^2$ and $R^3$ are the same as defined above and $R^4$ indicates an alkylsulfonyloxy group, arylsulfonyloxy group, or aralkylsulfonyloxy group), reacting the compound having the formula (V) with an azidation agent to obtain a compound having the formula (VIa):

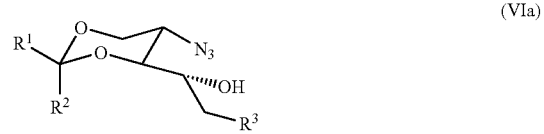
(VIa)

where $R^1$, $R^2$ and $R^3$ are the same as defined above, removing the protective acetal group of the compound having the formula (VIa) or removing the protective acetal group of the compound having the formula (V) to obtain a compound of the formula (VIb):

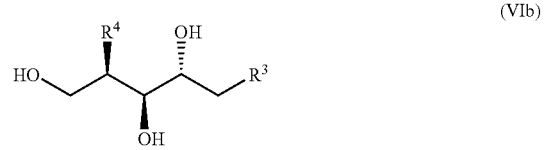
(VIb)

where $R^3$ and $R^4$ are the same as defined above, reacting with the compound having the formula (VIb) with an azidation agent to obtain a compound having the formula (VII):

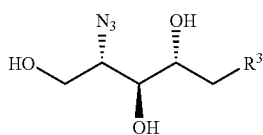

where R³ is the same as defined above, again acetalizing the compound having the formula (VII) to obtain a compound having the formula (VIIIa):

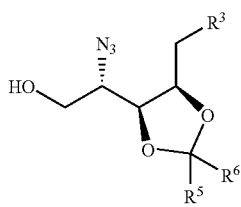

where R³ is the same as defined above, R⁵ and R⁶ independently indicate a hydrogen atom, substituted or unsubstituted alkyl group, substituted or unsubstituted aryl group, or substituted or unsubstituted aralkyl group or R⁵ and R⁶ bond together to indicate a propylene group, butylene group or pentylene group, whereby a cyclic structure is formed, or protecting the two secondary hydroxy groups of the compound having the formula (VII) to obtain a compound having the formula (VIIIb):

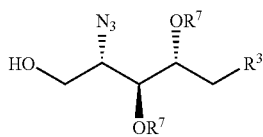

where R³ is the same as defined above R⁷ indicates a benzyl group, p-methoxybenzyl group, 3,4-dimethoxybenzyl group, p-nitrobenzyl group, diphenylmethyl group or di(p-nitrophenyl)methyl group, reacting the compound having the above formula (VIIIa) or (VIIIb) with a compound having the formula (IX):

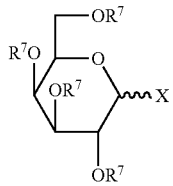

where R⁷ and X are the same as defined above to obtain a compound having the formula (Xa) or (Xb):

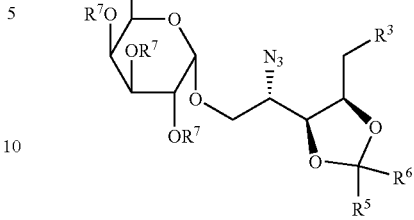

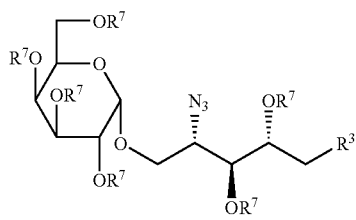

where R³, R⁵, R⁶ and R⁷ are the same as defined above, reducing the azide group of the compound having the formula (Xa) or (Xb) to an amino group to obtain a compound having the formula (XIa) or (XIb):

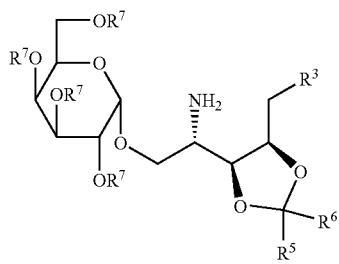

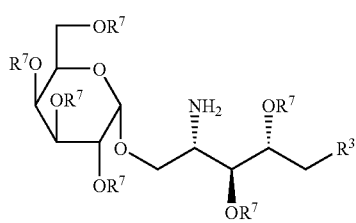

where R³, R⁵, R⁶ and R⁷ are the same as defined above, acylating the amino group of the compound having the formula (XIa) or (XIb) to obtain a compound having the formula (XIIa) or (XIIb):

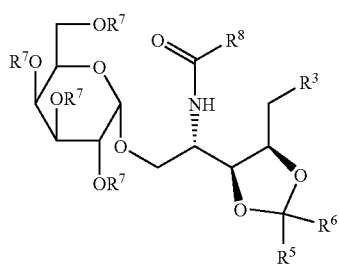

-continued

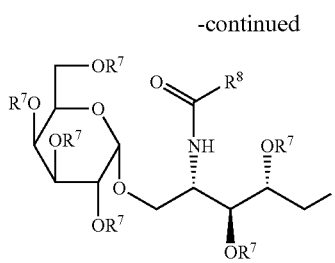
(XIIb)

where $R^3$, $R^5$, $R^6$ and $R^7$ are the same as defined above $R^8$ indicates a substituted or unsubstituted $C_1$ to $C_{35}$ alkyl group, substituted or unsubstituted aryl group, or substituted or unsubstituted aralkyl group), removing the protective acetal of the compound having the formula (XIIa) to obtain the compound of the formula (XIII):

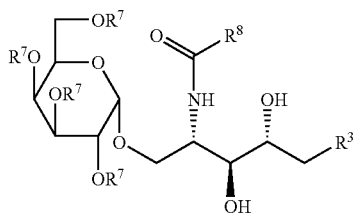
(XIII)

where $R^3$, $R^7$ and $R^8$ are the same as defined above, and removing the remaining protective groups of the compound having the above formula (XIIb) or (XIII) to obtain a compound having the formula (I):

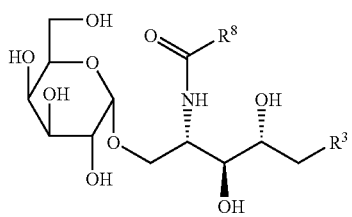
(I)

where $R^3$ and $R^8$ are the same as defined above.

In accordance with the present invention, further compounds having the above formula (VII), formula (VIIIa), formula (VIIIb), formula (Xa) or (Xb), formula (XIa) or (XIb), formula (XIIa) or (XIIb), and formula (XIII) are provided.

In accordance with the present invention, there is further provided a novel glycolipid having the above formula (I) where $R^3$ indicates a substituted or unsubstituted cycloalkyl group, substituted or unsubstituted aryl group, or substituted or unsubstituted aralkyl group, and $R^8$ indicates —$(CH_2)m$-$CH_3$, where m indicates an integer of 10 to 25, a $C_6$ to $C_{35}$ aryl group unsubstituted or substituted with an alkyl group, alkoxy group, or amide group, or a $C_7$ to $C_{35}$ aralkyl group unsubstituted or substituted with an alkyl group, alkoxy group, or amide group.

In accordance with the present invention, there is still further provided a drug for the treatment of diseases where the Th1/Th2 immune balance is shifted toward Th1 bias or diseases where the Th1 cells cause symptoms to worsen or a Th2 type cytokine producing derivative having as an active ingredient a glycolipid of the above formula (I) wherein $R^3$ indicates —$(CH_2)n$-$CH_3$, where n indicates an integer of 0 and 4 to 6, substituted or unsubstituted cycloalkyl group, substituted or unsubstituted aryl group, or substituted or unsubstituted aralkyl group, $R^8$ indicates —$(CH_2)m$-$CH_3$, where m indicates an integer of 10 to 25, $C_6$ to $C_{35}$ aryl group substitutable with an alkyl group, alkoxy group, or amide group, or a $C_7$ to $C_{35}$ arakyl group substitutable with an alkyl group, alkoxy group or amide group. The "Th2 type cytokine" is IL-4, IL-5, IL-10, or another cytokine, by which the Th1/Th2 immune balance is shifted toward Th2 bias.

BEST MODE FOR CARRYING OUT THE INVENTION

A glycolipid having the formula (I), according to the present invention, may be synthesized by the methods explained below. These methods will be successively explained.

First, the starting substance (II), as shown by the reaction formulae below, is obtained by obtaining, from a known starting substance (XV), the compound (XVI), then converting this to the compound (XVII) to obtain the compound (II) (Step 1). This compound (II) is reacted with an organometallic reagent (IIIa), (IIIb), (IIIc) or (IIId) to obtain the compound (IV) (Step 2), which is then converted through the compound (V) to the compound (VIa) or (VIb) (Step 3). From these compounds (VIab), the compound (VII) is obtained, then is converted to the compound (VIIIa) or (VIIIb) (Step 4). Next, this compound (VIIIa) or (VIIIb) is reacted with the compound (IX) to obtain the compound (Xa) or (Xb) (Step 5), compound (XIa) or (XIb) is obtained from the compound (Xa) or (Xb), then converted to the compound (XIIa) or (XIIb) (Step 6), then the compound (XIIa) is used to derive the compound (XIII). This or the compound (XIIb) obtained at Step 6 is used to obtain the target compound (I) (Step 7). These Step 1 to Step 7 will now be explained in detail.

Step 1

It is possible to synthesize the compound having the formula (II) from the known starting material D-arabitol (XV).

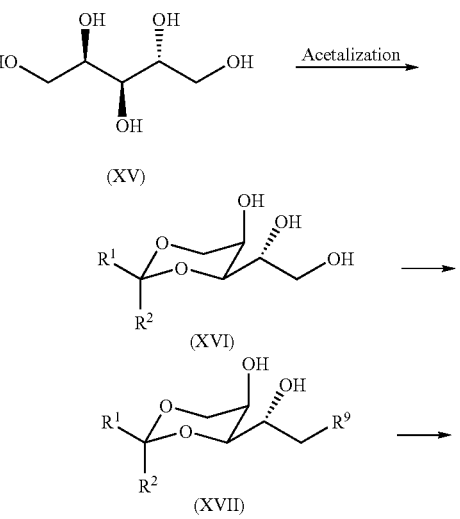

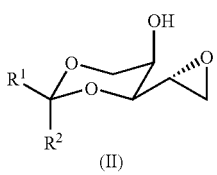

wherein $R^1$ and $R^2$ independently indicate a hydrogen atom, substituted or unsubstituted alkyl group, substituted or unsubstituted aryl group, or substituted or unsubstituted aralkyl group or $R^1$ and $R^2$ bond together to indicate a propylene group, butylene group, pentylene group or hexylene group, whereby a cyclic structure is formed and $R^9$ indicates an alkylsulfonyloxy group, arylsulfonyloxy group or aralkylsulfonyloxy group. Here, as a preferable alkyl group, a $C_1$ to $C_4$ alkyl group, halogen-substituted methyl group, or other $C_1$ to $C_4$ alkyl group (as a preferable, halogen, a fluorine atom or chlorine atom) may be mentioned. As a preferable substituent of the alkyl group, in addition to a halogen atom, a methoxy group, ethoxy group, nitro group, etc. may be mentioned. As a preferable aryl group, a $C_6$ to $C_{12}$ aryl group, specifically a phenyl group, p-tolyl group, m-tolyl group, o-tolyl group, 4-tert-butylphenyl group, 4-phenylphenyl group, 4-isopropylphenyl group, etc. may be mentioned. These may be substituted with a fluorine atom, chlorine atom, bromine atom, methoxy group, nitro group, cyano group, trifluoromethyl group or other group. Specifically, a 4-methoxyphenyl group, 4-chlorophenyl group, 2,5-dichlorophenyl group, 4-fluorophenyl group, 4-bromophenyl group, 4-nitrophenyl group, 3-nitrophenyl group, 2-nitrophenyl group, 4-cyano group, 4-trifluoromethyl group, etc. may be mentioned.

In the above reaction, the D-arabitol having the formula (XV) enables the production of the compound of formula (XVI) using an acetalization reaction. For the synthesis of the compound (XVI), it is possible to use the various methods described in *Compendium of Organic Synthetic Methods* (Wiley-Interscience; A Division of John Wiely & Sons) etc. If giving one example, it is possible to use the method of reacting the compound (XV) in benzene, toluene, dioxane, chloroform, or another solvent not participating in the reaction at, for example, −20° C. to 100° C., preferably 0 to 80° C., in the presence of 1 to 30 equivalent weights of acetic acid, trifluoroacetic acid, methanesulfonic acid, trifluoromethanesulfonic acid, or another organic acid or hydrochloric acid, sulfuric acid, nitric acid, or another inorganic acid with acetoaldehyde, propionaldehyde, butylaldehyde, pentanal, cyclopentanone, cyclohexanone, phenylacetoaldehyde, benzaldehyde, p-tolualdehyde, 4-fluorobenzaldehyde, 2-naphthylaldehyde, etc.

The compound (XVI) obtained by the above method may be directly used, as a material for producing the compound (XVII), but may also be used, if necessary, after purification by a general purification method, for example, recrystallization or column chromatography.

Then, by reacting the compound (XVI) in methylene chloride, 1,2-dichloroethane, chloroform, carbon tetrachloride, acetonitrile, diethylether, tetrahydrofuran, dioxane, benzene, toluene, xylene, ethyl acetate or another inert solvent in the presence of triethylamine, diisopropylethylamine, pyridine, sodium carbonate, sodium hydrogen carbonate, potassium carbonate, potassium hydrogen carbonate or another base at, for example, −20° C. to 100° C., preferably −10° C. to 80° C., with 1 to 5 equivalent weights of methanesulfonyl chloride, methanesulfonic acid anhydride, ethane sulfonyl chloride, 1-propanesulfonyl chloride, 1-butanesulfonyl chloride, trifluoromethanesulfonyl chloride, α-toluene sulfonyl chloride, benzene sulfonyl chloride, p-toluene sulfonyl chloride, m-toluene sulfonyl chloride, o-toluene sulfonyl chloride, p-toluene sulfonic acid anhydride, 4-methoxybenzene sulfonyl chloride, 4-chlorobenzene sulfonyl chloride, 2,5-dichlorobenzene sulfonyl chloride, 4-bromobenzene sulfonyl chloride, 4-fluorobenzene sulfonyl chloride, 2-nitrobenzene sulfonyl fluoride, 3-nitrobenzene sulfonyl chloride, 4-nitrobenzene sulfonyl chloride, 4-tert-butylbenzene sulfonyl chloride, 2-nitro-α-toluene sulfonyl chloride, α-toluene sulfonyl fluoride, or another sulfonylation agent for 1 to 72 hours, the compound (XVII) can be obtained. At this time, surprisingly, it was learned that, by adding a catalytic amount (for example, 0.01 to 2 moles, based upon 1 mol of the compound (XVI)) of di-n-butyl tin oxide, the primary hydroxy groups having the compound (XVI) are selectively sulfonylated and the reaction proceeds in a short time.

The compound (XVII) obtained by the above method may be directly used, as a material for producing the compound (II), but may also be used, if necessary, after purification by a general purification method, for example, recrystallization or column chromatography.

The compound (XVII) may be treated in tetrahydrofuran, dioxane, ethyleneglycol dimethylether, benzene, toluene, xylene, dimethylformamide, dimethylsulfoxide or another inert solvent at, for example, −20° C. to 120° C., preferably −10° C. to 80° C., by sodium, potassium, sodium hydride, potassium hydride, sodium methoxide, sodium ethylate, potassium tert-butoxide or another base, so as to obtain the compound (II).

The compound (II) obtained by this step may be directly used, as a material for the next step, but may also be used, if necessary, after purification by a general purification method such as recrystallization or column chromatography.

Step 2

The compound of formula (II) obtained at Step 1 may be reacted with an organometallic reagent having the formula (IIIa), (IIIb), (IIIc), or (IIId) to obtain the compound having the formula (IV).

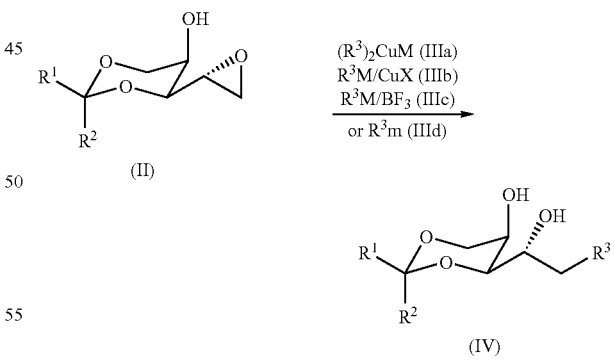

where $R^1$ and $R^2$ are the same as defined above, $R^3$ indicates a substituted or unsubstituted $C_1$ to $C_7$ linear alkyl group (as a preferable substituent, a methyl group, ethyl group, propyl group, butyl group, pentyl group, hexyl group, heptyl group, cyclopentyl group, cyclohexyl group, isobutyl group, cycloheptyl group, isopentyl group, isohexyl group, etc. may be mentioned), substituted or unsubstituted preferably $C_3$ to $C_8$ cycloalkyl group, for example, a cyclopropyl group, cyclobutyl group, cyclopentyl group, cyclohexyl group or cycloheptyl group (as a preferable substituent, a methyl group, ethyl group, propyl group, butyl group, methoxy group, chlorine atom, fluorine atom, trifluoromethyl group, etc. may be mentioned), substituted or unsubstituted preferably $C_6$ to $C_{18}$ aryl group, for example, a phenyl group, pyridyl group, or naphthyl group (as a preferable substituent, a methyl group, ethyl group, methoxy group, fluorine atom, chlorine atom, phenyl group, 2-fluorophenyl group, phenoxy group, phenylmethyl group, cyclopentyl group, cyclopentyloxy group, trifluoromethyl group, acylamino group, cyano group, cycloheptyl group, cycloheptyloxy group, etc. may be mentioned), substituted or unsubstituted preferably $C_7$ to $C_{18}$ aralkyl group, for example, a phenylmethyl group, phenylethyl group, pyridylmethyl group, or naphthylmethyl group (as a preferable substituent, a fluorine atom, chlorine atom, methyl group, ethyl group, methoxy group, trifluoromethyl group, cyclopentyl group, cyclopentyloxy group, etc. may be mentioned), M indicates a Li, MgCl, MgBr, MgI and X indicates a chlorine atom, bromine atom, iodine atom or fluorine atom.

That is, 1 to 6 equivalent weights of alkyl lithium reagent or Grignard reagent is added to the compound (II) in the presence or absence of copper (I) iodide, copper (I) bromide, copper (I) chloride, or borofluoride in diethyl ether, tetrahydrofuran, dioxane, toluene, xylene, hexane, cyclohexane, or another inert solvent or their mixed solvents, at, for example, −78° C. to 0° C., preferably −50° C. to −10° C. and the result stirred at that temperature for 1 to 5 hours. By adding the compound (II) into this and further stirring for 1 to 5 hours, the target compound (IV) can be obtained.

The compound (IV) obtained by this step may be directly used, as a material for production of the compound (V), but may also be used, if necessary, after purification by a general purification method such as recrystallization or column chromatography.

Step 3

The compound having the formula (IV) obtained at Step 2 may be converted to the compound (V), then subjected to an azidation reaction so as to obtain the compound having the formula (VIa).

Further, the compound (V) may be deacetalized to obtain the compound having the formula (VIb).

where $R^1$, $R^2$ and $R^3$ are the same as defined above and $R^4$ indicates an alkylsulfonyloxy group, arylsulfonyloxy group or aralkylsulfonyloxy group.

By reacting the compound (IV) under non-solvent conditions or in methylene chloride, 1,2-dichloroethane, chloroform, carbon tetrachloride, acetonitrile, diethylether, tetrahydrofuran, dioxane, benzene, toluene, xylene, ethyl acetate or another inert solvent at, for example, −20° C. to 100° C., preferably −10° C. to 80° C., in the presence of triethylamine, diisopropylethylamine, pyridine, sodium carbonate, sodium hydrogen carbonate, potassium carbonate, potassium hydrogen carbonate, or another base with 1 to 5 equivalent weights of methanesulfonyl chloride, methanesulfonic acid anhydride, ethane sulfonyl chloride, 1-propanesulfonyl chloride, 1-butanesulfonyl chloride, trifluoromethanesulfonyl chloride, α-toluene sulfonyl chloride, benzene sulfonyl chloride, p-toluene sulfonyl chloride, p-toluene sulfonic acid anhydride, 4-methoxybenzene sulfonyl chloride, 4-chlorobenzene sulfonyl chloride, 2-nitrobenzene sulfonyl chloride, 3-nitrobenzene sulfonyl chloride, 4-nitrobenzene sulfonyl chloride, 2-nitro-α-toluene sulfonyl chloride, α-toluene sulfonyl fluoride or another sulfonylization agent, for example, for 1 to 72 hours, compound (V) can be obtained.

The compound (IV) obtained by this step may be directly used, as a material for production of the compound (V), but may also be used, if necessary, after purification by a general purification method such as recrystallization or column chromatography.

Then, by reacting the compound (V) with 1 to 50 equivalent weights of sodium azide or lithium azide in acetonitrile, diethylether, tetrahydrofuran, dioxane, benzene, toluene, xylene, dimethylsulfoxide, dimethylformamide or another inert solvent at, for example, 0 to 200° C., preferably 20 to 120° C., the compound (V) can be converted to the compound (VIa). At this time, in this reaction, if necessary, triethylamine, diisopropylethylamine, pyridine, sodium carbonate, sodium hydrogen carbonate, potassium carbonate, potassium hydrogen carbonate or another base may be added.

Further, the compound (V) may be deacetalized by an ordinary method to obtain the compound (VIb). For the conditions of the deacetalization, it is possible to use the many methods described in *Protective Groups In Organic Synthesis* (John Wiley & Sons) etc. For example, the compound (V) may be stirred in a mixture of hydrochloric acid, sulfuric acid, nitric acid, acetic acid, trifluoroacetic acid, methanesulfonic

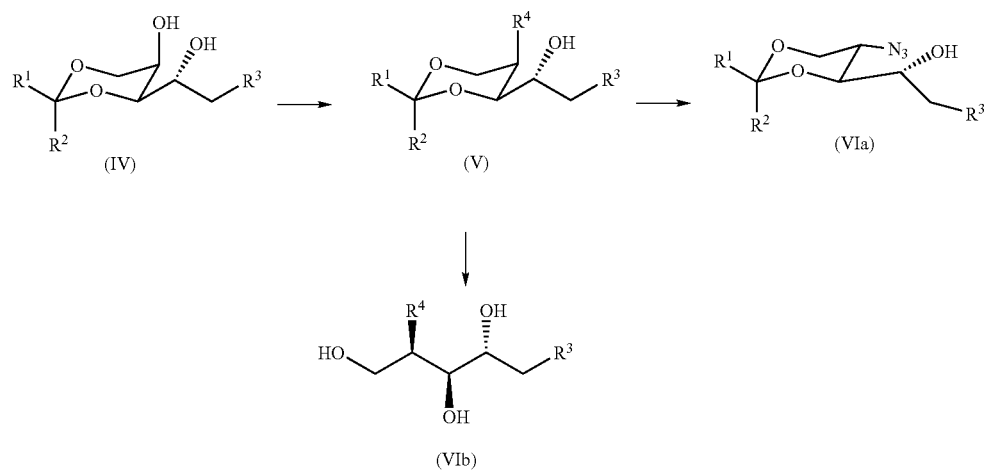

acid, trifluoromethanesulfonic acid or another inorganic acid or another organic acid and methanol, ethanol, 2-propanol, dioxane, methylene chloride, 1,2-dichloroethane, chloroform, carbon tetrachloride, benzene, toluene, xylene or another inert solvent at −20 to 100° C., preferably 0 to 50° C. to obtain the compound (VIb). Further, when, in the compound (V), the substituent of one or both of $R^1$ and $R^2$ expresses a substitutable aryl group, it is possible to heat and reflux this in methanol, ethanol, 2-propanol, ethyl acetate, tetrahydrofuran, dimethylformamide or another solvent not participating in the reaction in the presence of Pd—C, $Pd(OH)_2$, $PtO_2$, etc. with the addition of 4-methylcyclohexene or hydrogenate this at room temperature to obtain the compound (VIb).

Step 4

The compound of formula (VIa) obtained at Step 3 may be deacetalized or the compound of formula (VIb) may be subjected to an azidation reaction to obtain the compound (VII) which may then be again acetalized to obtain the compound of the formula (VIIIa). Further, the primary hydroxy groups of the compound (VII) may be selectively tritylated, then the remaining hydroxy groups are converted to an arylmethylether derivative and detritylated to obtain the compound (VIIIb).

First, the compound (VIa) is deacetalized by an ordinary method to obtain the compound (VII). For the conditions for the deacetalization, it is possible to use the many methods described in *Protective Groups In Organic Synthesis* (John Wiley & Sons) etc. For example, the compound (VI) may be stirred in a mixture of hydrochloric acid, sulfuric acid, nitric acid, acetic acid, trifluoroacetic acid, methanesulfonic acid, trifluoromethanesulfonic acid or another inorganic acid or organic acid and methanol, ethanol, 2-propanol, dioxane, methylene chloride, 1,2-dichloroethane, chloroform, carbon tetrachloride, benzene, toluene, xylene or another inert solvent at, for example, −10° C. to 100° C., preferably 0 to 50° C. to obtain the compound (VII).

Further, the compound (VIb) may be subjected to an azidation reaction similar to the conversion of the compound (V) to the compound (VIa) of Step 3 to obtain a compound having the formula (VII). That is, the compound (VIb) may be reacted in acetonitrile, diethylether, tetrahydrofuran, dioxane, benzene, toluene, xylene, dimethylsulfoxide, dimethylformamide or another inert solvent with 1 to 50 equivalent weights of sodium azide or lithium azide at 0 to 200° C., preferably 20 to 120° C. to obtain the compound (VII). At this time, in the reaction, if necessary, triethylamine, diisopropylethylamine, pyridine, sodium carbonate, sodium hydrogen

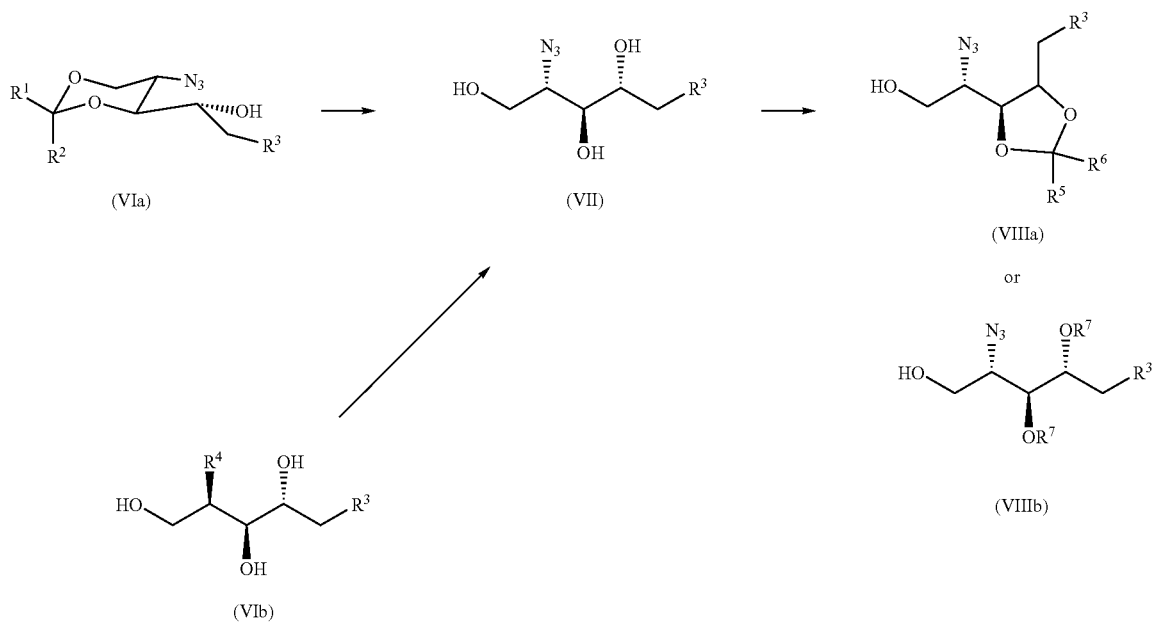

where $R^1$, $R^2$ and $R^3$ are the same as defined above, $R^5$ and $R^6$ independently indicate a hydrogen atom, substituted or unsubstituted preferably $C_1$ to $C_5$ alkyl group (as a preferable substituent, a fluorine atom, methoxy group, etc. may be mentioned), substituted or unsubstituted $C_6$ to $C_{12}$ aryl group (for example, a phenyl group, p-tolyl group, m-tolyl group, or naphthyl group), substituted or unsubstituted preferably $C_7$ to $C_{12}$ aralkyl group (as a preferable substituent, a methyl group, ethyl group, fluorine atom, methoxy group, etc. may be mentioned) or $R^5$ and $R^6$ bond together to indicate a propylene group, butylene group or pentylene group, whereby a cyclic structure is formed, and $R^7$ indicates a benzyl group, p-methoxybenzyl group, 3,4-dimethoxybenzyl group, p-nitrobenzyl group, diphenylmethyl group or di(p-nitrophenyl)methyl group.

carbonate, potassium carbonate, potassium hydrogen carbonate, or another base may also be added.

The compound (VII) obtained by this reaction may be directly used, as a material for production of the compound (VIIIa) or (VIIIb), but may also be used, if necessary, after purification by a general purification method such as recrystallization or column chromatography.

Then, the compound (VII) may be subjected to an acetalization reaction to obtain the compound (VIIIa). For the conditions for the acetalization, the many methods described in *Protective Groups In Organic Synthesis* (John Wiley & Sons) etc. may be used. That is, the compound (VII) may be reacted with an acetalization agent in the presence of an organic acid or inorganic acid under non-solvent conditions or in diethylether, dioxane, benzene, toluene, xylene or another inert solvent at, for example, 0 to 200° C., preferably 20 to 120° C. to obtain the compound (VIIIa). At this time, as the acetalization reagent, acetone, 2,2-dimethoxypropane, 2-methoxypropene, 2-ethoxypropene, benzaldehyde, benzaldehyde dimethyl acetal, cyclohexanone, cyclohexanone dimethyl acetal, cyclopentanone, cyclopentanone dimethyl acetal, etc. may be used.

Further, the primary hydroxy groups of the compound (VII) may be tritylized, then the other secondary hydroxy groups arylmethylated, then detritylized to obtain the compound (VIIIb). As the conditions for the tritylization, for example, 0.8 to 2 equivalent weights of trityl bromide or trityl chloride may be reacted in diethylether, tetrahydrofuran, dioxane, benzene, toluene, xylene, dimethylformamide, dimethylsulfoxide or another inert solvent in the presence of lithium carbonate, potassium carbonate, sodium carbonate, sodium hydrogen carbonate, potassium hydrogen carbonate, lithium hydroxide, sodium hydroxide, potassium hydroxide, sodium hydride, potassium hydride, sodium, potassium, triethylamine, diisopropylethylamine, pyridine, Lutidine or another base at, for example, −50° C. to 120° C., preferably −20° C. to 80° C. as a condition. Further, as the arylmethylation agent, benzyl chloride, benzyl bromide, p-methoxybenzyl chloride, m-methoxybenzyl chloride, p-nitrobenzyl chloride, p-nitrobenzyl bromide, etc. may be mentioned, while as the reaction condition of the arylmethylation, the conditions of the above tritylization may be used. Further, for the conditions of the detritylization, it is possible to use the many methods described in *Protective Groups In Organic Synthesis* (John Wiley & Sons) etc. For example, reaction under non-solvent conditions or in methylene chloride, chloroform, 1,2-dichloroethane, benzene, toluene, xylene, dioxane, water, methanol, ethanol, 2-propanol, tert-butanol or another solvent in the presence of formic acid, acetic acid, trifluoroacetic acid, hydrochloric acid, sulfuric acid, nitric acid or another acid or cupric sulfate at, for example, −50° C. to 150° C., preferably −20° C. to 100° C. may be mentioned.

The compound (VIIIa) or (VIIIb) obtained by the above reaction may be directly used, as a material for producing the compound (Xa) or (Xb), but may also be used, if necessary, after purification by a general purification method, for example, recrystallization or column chromatography.

Step 5

The compound having the formula (VIIIa) or (VIIIb) obtained at Step 4 may be subjected to a glycosidation reaction with the compound (IX) to obtain the compound (Xa) or (Xb).

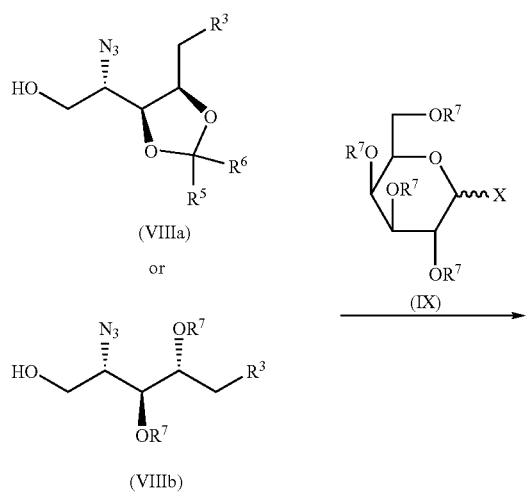

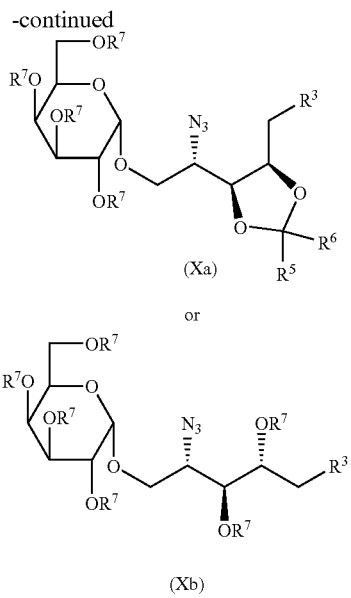

where $R^3$, $R^5$, $R^6$, $R^7$ and X are the same as defined above.

That is, the compound (VIIIa) or (VIIIb) may be reacted with the compound (IX) in hexane, cyclohexane, methylene chloride, chloroform, 1,2-dichloroethane, ether, tetrahydrofuran, acetonitrile, benzene, toluene, xylene, dioxane, dimethylformamide or another inert solvent or their mixtures in the presence of boron trifluoride, silver perchlorate, tin (II) chloride, titanium tetrachloride, tin tetrachloride or another Lewis acid or tetra-n-butylammonium bromide or another halogenated ammonium salt at, for example, −100° C. to 50° C., preferably −78° C. to 30° C. to obtain the compound (Xa) or (Xb). The Lewis acid or halogenated ammonium salt used for this reaction may be used alone or in combinations with different types. Further, at that time, if necessary, a molecular sieve may also be added.

The compound (Xa) or (Xb) obtained by the above reaction may be directly used, as a material for the next step, but may also be used, if necessary, after purification by a general purification method, for example, recrystallization or column chromatography.

Step 6

The azide group of the compound having the formula (Xa) or (Xb) obtained at Step 5 may be reduced to an amino group to obtain the compound (XIa) or (XIb), then the compound subjected to an amidation reaction with a carboxylic acid derivative to obtain the compound (XIIa) or (XIIb).

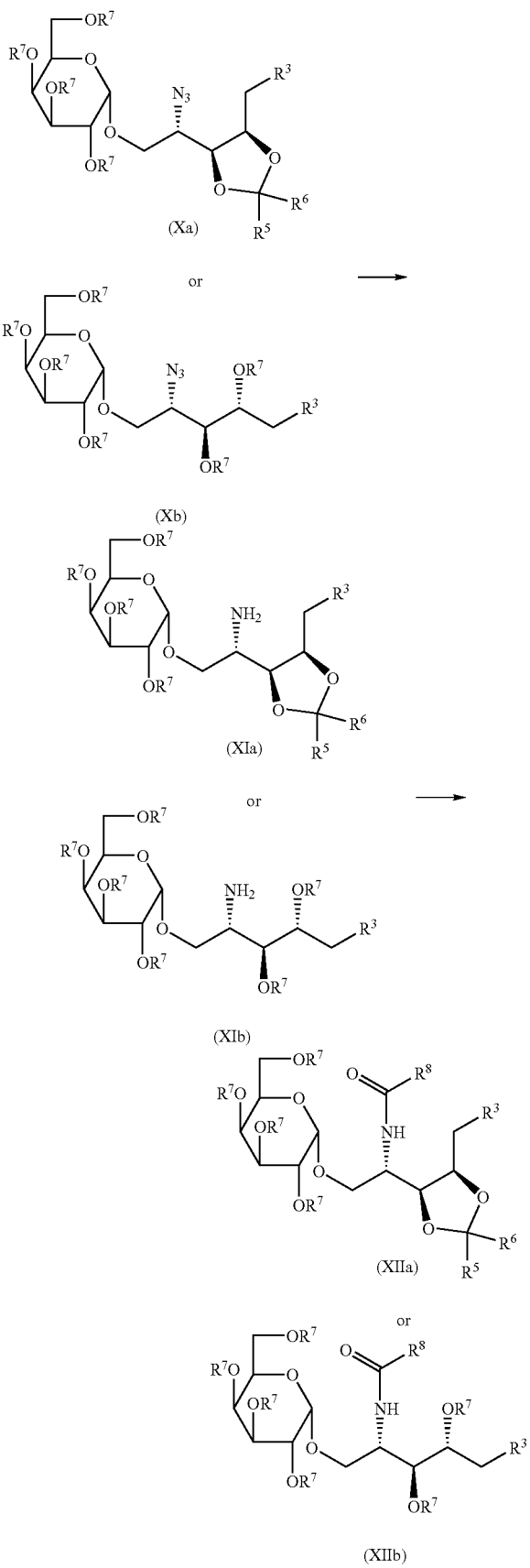

where $R^3$, $R^5$, $R^6$, $R^7$ and X are the same as defined above, and $R^8$ is a substituted or unsubstituted $C_1$ to $C_{35}$ alkyl group, substituted or unsubstituted aryl group, or substituted or unsubstituted aralkyl group.

First, in the reaction for selectively reducing the azide group to an amide group, the compound (Xa) or (Xb) may be treated by zinc/hydrochloric acid, lithium aluminum hydride or another metal reagent or triphenylphosphine, trimethylphosphine, triethylphosphine, tributylphosphine or other triarylphosphine or trialkylphosphine or hydrogenated in the presence of Pd—C, Pd—CaCO$_3$—Pb, Pd—BaSO$_4$, PtO$_2$ etc. at room temperature to convert it to the compound (XIa) or (XIb).

Then, the compound (XIa) or (XIb) obtained may be subjected to an amidation reaction with a carboxylic acid to derive the compound (XIIa) or (XIIb). The amidation reaction used may be one of the many reactions described in *Compendium for Organic Synthesis* (Wiley-Interscience; A Division of John Wiley & Sons) etc. Giving one example, the compound (XIa) or (XIb) may be reacted with a corresponding carboxylic acid in methylene chloride, chloroform, 1,2-dichloroethane, diethylether, tetrahydrofuran, dioxane, acetonitrile, benzene, toluene, xylene, dimethylformamide or another inert solvent in the presence of a carboxylic acid activating agent at, for example, −50° C. to 120° C., preferably −20° C. to 80° C., so as to obtain the compound (XIIa) or (XIIb). As the carboxylic acid activating reagent, silicon tetrachloride, acetic anhydride, acetyl chloride, ethyl chlorocarbonate, 2-iodo-1-methylpyridinium iodide, 2-chloro-1-methylpyridinium iodide, diphenylphosphinylchloride, N,N'-dicyclohexylcarbodiimide (DCC), N-hydroxybenzotriazole/DCC, 1-ethyl-3-(3-diethylaminopropyl)carbodiimide hydrochloride, ethoxyacetylene, trimethylsilylethoxyacetylene, carbodiimidazole, diphenylphosphorylazide, diethylphosphorylcyanidate, etc. may be mentioned. Further, if necessary, p-toluene sulfonic acid, polyphosphoric acid or another acid or triethylamine, diisopropylethylamine, N-methylmorpholine, pyridine, 2,6-Lutidine or another base may be added.

The compound (XIa) or (XIb) obtained by the above reaction may be directly used, as a material for the next step, but may also be used, if necessary, after purification by a general purification method, for example, recrystallization or column chromatography.

Step 7

The compound having the formula (XIIa) obtained at Step 6 may be deacetalized to obtain the compound (XIII) which may then be dearylmethylated to obtain the compound (I). Further, the compound of formula (XIIb) may also be dearylmethylated to similarly obtain the compound (I).

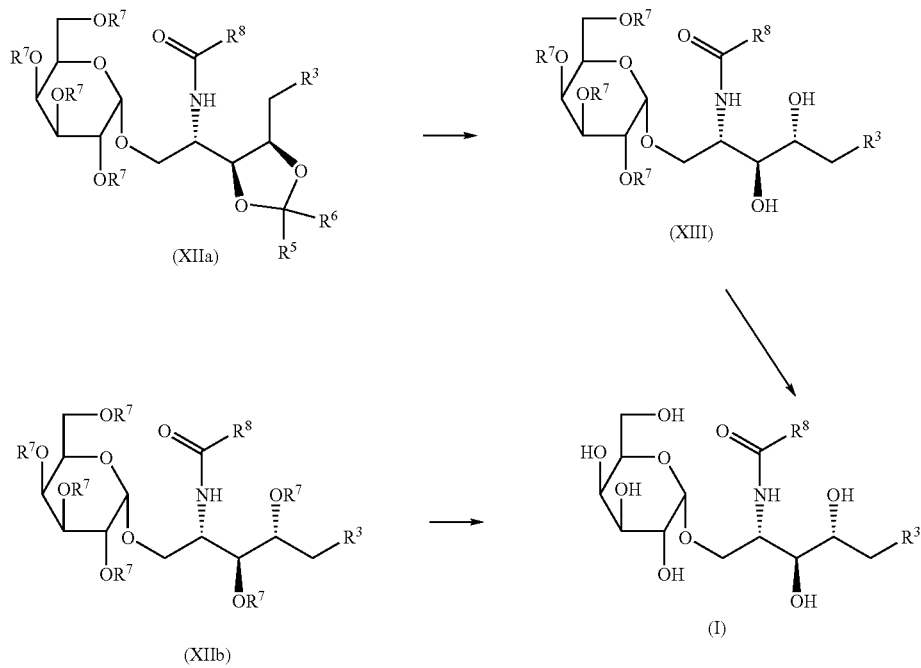

(XIIa)

(XIII)

(XIIb)

(I)

where $R^3$, $R^5$, $R^6$, $R^7$ and $R^8$ are the same as defined above.

For the conditions of the deacetalization and dearylmethylation, it is possible to use the many methods described in *Protective Groups In Organic Synthesis* (John Wiley & Sons) etc. For example, as the conditions for the deacetalization, this may be performed by the method shown in Step 4. Further, as the conditions of the dearylmethylation, heating and refluxing in methanol, ethanol, 2-propanol, ethyl acetate, tetrahydrofuran, dimethylformamide or another solvent not participating in the reaction in the presence of Pd—C, Pd(OH)$_2$, PtO$_2$, etc. with the addition of 4-methylcyclohexene or hydrogenating at room temperature may be mentioned.

The compound (XIIa) obtained by the above reaction may be directly used, as a material for producing the compound (XIII), but may also be used, if necessary, after purification by a general purification method, for example, recrystallization or column chromatography. Further, the compound (I) obtained by this reaction may as required be purification by a general purification method such as recrystallization or column chromatography.

A glycolipid having the formula (I) of the present invention where $R^3$ indicates —(CH$_2$)n-CH$_3$, where n indicates an integer of 0 and 4 to 6, a substituted or unsubstituted cycloalkyl group, a substituted or unsubstituted aryl group, or a substituted or unsubstituted aralkyl group, $R^8$ indicates —(CH$_2$)m-CH$_3$, where m is an integer of 10 to 25, a C$_6$ to C$_{35}$ aryl group unsubstituted or substituted with an alkyl group, alkoxy group, or amide group, or a C$_7$ to C$_{35}$ arakyl group unsubstituted or substituted with an alkyl group, alkoxy group, amide group and a hydrate of a glycolipid having the formula (I), wherein $R^3$ indicates —(CH$_2$)n-CH$_3$, where n indicates an integer of 0 to 6, substituted or unsubstituted cycloalkyl group, substituted or unsubstituted aryl group, or substituted or unsubstituted aralkyl group, and $R^8$ indicates —(CH$_2$)m-CH$_3$, where m indicates an integer of 10 to 25 are useful, as active ingredients of drugs for the treatment of diseases where the Th1/Th2 immune balance is eccentric to the Th1 or diseases where the Th1 cells cause symptoms to worsen and also are useful as active ingredients for Th2 type cytokine producing derivatives.

A glycolipid having the formula (I) of the present invention is low in toxicity. For example, in a test administering compound 107 to 5-week old mice, all 10 subjects administered intraperitoneally doses of 300 µg/kg twice a week for 4 months survived. In the production of the compound (I) of the present invention, when conducting the step of introducing a carbon chain of the Sphingosine base part in the same way as the conventional α-GalCer by a Wittig reaction, the yield is low, and therefore, this cannot be used as a practical method of synthesis. In the present invention, an addition reaction to an epoxy intermediate using an organometallic reagent is used to efficiently introduce the carbon chain of the Sphingosine base part. It is therefore possible to simply produce, at a high yield, a glycolipid where the substituent of the Sphingosine base part of formula (I) is a linear alkyl group with a short substituted or unsubstituted carbon chain, substituted or unsubstituted cycloalkyl group, substituted or unsubstituted aryl group or substituted or unsubstituted aralkyl group. Further, in the hydrate of the glycolipid having the formula (I) of the present invention, improvements in the physical properties and quality were seen. For example, compound 107 does not exhibit a clear melting point, but gradually melts at 120° C. or more and does not exhibit crystallinity even in differential scan calorimetry (DSC) or powder X-ray crystallography, but it is learned that a hydrate of compound 107, that is, compound 129, has a melting point of 142 to 145° C. and exhibits clear crystallinity in differential scan calorimetry (DSC) or powder X-ray crystallography. That is, according to the present invention, it is possible to stably supply uniform quality products in large volumes. The glycolipid (I) of the present invention may be administered alone, but if desired, may be prepared into a target preparation along with another usual pharmacologically acceptable vehicle. That is, the glycolipid (I) may be administered alone, as an active ingredient, or together with a general excipient in a suitable form such as a capsule, tablet, injection, etc. orally or parentally.

The dosage of the drug for treatment of a disease where the Th1/Th2 immune balance is shifted toward the Th1 bias or a disease where the Th1 cells cause the symptoms to worsen or Th2 type cytokine producing derivative of the present invention depends on the patient's condition and age, the route of administration, the form of the drug, the number of times of adminstration, etc., but usually is 0.001 mg to 5000 mg/day/person, preferably 0.01 mg to 500 mg/day/person.

EXAMPLES

The present invention will now be explained in further detail based on Reference Examples and Examples of the invention, but the scope of the present invention is by no means limited to these Examples.

Reference Example 1

Synthesis of 1,3-O-benzylidene-5-O-[(4-methylphenyl)sulfonyl]-D-arabitol (Compound 1)

To 1,3-O-benzylidene-D-arabitol able to be synthesized from D-arabitol and benzaldehyde (R. Wild et al., *Liebigs Ann. Org. Bioorg. Chem.* 1995, 5, 755-764) (34.0 g, 141 mmol) in a methylene chloride (1.2 L) suspension, under ice cooling, dibutyl tin oxide (702 mg, 2.82 mmol) and p-toluene sulfonyl chloride (27.0 g, 141 mmol) were added in small amounts at a time. Further, triethylamine (19.7 ml, 141 mmol) was added. The mixture was stirred at 0° C. to room temperature for 21 hours. The reaction mixture was concentrated, then the residue obtained was purified by silica gel column chromatography (methylene chloride:methanol=20:1) to obtain the above-referenced compound in an amount of 55.3 g (yield 99%).

Reference Example 2

Synthesis of 4,5-anhydro-1,3-O-benzylidene-D-arabitol (Compound 2)

To the compound 1 synthesized in Reference Example 1 (51.1 g, 130 mmol) in a dehydrated tetrahydrofuran (800 ml) solution, under ice cooling, potassium t-butoxide (18.1 g, 161 mmol) was added. The resultant mixture was stirred at 0° C. to room temperature for 38 hours. Water was added to the reaction mixture, then the product was extracted with ethyl acetate (3 times) and washed with brine. The organic layer was dried with sodium sulfate, then filtered and concentrated in vacuo. The residue obtained was purified by silica gel column chromatography (n-hexane:ethyl acetate=1:1) to obtain the above-referenced compound in an amount of 26.2 g (yield 92%).

Example 1

Synthesis of 1,3-O-benzylidene-D-arabino-1,2,3,4-nonanetetraol (Compound 3)

To copper (I) iodide (42.9 g, 225 mmol) in a dehydrated tetrahydrofuran (560 ml) suspension, 2.64M n-butyl lithium/n-hexane solution (341 ml, 900 mmol) was dropwise added at −40° C. and the mixture stirred at −30° C. to −10° C. for 30 minutes to 2 hours. Next, the compound 2 synthesized as shown in Example 2 (50.0 g, 225 mmol) in a dehydrated tetrahydrofuran (400 ml) solution was dropwise added at −40° C. and the resultant mixture stirred at −30° C. to −20° C. for about 3 hours. A saturated ammonium chloride aqueous solution was added to the reaction mixture, the product was extracted with ethyl acetate, and the organic layer was washed with brine, dried with magnesium sulfate, filtered, then concentrated in vacuo to obtain the above-referenced compound 58.4 g (yield 93%).

Example 2

Synthesis of 1,3-O-benzylidene-D-arabino-1,2,3,4-octanetetraol (Compound 4)

The compound 2 and a 2M propylmagnesium bromide/tetrahydrofuran solution were used for the same procedure as with the synthesis of the compound 3 to obtain the above-referenced compound.

Example 3

Synthesis of 1,3-O-benzylidene-D-arabino-1,2,3,4-heptanetetraol (Compound 5)

The compound 2 and a 1.0M ethylmagnesium bromide/tetrahydrofuran solution were used for the same procedure as with synthesis of the compound 3 to obtain the above-referenced compound.

Example 4

Synthesis of 1,3-O-benzylidene-D-arabino-1,2,3,4-hexanetetraol (Compound 6)

The compound 2 and a 1.0M methyl lithium/diethyl ether solution were used for the same procedure as with synthesis of the compound 3 to obtain the above-referenced compound.

Example 5

Synthesis of 1,3-O-benzylidene-D-arabino-1,2,3,4-decanetetraol (Compound 7)

The compound 2 and a 2.0M pentylmagnesium bromide/diethyl ether solution were used for the same procedure as with synthesis of the compound 3 to obtain the above-referenced compound.

Example 6

Synthesis of 6-phenyl-1,3-O-benzylidene-D-arabino-1,2,3,4-hexanetetraol (Compound 8)

The compound 2 and a 2.0M benzylmagnesium chloride/tetrahydrofuran solution were used for the same procedure as with synthesis of the compound 3 to obtain the above-referenced compound.

Example 7

Synthesis of 5-cyclopentyl-1,3-O-benzylidene-D-arabino-1,2,3,4-pentanetetraol (Compound 9)

The compound 2 and a 1.0M cyclopentylmagnesium bromide/tetrahydrofuran solution were used for the same procedure as with synthesis of the compound 3 to obtain the above-referenced compound.

Example 8

Synthesis of 5-(4-methylphenyl)-1,3-O-benzylidene-D-arabino-1,2,3,4-pentanetetraol (Compound 10)

The compound 2 and a 1.0M p-tolylmagnesium bromide/diethylether solution were used for the same procedure as with synthesis of the compound 3 to obtain the above-referenced compound.

Example 9

Synthesis of 5-(2-chloro-3-pyridyl)-1,3-O-benzylidene-D-arabino-1,2,3,4-pentanetetraol (Compound 11)

The compound 2 and 1.0M 2-pyridylmagnesium chloride/tetrahydrofuran solution were used for the same procedure as with synthesis of the compound 3 to obtain the above-referenced compound.

Example 10

Synthesis of 1,3-O-benzylidene-2-O-methanesulfonyl-D-arabino-1,2,3,4-nonanetetraol (Compound 12)

To a dehydrated pyridine (142 ml) solution of the compound 3 synthesized in Example 1 (3.90 g, 13.9 mmol), methanesulfonyl chloride (1.05 ml) was dropwise added at −40° C. The reaction mixture was stirred at −40° C. to −30° C. for 5 hours and at room temperature over night. The reaction mixture was concentrated, then toluene was used for azeotropic removal of pyridine (2 times), then the residue obtained was purified by silica gel column chromatography (n-hexane:ethyl acetate=3:2) to obtain the above-referenced compound in an amount of 4.65 g (yield 93%).

Example 11

Synthesis of 1,3-O-benzylidene-2-O-methanesulfonyl-D-arabino-1,2,3,4-octanetetraol (Compound 13)

The compound 4 synthesized in Example 2 was used for the same procedure as in Example 10 to obtain the above-referenced compound.

Example 12

Synthesis of 1,3-O-benzylidene-2-O-methanesulfonyl-D-arabino-1,2,3,4-heptanetetraol (Compound 14)

The compound 5 synthesized in Example 3 was used for the same procedure as in Example 10 to obtain the above-referenced compound.

Example 13

Synthesis of 1,3-O-benzylidene-2-O-methanesulfonyl-D-arabino-1,2,3,4-hexanetetraol (Compound 15)

The compound 6 synthesized in Example 4 was used for the same procedure as in Example 10 to obtain the above-referenced compound.

Example 14

Synthesis of 1,3-O-benzylidene-2-O-methanesulfonyl-D-arabino-1,2,3,4-decanetetraol (Compound 16)

The compound 7 synthesized in Example 5 was used for the same procedure as in Example 10 to obtain the above-referenced compound.

Example 15

Synthesis of 6-phenyl-1,3-O-benzylidene-2-O-methanesulfonyl-D-arabino-1,2,3,4-hexanetetraol (Compound 17)

The compound 8 synthesized in Example 6 was used for the same procedure as in Example 10 to obtain the above-referenced compound.

Example 16

Synthesis of 5-cyclopentyl-1,3-O-benzylidene-2-O-methanesulfonyl-D-arabino-1,2,3,4-pentanetetraol (Compound 18)

The compound 9 synthesized in Example 7 was used for the same procedure as in Example 10 to obtain the above-referenced compound.

Example 17

Synthesis of 5-(4-methylphenyl)-1,3-O-benzylidene-2-O-methanesulfonyl-D-arabino-1,2,3,4-pentanetetraol (Compound 19)

The compound 10 synthesized in Example 8 was used for the same procedure as in Example 10 to obtain the above-referenced compound.

Example 18

Synthesis of 5-(2-chloro-3-pyridyl)-1,3-O-benzylidene-2-O-methanesulfonyl-D-arabino-1,2,3,4-pentanetetraol (Compound 20)

The compound 11 synthesized in Example 9 was used for the same procedure as in Example 10 to obtain the above-referenced compound.

Example 19

Synthesis of 2-azido-1,3-O-benzylidene-D-ribo-1,3,4-nonanetriol (Compound 21)

To the compound 12 synthesized at Example 10 (4.60 g, 12.8 mmol) in a dehydrated dimethylformamide (128 ml) solution, sodium azide (10.0 g) was added. The mixture was stirred at 110° C. for 7 hours. Water was added to the reaction mixture, the product was extracted with ethyl acetate, and the organic layer was washed with brine (2 times), was dried with sodium sulfate, filtered, then concentrated in vacuo. The residue obtained was purified by silica gel column chromatography (n-hexane:ethyl acetate=8:1) to obtain the above-referenced compound in an amount of 1.53 g (yield 39%).

Example 20

Synthesis of
2-azido-1,3-O-benzylidene-D-ribo-1,3,4-octanetriol
(Compound 22)

The compound 13 synthesized in Example 11 was used for the same procedure as in Example 19 to obtain the above-referenced compound.

Example 21

Synthesis of 2-azido-1,3-O-benzylidene-D-ribo-1,3,4-heptanetriol (Compound 23)

The compound 14 synthesized in Example 12 was used for the same procedure as in Example 19 to obtain the above-referenced compound.

Example 22

Synthesis of
2-azido-1,3-O-benzylidene-D-ribo-1,3,4-hexanetriol
(Compound 24)

The compound 15 synthesized in Example 13 was used for the same procedure as in Example 19 to obtain the above-referenced compound.

Example 23

Synthesis of
2-azido-1,3-O-benzylidene-D-ribo-1,3,4-decanetriol
(Compound 25)

The compound 16 synthesized in Example 14 was used for the same procedure as in Example 19 to obtain the above-referenced compound.

Example 24

Synthesis of 6-phenyl-2-azido-1,3-O-benzylidene-D-ribo-1,3,4-hexanetriol (Compound 26)

The compound 17 synthesized in Example 15 was used for the same procedure as in Example 19 to obtain the above-referenced compound.

Example 25

Synthesis of 5-cyclopentyl-2-azido-1,3-O-benzylidene-D-ribo-1,3,4-pentanetriol (Compound 27)

The compound 18 synthesized in Example 16 was used for the same procedure as in Example 19 to obtain the above-referenced compound.

Example 26

Synthesis of 5-(4-methylphenyl)-2-azido-1,3-O-benzylidene-D-ribo-1,3,4-pentanetriol (Compound 28)

The compound 19 synthesized in Example 17 was used for the same procedure as in Example 19 to obtain the above-referenced compound.

Example 27

Synthesis of 5-(2-chloro-3-pyridyl)-2-azido-1,3-O-benzylidene-D-ribo-1,3,4-pentanetriol (Compound 29)

The compound 20 synthesized in Example 18 was used for the same procedure as in Example 19 to obtain the above-referenced compound.

Example 28

Synthesis of 2-azido-D-ribo-1,3,4-nonanetriol (Compound 30)

To the compound 21 synthesized in Example 19 (11.4 g, 37.3 mmol) in a methanol (180 ml) solution, under ice cooling, 6N hydrochloric acid aqueous solution (17.8 ml) was added. The mixture was stirred at room temperature overnight. The reaction mixture was neutralized with triethylamine or potassium carbonate, then was concentrated in vacuo. The residue obtained was purified by silica gel column chromatography (methylene chloride:methanol=15:1) to obtain the above-referenced compound in an amount of 6.1 g (yield 79%).

Example 29

Synthesis of 2-azido-D-ribo-1,3,4-octanetriol (Compound 31)

The compound 22 synthesized in Example 20 was used for the same procedure as in Example 28 to obtain the above-referenced compound.

Example 30

Synthesis of 2-azido-D-ribo-1,3,4-heptanetriol (Compound 32)

The compound 23 synthesized in Example 21 was used for the same procedure as in Example 28 to obtain the above-referenced compound.

Example 31

Synthesis of 2-azido-D-ribo-1,3,4-hexanetriol (Compound 33)

The compound 24 synthesized in Example 22 was used for the same procedure as in Example 28 to obtain the above-referenced compound.

Example 32

Synthesis of 2-azido-D-ribo-1,3,4-decanetriol (Compound 34)

The compound 25 synthesized in Example 23 was used for the same procedure as in Example 28 to obtain the above-referenced compound.

Example 33

Synthesis of
6-phenyl-2-azido-D-ribo-1,3,4-hexanetriol
(Compound 35)

The compound 26 synthesized in Example 24 was used for the same procedure as in Example 28 to obtain the above-referenced compound.

Example 34

Synthesis of 5-cyclopentyl-2-azido-D-ribo-1,3,4-pentanetriol (Compound 36)

The compound 27 synthesized in Example 25 was used for the same procedure as in Example 28 to obtain the above-referenced compound.

Example 35

Synthesis of 5-(4-methylphenyl)-2-azido-D-ribo-1,3,4-pentanetriol (Compound 37)

The compound 28 synthesized in Example 26 was used for the same procedure as in Example 28 to obtain the above-referenced compound.

Example 36

Synthesis of 5-(2-chloro-3-pyridyl)-2-azido-D-ribo-1,3,4-pentanetriol (Compound 38)

The compound 29 synthesized in Example 27 was used for the same procedure as in Example 28 to obtain the above-referenced compound.

Example 37

Synthesis of 2-O-methanesulfonyl-D-arabino-1,2,3,4-nonanetetraol (Compound 39)

To the compound 12 synthesized in Example 10 (87.0 mg, 0.242 mmol) in an ethanol (5 ml) solution, palladium hydroxide (45 mg) was added. The mixture was stirred at ordinary pressure and room temperature over night to hydrogenate it. The catalyst was filtered off and the filtrate was concentrated in vacuo to obtain the above-referenced compound in an amount of 65.7 mg (yield 100%).

Example 38

Synthesis of 2-azido-D-ribo-1,3,4-nonanetriol (Compound 30)

To the compound 39 synthesized at Example 37 (36.9 mg, 0.136 mmol) in a dehydrated dimethylformamide (1 ml) solution, sodium azide (18 mg) was added and the mixture stirred at 95° C. for 3 hours. Water was added to the reaction mixture, the product was extracted with ethyl acetate, and the organic layer was washed with saturated saline (2 times), was dried with sodium sulfate, filtered, then condensed in vacuo. The residue obtained was purified by silica gel column chromatography (methylene chloride:methanol=15:1) to obtain the above-referenced compound in an amount of 17.2 mg (yield 58%).

Example 39

Synthesis of 2-azido-3,4-O-isopropylidene-D-ribo-1,13,4-nonanetriol (Compound 40)

To the compound 30 synthesized in Example 28 (4.00 g, 18.4 mmol) in a dimethoxypropane (73 ml) solution, under ice cooling, p-toluene sulfonic acid-hydrate (175 mg, 0.92 mmol) was added and the mixture stirred at room temperature for 2 hours. Next, methanol was added to the reaction mixture, the mixture was stirred at room temperature for 1 hour, then the reaction mixture was concentrated in vacuo. The residue obtained was purified by silica gel column chromatography (n-hexane:ethyl acetate=4:1) to obtain the above-referenced compound in an amount of 3.61 g (yield 75%).

Example 40

Synthesis of 2-azido-3,4-O-isopropylidene-D-ribo-1,3,4-octanetriol (Compound 41)

The compound 31 synthesized in Example 29 was used for the same procedure as in Example 39 to obtain the above-referenced compound.

Example 41

Synthesis of 2-azido-3,4-O-isopropylidene-D-ribo-1,3,4-heptanetriol (Compound 42)

The compound 32 synthesized in Example 30 was used for the same procedure as in Example 39 to obtain the above-referenced compound.

Example 42

Synthesis of 2-azido-3,4-O-isopropylidene-D-ribo-1,3,4-hexanetriol (Compound 43)

The compound 33 synthesized in Example 31 was used for the same procedure as in Example 39 to obtain the above-referenced compound.

Example 43

Synthesis of 2-azido-3,4-O-isopropylidene-D-ribo-1,3,4-decanetriol (Compound 44)

The compound 34 synthesized in Example 32 was used for the same procedure as in Example 39 to obtain the above-referenced compound.

Example 44

Synthesis of 6-phenyl-2-azido-3,4-O-isopropylidene-D-ribo-1,3,4-hexanetriol (Compound 45)

The compound 35 synthesized in Example 33 was used for the same procedure as in Example 39 to obtain the above-referenced compound.

Example 45

Synthesis of 5-cyclopentyl-2-azido-3,4-O-isopropylidene-D-ribo-1,3,4-pentanetriol (Compound 46)

The compound 35 synthesized in Example 33 was used for the same procedure as in Example 39 to obtain the above-referenced compound.

Example 46

Synthesis of 5-(4-methylphenyl)-2-azido-3,4-O-isopropylidene-D-ribo-1,3,4-pentanetriol (Compound 47)

The compound 36 synthesized in Example 34 was used for the same procedure as in Example 39 to obtain the above-referenced compound.

Example 47

Synthesis of 2-azido-1-O-(2,3,4,6-tetra-O-benzyl-α-D-galactopyranosyl)-3,4-O-isopropylidene-D-ribo-1,3,4-nonanetriol (Compound 48)

To dried molecular sieve (4A, powder) (1.96 g), the compound 40 synthesized in Example 39 (431 mg, 1.68 mmol) and 2,3,4,6-tetra-O-benzyl-α-D-galactopyranosyl fluoride (Hayashi et al., *Chem. Lett.* 1984, 1747) (1.22 g, 2.26 mmol) in dehydrated chloroform (39 ml) solution was added and the mixture was stirred at room temperature for 30 minutes. Then, boron trifluoride-ether complex (201 μl, 1.59 mmol) in dehydrated chloroform (7 ml) was dropwise added at –50° C. and the reaction mixture was stirred at –50° C. to –30° C. for 6 hours and at 0° C. over night. The molecular sieve was filtered off, then a saturated sodium hydrogen carbonate aqueous solution was added to the reaction mixture. The product was extracted with chloroform, and the organic layer was dried using magnesium sulfate, filtered, then concentrated in vacuo. The residue obtained was purified by silica gel column chromatography (n-hexane:ethyl acetate=10:1 to 5:1) to obtain the above-referenced compound in an amount of 712 mg (yield 57%).

Example 48

Synthesis of 2-azido-1-O-(2,3,4,6-tetra-O-benzyl-α-D-galactopyranosyl)-3,4-O-isopropylidene-D-ribo-1,3,4-nonanetriol (Compound 48)

To dried molecular sieve (4A, powder)(340 mg) in a suspension of toluene (3.4 ml) and dimethylformamide (1.4 ml), the compound 40 synthesized in Example 39 (100 mg, 0.389 mmol), 2,3,4,6-tetra-O-benzyl-α-D-galactopyranosyl bromide synthesizable from 2,3,4,6-tetra-O-benzyl-α-D-nalactopyranose (Spohr et al., *Can. J. Chem.*, 2001, 79, 238)(428 mg, 0.710 mmol), and tetra-n-butylammonium bromide (377 mg, 1.17 mmol) were added and the mixture was stirred at room temperature for 5 days. To the reaction mixture, methanol (0.1 ml) was added, the mixture was stirred at room temperature for 1 hour, then was filtered. The filtrate was washed with saturated sodium hydrogen carbonate aqueous solution, water, and brine, then the organic layer was dried by magnesium sulfate, filtered, and concentrated in vacuo. The obtained residue was purified by silica gel column chromatography (n-hexane:ethyl acetate=7:1) to obtain the above-referenced compound in an amount of 206 mg (yield 68%).

Example 49

Synthesis of 2-azido-1-O-(2,3,4,6-tetra-O-benzyl-α-D-galactopyranosyl)-3,4-O-isopropylidene-D-ribo-1,3,4-octanetriol (Compound 49)

The compound 41 synthesized in Example 40 was used for the same procedure as in Example 47 to obtain the above-referenced compound.

Example 50

Synthesis of 2-azido-1-O-(2,3,4,6-tetra-O-benzyl-α-D-galactopyranosyl)-3,4-O-isopropylidene-D-ribo-1,3,4-heptanetriol (Compound 50)

The compound 42 synthesized in Example 41 was used for the same procedure as in Example 47 to obtain the above-referenced compound.

Example 51

Synthesis of 2-azido-1-O-(2,3,4,6-tetra-O-benzyl-α-D-galactopyranosyl)-3,4-O-isopropylidene-D-ribo-1,3,4-hexanetriol (Compound 51)

The compound 43 synthesized in Example 42 was used for the same procedure as in Example 47 to obtain the above-referenced compound.

Example 52

Synthesis of 2-azido-1-O-(2,3,4,6-tetra-O-benzyl-α-D-galactopyranosyl)-3,4-O-isopropylidene-D-ribo-1,3,4-decanetriol (Compound 52)

The compound 44 synthesized in Example 43 was used for the same procedure as in Example 47 to obtain the above-referenced compound.

Example 53

Synthesis of 6-phenyl-2-azido-1-O-(2,3,4,6-tetra-O-benzyl-α-D-galactopyranosyl)-3,4-O-isopropylidene-D-ribo-1,3,4-hexanetriol (Compound 53)

The compound 45 synthesized in Example 44 was used for the same procedure as in Example 47 to obtain the above-referenced compound.

Example 54

Synthesis of 5-cyclopentyl-2-azido-1-O-(2,3,4,6-tetra-O-benzyl-α-D-galactopyranosyl)-3,4-O-isopropylidene-D-ribo-1,3,4-pentanetriol (Compound 54)

The compound 46 synthesized in Example 45 was used for the same procedure as in Example 47 to obtain the above-referenced compound.

Example 55

Synthesis of 5-(4-methylphenyl)-2-azido-1-O-(2,3,4,6-tetra-O-benzyl-α-D-galactopyranosyl)-3,4-O-isopropylidene-D-ribo-1,3,4-pentanetriol (Compound 55)

The compound 47 synthesized in Example 46 was used for the same procedure as in Example 47 to obtain the above-referenced compound.

Example 56

Synthesis of 2-amino-1-O-(2,3,4,6-tetra-O-benzyl-α-D-galactopyranosyl)-3,4-O-isopropylidene-D-ribo-1,3,4-nonanetriol (Compound 56)

To the compound 48 synthesized in Example 47 (2.58 g, 3.31 mmol) in an ethanol (260 ml) solution, palladium-calcium carbonate (lead poisoned) (Lindlar catalyst)(2.60 g) was added. The mixture was stirred at ordinary pressure at room temperature over night for hydrogenation. The catalyst was filtered off, then the filtrate was concentrated in vacuo to obtain the above-referenced compound 2.46 g (yield 99%).

Example 57

Synthesis of 2-amino-1-O-(2,3,4,6-tetra-O-benzyl-α-D-galactopyranosyl)-3,4-O-isopropylidene-D-ribo-1,3,4-octanetriol (Compound 57)

The compound 49 synthesized in Example 49 was used for the same procedure as in Example 56 to obtain the above-referenced compound.

Example 58

Synthesis of 2-amino-1-O-(2,3,4,6-tetra-O-benzyl-α-D-galactopyranosyl)-3,4-O-isopropylidene-D-ribo-1,3,4-heptanetriol (Compound 58)

The compound 50 synthesized in Example 50 was used for the same procedure as in Example 56 to obtain the above-referenced compound.

Example 59

Synthesis of 2-amino-1-O-(2,3,4,6-tetra-O-benzyl-α-D-galactopyranosyl)-3,4-O-isopropylidene-D-ribo-1,3,4-decanetriol (Compound 59)

The compound 51 synthesized in Example 51 was used for the same procedure as in Example 56 to obtain the above-referenced compound.

Example 60

Synthesis of 6-phenyl-2-amino-1-O-(2,3,4,6-tetra-O-benzyl-α-D-galactopyranosyl)-3,4-O-isopropylidene-D-ribo-1,3,4-hexanetriol (Compound 60)

The compound 53 synthesized in Example 53 was used for the same procedure as in Example 56 to obtain the above-referenced compound.

Example 61

Synthesis of 5-cyclopentyl-2-amino-1-O-(2,3,4,6-tetra-O-benzyl-α-D-galactopyranosyl)-3,4-O-isopropylidene-D-ribo-1,3,4-pentanetriol (Compound 61)

The compound 54 synthesized in Example 54 was used for the same procedure as in Example 56 to obtain the above-referenced compound.

Example 62

Synthesis of 5-(4-methylphenyl)-2-amino-1-O-(2,3,4,6-tetra-O-benzyl-α-D-galactopyranosyl)-3,4-O-isopropylidene-D-ribo-1,3,4-pentanetriol (Compound 62)

The compound 55 synthesized in Example 55 was used for the same procedure as in Example 56 to obtain the above-referenced compound.

Example 63

Synthesis of 2-tetracosanoylamino-1-O-(2,3,4,6-tetra-O-benzyl-α-D-galactopyranosyl)-3,4-O-isopropylidene-D-ribo-1,3,4-nonanetriol (Compound 63)

To n-tetracosanic acid (1.22 g, 3.31 mmol) in a suspension of dimethylformamide (90 ml) and methylene chloride (210 ml), under ice cooling, 1-ethyl-3-(3-dimethylaminopropyl) carboduimide hydrochloride (761 mg, 3.97 mmol) and 1-hydroxybenzotriazole (536 mg, 3.97 mmol) were added and the mixture was stirred at room temperature for 30 minutes. Then, to the reaction mixture, the compound 56 synthesized in Example 56 (2.46 g, 3.26 mmol) and N,N-diisopropylethylamine (1.38 ml, 7.97 mmol) in a methylene chloride (120 ml) solution were added and the mixture was stirred at 30° C. over night. The reaction solution was diluted with a mixed solvent of ethyl acetate/diethylether=4/1, then was washed with a saturated sodium hydrogen carbonate aqueous solution, 1N hydrochloric acid, water, and brine. The organic layer was dried with sodium sulfate, filtered, and concentrated in vacuo. The residue obtained was purified by silica gel column chromatography (n-hexane:ethyl acetate=5:1 to 3:1) to obtain the above-referenced compound in an amount of 3.25 g (yield 89%).

Example 64

Synthesis of 2-tricosanoylamino-1-O-(2,3,4,6-tetra-O-benzyl-α-D-galactopyranosyl)-3,4-O-isopropylidene-D-ribo-1,3,4-nonanetriol (Compound 64)

The compound 56 synthesized in Example 56 and tricosanic acid were used for the same procedure as in Example 63 to obtain the above-referenced compound.

Example 65

Synthesis of 2-docasanoylamino-1-O-(2,3,4,6-tetra-O-benzyl-α-D-galactopyranosyl)-3,4-O-isopropylidene-D-ribo-1,3,4-nonanetriol (Compound 65)

The compound 56 synthesized in Example 56 and docosanic acid were used for the same procedure as in Example 63 to obtain the above-referenced compound.

Example 66

Synthesis of 2-tricosanoylamino-1-O-(2,3,4,6-tetra-O-benzyl-α-D-galactopyranosyl)-3,4-O-isopropylidene-D-ribo-1,3,4-octanetriol (Compound 66)

The compound 57 synthesized in Example 57 and tricosanic acid were used for the same procedure as in Example 63 to obtain the above-referenced compound.

Example 67

Synthesis of 2-docasanoylamino-1-O-(2,3,4,6-tetra-O-benzyl-α-D-galactopyranosyl)-3,4-O-isopropylidene-D-ribo-1,3,4-heptanetriol (Compound 67)

The compound 58 synthesized in Example 58 and docosanic acid were used for the same procedure as in Example 63 to obtain the above-referenced compound.

Example 68

Synthesis of 2-tricosanoylamino-1-O-(2,3,4,6-tetra-O-benzyl-α-D-galactopyranosyl)-3,4-O-isopropylidene-D-ribo-1,3,4-hexanetriol (Compound 68)

The compound obtained by hydrogenating the compound 51 synthesized in Example 51 in the same way as Example 56 and tricosanic acid were used for the same procedure as in Example 63 to obtain the above-referenced compound.

Example 69

Synthesis of 2-docasanoylamino-1-O-(2,3,4,6-tetra-O-benzyl-α-D-galactopyranosyl)-3,4-O-isopropylidene-D-ribo-1,3,4-decanetriol (Compound 69)

The compound 59 synthesized in Example 59 and docosanic acid were used for the same procedure as in Example 63 to obtain the above-referenced compound.

Example 70

Synthesis of 2-tricosanoylamino-1-O-(2,3,4,6-tetra-O-benzyl-α-D-galactopyranosyl)-3,4-O-isopropylidene-D-ribo-1,3,4-decanetriol (Compound 70)

The compound 59 synthesized in Example 59 and n-tricosanic acid were used for the same procedure as in Example 63 to obtain the above-referenced compound.

Example 71

Synthesis of 6-phenyl-2-tetracosanoylamino-1-O-(2,3,4,6-tetra-O-benzyl-α-D-galactopyranosyl)-3,4-O-isopropylidene-D-ribo-1,3,4-hexanetriol (Compound 71)

The compound 60 synthesized in Example 60 and n-tetracosanic acid were used for the same procedure as in Example 63 to obtain the above-referenced compound.

Example 72

Synthesis of 5-cyclopentyl-2-tetracosanoylamino-1-O-(2,3,4,6-tetra-O-benzyl-α-D-galactopyranosyl)-3,4-O-isopropylidene-D-ribo-1,3,4-pentanetriol (Compound 72)

The compound 61 synthesized in Example 61 and n-tetracosanic acid were used for the same procedure as in Example 63 to obtain the above-referenced compound.

Example 73

Synthesis of 5-(4-methylphenyl)-2-tetracosanoylamino-1-O-(2,3,4,6-tetra-O-benzyl-α-D-galactopyranosyl)-3,4-O-isopropylidene-D-ribo-1,3,4-pentanetriol (Compound 73)

The compound 62 synthesized in Example 62 and n-tetracosanic acid were used for the same procedure as in Example 63 to obtain the above-referenced compound.

Example 74

Synthesis of 2-(3-phenylpropanoylamino)-1-O-(2,3,4,6-tetra-O-benzyl-α-D-galactopyranosyl)-3,4-O-isopropylidene-D-ribo-1,3,4-nonanetriol (Compound 74)

The compound 56 synthesized in Example 56 and 3-phenylpropanic acid were used for the same procedure as in Example 63 to obtain the above-referenced compound.

Example 75

Synthesis of 2-(5-phenylpentanoylamino)-1-O-(2,3,4,6-tetra-O-benzyl-α-D-galactopyranosyl)-3,4-O-isopropylidene-D-ribo-1,3,4-nonanetriol (Compound 75)

The compound 56 synthesized in Example 56 and 5-phenylpentanic acid were used for the same procedure as in Example 63 to obtain the above-referenced compound.

Example 76

Synthesis of 2-[3-(4-octyloxyphenyl) propanoylamino]-1-O-(2,3,4,6-tetra-O-benzyl-α-D-galactopyranosyl)-3,4-O-isopropylidene-D-ribo-1,3,4-nonanetriol (Compound 76)

The compound 56 synthesized in Example 56 and 3-(4-octyloxyphenyl)propanic acid (Wissner et al., *J. Med. Chem.* 1992, 35, 4779.) were used for the same procedure as in Example 63 to obtain the above-referenced compound.

Example 77

Synthesis of 2-[3-(4-hexadecanyloxyphenyl) propanoylamino]-1-O-(2,3,4,6-tetra-O-benzyl-α-D-galactopyranosyl)-3,4-O-isopropylidene-D-ribo-1,3,4-nonanetriol (Compound 77)

The compound 56 synthesized in Example 56 and 3-(4-hexadecanyloxyphenyl)propanic acid (Wissner et al., *J. Med. Chem.* 1992, 35, 4779.) were used for the same procedure as in Example 63 to obtain the above-referenced compound.

Example 78

Synthesis of 2-{5-[4-(4-octylbenzoylamino) phenyl]pentanoylamino}-1-O-(2,3,4,6-tetra-O-benzyl-α-D-galactopyranosyl)-3,4-O-isopropylidene-D-ribo-1,3,4-nonanetriol (Compound 78)

The compound 56 synthesized in Example 56 and 5-[4-(4-octylbenzoylamino)phenyl]pentanic acid (Wissner et al., *J. Med. Chem.* 1992, 35, 4779.) were used for the same procedure as in Example 63 to obtain the above-referenced compound.

Example 79

Synthesis of 2-[3-(4-octadecylphenyl) propanoylamino]-1-O-(2,3,4,6-tetra-O-benzyl-α-D-galactopyranosyl)-3,4-O-isopropylidene-D-ribo-1,3,4-nonanetriol (Compound 79)

The compound 56 synthesized in Example 56 and 3-(4-octadecylphenyl)propanic acid (Clark, *J. Chem. Soc.* 1957, 2202.) were used for the same procedure as in Example 63 to obtain the above-referenced compound.

Example 80

Synthesis of 2-(4-nonadecylbenzoylamino)-1-O-(2,3,4,6-tetra-O-benzyl-α-D-galactopyranosyl)-3,4-O-isopropylidene-D-ribo-1,3,4-nonanetriol (Compound 80)

The compound 56 synthesized by Example 56 and 4-nonadecylbenzoic acid (Parker et al., *J. Med. Chem.* 1977, 20, 781.) were used for the same procedure as in Example 63 to obtain the above-referenced compound.

Example 81

Synthesis of 2-[5-(4-tetradecyl-1-piperadinyl)pentanoylamino]-1-O-(2,3,4,6-tetra-O-benzyl-α-D-galactopyranosyl)-3,4-O-isopropylidene-D-ribo-1,3,4-nonanetriol (Compound 81)

The compound 56 synthesized in Example 56 and 5-(4-tetradecyl-1-piperadinyl)pentanoic acid (Buzas et al., *J. Med. Chem.* 1980, 2, 149.) were used for the same procedure as in Example 63 to obtain the above-referenced compound.

Example 82

Synthesis of 2-[5-(4-hexyloxyphenyl) pentanoylamino]-1-O-(2,3,4,6-tetra-O-benzyl-α-D-galactopyranosyl)-3,4-O-isopropylidene-D-ribo-1,3,4-nonanetriol (Compound 82)

The compound 56 synthesized in Example 56 and 5-(4-hexyloxyphenyl)pentanoic acid (Rona, *J. Chem. Soc.* 1962, 3629.) were used for the same procedure as in Example 63 to obtain the above-referenced compound.

Example 83

Synthesis of 2-[5-(4-tetradecyloxyphenyl) pentanoylamino]-1-O-(2,3,4,6-tetra-O-benzyl-α-D-galactopyranosyl)-3,4-O-isopropylidene-D-ribo-1,3,4-nonanetriol (Compound 83)

The compound 56 synthesized in Example 56 and 5-(4-tetradecyloxyphenyl)pentanoic acid (Rona, *J. Chem. Soc.* 1962, 3629.) were used for the same procedure as in Example 63 to obtain the above-referenced compound.

Example 84

Synthesis of 2-{5-(4'-pentyl-[1,1'-biphenyl]-4-yl) pentanoylamino}-1-O-(2,3,4,6-tetra-O-benzyl-α-D-galactopyranosyl)-3,4-O-isopropylidene-D-ribo-1,3,4-nonanetriol (Compound 84)

The compound 56 synthesized in Example 56 and 5-(4'-pentyl-[1,1'-biphenyl]-4-yl)pentanoic acid (Sakaguchi et al., *Syn. Lett.* 1997, 5, 624.) were used for the same procedure as in Example 63 to obtain the above-referenced compound.

Example 85

Synthesis of 2-tetracosanoylamino-1-O-(2,3,4,6-tetra-O-benzyl-α-D-galactopyranosyl)-D-ribo-1,3,4-nonanetriol (Compound 85)

A solution of the compound 63 synthesized in Example 63 (89 mg, 0.081 mmol) in a methanol (1 ml)/methylene chloride (5 ml)/4N hydrochloric acid-dioxane (100 μl) was stirred at room temperature for 2 hours, then concentrated in vacuo. The obtained residue was purified by silica gel column chromatography (methylene chloride:methanol=30:1) to obtain the above-referenced compound 70 mg (yield 82%). Further, the above-referenced compound could also be obtained by stirring the compound 63 in an 80% acetic acid aqueous solution at 45° C. over night, then concentrating the reaction mixture in vacuo.

Example 86

Synthesis of 2-tricosanoylamino-1-O-(2,3,4,6-tetra-O-benzyl-α-D-galactopyranosyl)-D-ribo-1,3,4-nonanetriol (Compound 86)

The compound 64 synthesized in Example 64 was used for the same procedure as in Example 85 to obtain the above-referenced compound.

Example 87

Synthesis of 2-docasanoylamino-1-O-(2,3,4,6-tetra-O-benzyl-α-D-galactopyranosyl)-D-ribo-1,3,4-nonanetriol (Compound 87)

The compound 65 synthesized in Example 65 was used for the same procedure as in Example 85 to obtain the above-referenced compound.

Example 88

Synthesis of 2-tricosanoylamino-1-O-(2,3,4,6-tetra-O-benzyl-α-D-galactopyranosyl)-D-ribo-1,3,4-octanetriol (Compound 88)

The compound 66 synthesized in Example 66 was used for the same procedure as in Example 85 to obtain the above-referenced compound.

Example 89

Synthesis of 2-docasanoylamino-1-O-(2,3,4,6-tetra-O-benzyl-α-D-galactopyranosyl)-D-ribo-1,3,4-heptanetriol (Compound 89)

The compound 67 synthesized in Example 67 was used for the same procedure as in Example 85 to obtain the above-referenced compound.

Example 90

Synthesis of 2-tricosanoylamino-1-O-(2,3,4,6-tetra-O-benzyl-α-D-galactopyranosyl)-D-ribo-1, 3,4-hexanetriol (Compound 90)

The compound 68 synthesized in Example 68 was used for the same procedure as in Example 85 to obtain the above-referenced compound.

Example 91

Synthesis of 2-docasanoylamino-1-O-(2,3,4,6-tetra-O-benzyl-α-D-galactopyranosyl)-D-ribo-1,3,4-decanetriol (Compound 91)

The compound 69 synthesized in Example 69 was used for the same procedure as in Example 85 to obtain the above-referenced compound.

Example 92

Synthesis of 2-tricosanoylamino-1-O-(2,3,4,6-tetra-O-benzyl-α-D-galactopyranosyl)-D-ribo-1,3,4-decanetriol (Compound 92)

The compound 70 synthesized in Example 70 was used for the same procedure as in Example 85 to obtain the above-referenced compound.

Example 93

Synthesis of 6-phenyl-2-tetracosanoylamino-1-O-(2, 3,4,6-tetra-O-benzyl-α-D-galactopyranosyl)-D-ribo-1,3,4-hexanetriol (Compound 93)

The compound 71 synthesized in Example 71 was used for the same procedure as in Example 85 to obtain the above-referenced compound.

Example 94

Synthesis of 5-cyclopentyl-2-tetracosanoylamino-1-O-(2,3,4,6-tetra-O-benzyl-α-D-galactopyranosyl)-D-ribo-1,3,4-pentanetriol (Compound 94)

The compound 72 synthesized in Example 72 was used for the same procedure as in Example 85 to obtain the above-referenced compound.

Example 95

Synthesis of 5-(4-methylphenyl)-2-tetracosanoylamino-1-O-(2,3,4,6-tetra-O-benzyl-α-D-galactopyranosyl)-D-ribo-1,3,4-pentanetriol (Compound 95)

The compound 73 synthesized in Example 73 was used for the same procedure as in Example 85 to obtain the above-referenced compound.

Example 96

Synthesis of 2-(3-phenylpropanoylamino)-1-O-(2,3,4,6-tetra-O-benzyl-α-D-galactopyranosyl)-D-ribo-1,3,4-nonanetriol (Compound 96)

The compound 74 synthesized in Example 74 was used for the same procedure as in Example 85 to obtain the above-referenced compound.

Example 97

Synthesis of 2-(5-phenylpentanoylamino)-1-O-(2,3,4,6-tetra-O-benzyl-α-D-galactopyranosyl)-D-ribo-1,3,4-nonanetriol (Compound 97)

The compound 75 synthesized in Example 75 was used for the same procedure as in Example 85 to obtain the above-referenced compound.

Example 98

Synthesis of 2-[3-(4-octyloxyphenyl) propanoylamino]-1-O-(2,3,4,6-tetra-O-benzyl-α-D-galactopyranosyl)-D-ribo-1,3,4-nonanetriol (Compound 98)

The compound 76 synthesized in Example 76 was used for the same procedure as in Example 85 to obtain the above-referenced compound.

Example 99

Synthesis of 2-[3-(4-hexadecanyloxyphenyl) propanoylamino]-1-O-(2,3,4,6-tetra-O-benzyl-α-D-galactopyranosyl)-D-ribo-1,3,4-nonanetriol (Compound 99)

The compound 77 synthesized in Example 77 was used for the same procedure as in Example 85 to obtain the above-referenced compound.

Example 100

Synthesis of 2-{5-[4-(4-octylbenzoylamino) phenyl] pentanoylamino}-1-O-(2,3,4,6-tetra-O-benzyl-α-D-galactopyranosyl)-D-ribo-1,3,4-nonanetriol (Compound 100)

The compound 78 synthesized in Example 78 was used for the same procedure as in Example 85 to obtain the above-referenced compound.

Example 101

Synthesis of 2-[3-(4-octadecylphenyl) propanoylamino]-1-O-(2,3,4,6-tetra-O-benzyl-α-D-galactopyranosyl)-D-ribo-1,3,4-nonanetriol (Compound 101)

The compound 79 synthesized in Example 79 was used for the same procedure as in Example 85 to obtain the above-referenced compound.

Example 102

Synthesis of 2-(4-nonadecylbenzoylamino)-1-O-(2,3,4,6-tetra-O-benzyl-α-D-galactopyranosyl)-D-ribo-1,3,4-nonanetriol (Compound 102)

The compound 80 synthesized in Example 80 was used for the same procedure as in Example 85 to obtain the above-referenced compound.

Example 103

Synthesis of 2-[5-(4-tetradecyl-1-piperadinyl)pentanoylamino]-1-O-(2,3,4,6-tetra-O-benzyl-α-D-galactopyranosyl)-D-ribo-1,3,4-nonanetriol (Compound 103)

The compound 81 synthesized in Example 81 was used for the same procedure as in Example 85 to obtain the above-referenced compound.

Example 104

Synthesis of 2-[5-(4-hexyloxyphenyl) pentanoylamino]-1-O-(2,3,4,6-tetra-O-benzyl-α-D-galactopyranosyl)-D-ribo-1,3,4-nonanetriol (Compound 104)

The compound 82 synthesized in Example 82 was used for the same procedure as in Example 85 to obtain the above-referenced compound.

Example 105

Synthesis of 2-[5-(4-tetradecyloxyphenyl) pentanoylamino]-1-O-(2,3,4,6-tetra-O-benzyl-α-D-galactopyranosyl)-D-ribo-1,3,4-nonanetriol (Compound 105)

The compound 83 synthesized in Example 83 was used for the same procedure as in Example 85 to obtain the above-referenced compound.

Example 106

Synthesis of 2-{5-(4'-pentyl-[1,1'-biphenyl]-4-yl)pentanoylamino}-1-O-(2,3,4,6-tetra-O-benzyl-α-D-galactopyranosyl)-D-ribo-1,3,4-nonanetriol (Compound 106)

The compound 84 synthesized in Example 84 was used for the same procedure as in Example 85 to obtain the above-referenced compound.

Example 107

Synthesis of 2-tetracosanoylamino-1-O-α-D-galactopyranosyl-D-ribo-1,3,4-nonanetriol (Compound 107)

To a solution of the compound 85 synthesized in Example 85 (70 mg, 0.66 mmol) in a methanol (3 ml)/chloroform (1 ml), palladium hydroxide (25 mg) was added under a stream of nitrogen. The mixture was stirred at room temperature for 3 hours to hydrogenate it. The catalyst was filtered off, and the filtrate was concentrated in vacuo to quantitatively obtain the above-referenced compound (46 mg).

Example 108

Synthesis of 2-tricosanoylamino-1-O-α-D-galactopyranosyl-D-ribo-1,3,4-nonanetriol (Compound 108)

The compound 86 synthesized in Example 86 was used for the same procedure as in Example 107 to obtain the above-referenced compound.

Example 109

Synthesis of 2-docasanoylamino-1-O-α-D-galactopyranosyl-D-ribo-1,3,4-nonanetriol (Compound 109)

The compound 87 synthesized in Example 87 was used for the same procedure as in Example 107 to obtain the above-referenced compound.

Example 110

Synthesis of 2-tricosanoylamino-1-O-α-D-galactopyranosyl-D-ribo-1,3,4-octanetriol (Compound 110)

The compound 88 synthesized in Example 88 was used for the same procedure as in Example 107 to obtain the above-referenced compound.

Example 111

Synthesis of 2-docasanoylamino-1-O-α-D-galactopyranosyl-D-ribo-1,3,4-heptanetriol (Compound 111)

The compound 89 synthesized in Example 89 was used for the same procedure as in Example 107 to obtain the above-referenced compound.

Example 112

Synthesis of 2-tricosanoylamino-1-O-α-D-galactopyranosyl-D-ribo-1,3,4-hexanetriol (Compound 112)

The compound 90 synthesized in Example 90 was used for the same procedure as in Example 107 to obtain the above-referenced compound.

Example 113

Synthesis of 2-docasanoylamino-1-O-α-D-galactopyranosyl-D-ribo-1,3,4-decanetriol (Compound 113)

The compound 91 synthesized in Example 91 was used for the same procedure as in Example 107 to obtain the above-referenced compound.

Example 114

Synthesis of 2-tricosanoylamino-1-O-α-D-galactopyranosyl-D-ribo-1,3,4-decanetriol (Compound 114)

The compound 92 synthesized in Example 92 was used for the same procedure as in Example 107 to obtain the above-referenced compound.

Example 115

Synthesis of 6-phenyl-2-tetracosanoylamino-1-O-α-D-galactopyranosyl-D-ribo-1,3,4-hexanetriol (Compound 115)

The compound 93 synthesized in Example 93 was used for the same procedure as in Example 107 to obtain the above-referenced compound.

Example 116

Synthesis of 5-cyclopentyl-2-tetracosanoylamino-1-O-α-D-galactopyranosyl-D-ribo-1,3,4-pentanetriol (Compound 116)

The compound 94 synthesized in Example 94 was used for the same procedure as in Example 107 to obtain the above-referenced compound.

Example 117

Synthesis of 5-(4-methylphenyl)-2-tetracosanoylamino-1-O-α-D-galactopyranosyl-D-ribo-1,3,4-pentanetriol (Compound 117)

The compound 95 synthesized in Example 95 was used for the same procedure as in Example 107 to obtain the above-referenced compound.

Example 118

Synthesis of 2-(3-phenylpropanoylamino)-1-O-α-D-galactopyranosyl-D-ribo-1,3,4-nonanetriol (Compound 118)

The compound 96 synthesized in Example 96 was used for the same procedure as in Example 107 to obtain the above-referenced compound.

Example 119

Synthesis of 2-(5-phenylpentanoylamino)-1-O-α-D-galactopyranosyl-D-ribo-1,3,4-nonanetriol (Compound 119)

The compound 97 synthesized in Example 97 was used for the same procedure as in Example 107 to obtain the above-referenced compound.

Example 120

Synthesis of 2-[3-(4-octyloxyphenyl) propanoylamino]-1-O-α-D-galactopyranosyl-D-ribo-1,3,4-nonanetriol (Compound 120)

The compound 98 synthesized in Example 98 was used for the same procedure as in Example 107 to obtain the above-referenced compound.

Example 121

Synthesis of 2-[3-(4-hexadecanyloxyphenyl) propanoylamino]-1-O-α-D-galactopyranosyl-D-ribo-1,3,4-nonanetriol (Compound 121)

The compound 99 synthesized in Example 99 was used for the same procedure as in Example 107 to obtain the above-referenced compound.

Example 122

Synthesis of 2-{5-[4-(4-octylbenzoylamino) phenyl] pentanoylamino}-1-O-α-D-galactopyranosyl-D-ribo-1,3,4-nonanetriol (Compound 122)

The compound 100 synthesized in Example 100 was used for the same procedure as in Example 107 to obtain the above-referenced compound.

Example 123

Synthesis of 2-[3-(4-octadecylphenyl) propanoylamino]-1-O-α-D-galactopyranosyl-D-ribo-1,3,4-nonanetriol (Compound 123)

The compound 101 synthesized in Example 101 was used for the same procedure as in Example 107 to obtain the above-referenced compound.

Example 124

Synthesis of 2-(4-nonadecylbenzoylamino)-1-O-α-D-galactopyranosyl-D-ribo-1,3,4-nonanetriol (Compound 124)

The compound 102 synthesized in Example 102 was used for the same procedure as in Example 107 to obtain the above-referenced compound.

Example 125

Synthesis of 2-[5-(4-tetradecyl-1-piperadinyl)pentanoylamino]-1-O-α-D-galactopyranosyl-D-ribo-1,3,4-nonanetriol (Compound 125)

The compound 103 synthesized in Example 103 was used for the same procedure as in Example 107 to obtain the above-referenced compound.

Example 126

Synthesis of 2-[3-(4-hexyloxyphenyl) pentanoylamino]-1-O-α-D-galactopyranosyl-D-ribo-1,3,4-nonanetriol (Compound 126)

The compound 104 synthesized in Example 104 was used for the same procedure as in Example 107 to obtain the above-referenced compound.

Example 127

Synthesis of 2-[3-(4-tetradecyloxyphenyl) pentanoylamino]-1-O-α-D-galactopyranosyl-D-ribo-1,3,4-nonanetriol (Compound 127)

The compound 105 synthesized in Example 105 was used for the same procedure as in Example 107 to obtain the above-referenced compound.

Example 128

Synthesis of 2-{5-(4'-pentyl-[1,1'-biphenyl]-4-yl) pentanoylamino}-1-O-α-D-galactopyranosyl-D-ribo-1,3,4-nonanetriol (Compound 128)

The compound 106 synthesized in Example 106 was used for the same procedure as in Example 107 to obtain the above-referenced compound.

Example 129

Synthesis of 2-tetracosanoylamino-1-O-α-D-galactopyranosyl-D-ribo-1,3,4-nonanetriol 1-hydrate (Compound 129)

The compound 107 synthesized in Example 107 was recrystallized by ethanol-water (10:1) to obtain the above-referenced compound.

mp: 142-145° C. (EtOH—$H_2O$). $[\alpha]_D^{30}$: +53.9 (c=0.5, py). Anal. Calcd. For $C_{39}H_{79}NO_{10}$: C, 64.87; H, 11.03; N, 1.94. Found: C, 64.71; H, 10.88; N, 1.94.

The physicochemical data obtained in the above Reference Example and Examples are shown in Table I.

TABLE I

| Comp. no. | Chemical structure | Rf value | MS | ¹H-NMR (CDCl₃) |
|---|---|---|---|---|
| 1 | [structure with OH, OH, OTs, Ph] | 0.37 (CH₂Cl₂:MeOH = 20:1) | 395 (M + H) (ESI) | 7.80 (d, 2H, J=8.2 Hz), 7.40–7.36 (m, 5H), 7.30 (d, 2H, J=8.2 Hz), 5.50 Cs, 1H), 4.31–4.21 (m, 3H), 4.15–4.07 (m, 2H), 3.90–3.83 (m, 2H), 2.75–2.67 (m, 2H), 2.41 (s, 3H) |
| 2 | [structure with epoxide, Ph] | 0.28 (Hex:AcOEt = 1:2) | 223 (M + H) (ESI) | 7.52–7.49 (m, 2H), 7.41–7.37 (m, 3H), 5.57 (s, 1H), 4.26 (dd, 1H, J=12, 1.5 Hz), 4.09 (dd, 1H, J=12, 1.5 Hz), 3.79–3.76 (m, 2H), 3.35–3.32 (m, 1H), 2.93–2.85 (m, 3H) |
| 3 | [structure with OH, C₅H₁₁, Ph] | 0.37 (Hex:AcOEt = 1:1) | 281 (M + H) (FAB) | 7.52–7.50 (m, 2H), 7.42–7.38 (m, 3H), 5.60 (s, 1H), 4.28 (dd, 1H, J=12, 1.8 Hz), 4.05 (dd, 1H, J=12, 1.3 Hz), 3.95–3.88 (m, 2H), 3.71 (dd, 1H, J=6.6, 1.3 Hz), 3.25 (d, 1H, J=8.7Hz), 2.34 (d, 1H, J=4.5 Hz), 1.73–1.53 (m, 2H), 1.40–1.30 (m, 6H), 0.90 (t, 3H, J=6.7 Hz) |
| 4 | [structure with OH, C₄H₉, Ph] | 0.43 (CH₂Cl₂:MeOH = 20:1) | 289 (M + Na) (FAB) | 7.51–7.48 (m, 2H), 7.40–7.35 (m, 3H), 5.58 (s, 1H), 4.26 (dd, 1H, J=12, 1.8 Hz), 4.04 (dd, 1H, J=12, 1.0 Hz), 3.94–3.87 (m, 2H), 3.70 (m, 1H), 3.23 (d, 1H, J=8.7 Hz), 2.31 Cd, 1H, J=4.5 Hz), 1.71–1.68 (m, 1H), 1.59–1.54 (m, 2H), 1.36–1.35 (m, 3H), 0.91 (t, 3H, J=7.1 Hz) |
| 5 | [structure with OH, C₃H₇, Ph] | 0.13 (Hex:AcOEt = 1:1) | 275 (M + Na) (ESI) | 7.51–7.48 (m, 2H), 7.40–7.35 (m, 3H), 5.58 (s, 1H), 4.26 (dd, 1H, J=12, 1.9 Hz), 4.03 (dd, 1H, J=12, 1.3 Hz), 3.95–3.86 (m, 2H), 3.68 (dd, 1H, J=6.6, 1.3 Hz), 3.26 (d, 1H, J=8.7 Hz), 2.39 (d, 1H, J=4.6 Hz), 1.70–1.39 (m, 4H), 0.95 (t, 3H, J=7.1 Hz) |
| 6 | [structure with OH, C₂H₅, Ph] | 0.15 (Hex:AcOEt = 1:1) | 239 (M + Na) (ESI) | (DMSO-d6) 7.50–7.30 (m, 5H), 5.83 (s, 1H), 4.63 (d, 1H, J=6.4 Hz), 4.60 (d, 1H, J=6.1 Hz), 4.03 (dd, 1H, J=12, 1.5 Hz), 3.97 (dd, 1H, J=12, 1.2Hz), 3.70–3.65 (m, 1H), 3.64–3.54 (m, 1H), 3.51 (dd, 1H, J=8.1, 1.0 Hz), 1.70–1.58 (m, 1H), 1.37–1.20 (m, 1H), 0.89 (t, 3H, J=7.4 Hz) |
| 7 | [structure with OH, C₆H₁₃, Ph] | 0.26 (Hex:AcOEt = 1:1) | 317 (M + Na) (ESI) | 7.53–7.50 (m, 2H), 7.42–7.37 (m, 3H), 5.59 (s, 1H), 4.28 (dd, 1H, J=12, 1.8 Hz), 4.05 (dd, 1H, J=12, 1.0 Hz), 3.94–3.89 (m, 2H), 3.71 (d, 1H, J=6.6 Hz), 3.25 (d, 1H, J=8.7 Hz), 2.33 (d, 1H, J=4.7 Hz), 1.72–1.31 (m, 10H), 0.89 (t, 3H, J=6.7 Hz) |

TABLE I-continued

| Comp. no. | Chemical structure | Rf value | MS | ¹H-NMR (CDCl₃) |
|---|---|---|---|---|
| 8 | (structure: sugar with OH, OH, OBn, CH₂CH₂Ph substituent) | 0.19 (Hex:AcOEt = 2:1) | 337 (M + Na) (ESI) | 7.49–7.46 (m, 2H), 7.39–7.34 (m, 3H), 7.29–7.15 (m, 5H), 5.55 (s, 1H), 4.26 (dd, 1H, J=12, 1.8 Hz), 4.03 (dd, 1H, J=12, 1.2 Hz), 3.98–3.92 (m, 1H), 3.87 (dd, 1H, J=9.1, 1.3 Hz), 3.70 (dd, 1H, J=6.7, 1.1 Hz), 3.14 (d, 1H, J=9.1 Hz), 2.96–2.88 (m, 1H), 2.75–2.68 (m, 1H), 2.34 (d, 1H, J=4.6 Hz), 2.08–1.99 (m, 1H), 1.92–1.82 (m, 1H) |
| 9 | (structure: sugar with OH, OH, OBn, CH₂-cyclopentyl) | 0.41 (Hex:AcOEt = 1:1) | 315 (M + Na) (ESI) | 7.51–7.48 (m, 2H), 7.40–7.35 (m, 3H), 5.58 (s, 1H), 4.26 (dd, 1H, J=12, 1.9 Hz), 4.03 (dd, 1H, J=12, 1.4 Hz), 4.01–3.95 (m, 1H), 3.89 (dd, 1H, J=8.3, 1.4 Hz), 3.68 (dd, 1H, J=6.3, 1.1 Hz), 3.29 (d, 1H, J=8.4 Hz), 2.31 (d, 1H, J=4.4 Hz), 2.08–2.00 (m, 1H), 1.84–1.81 (m, 2H), 1.65–1.53 (m, 6H), 1.21–1.07 (m, 2H) |
| 10 | (structure: sugar with OH, OH, OBn, CH₂-(4-methylphenyl)) | 0.58 (Hex:AcOEt = 1:1) | 337 (M + Na) (ESI) | 7.53 (dd, 2H, J=7.6, 2.0 Hz), 7.37–7.41 (m, 3H), 7.14 (q, 4H, J=8.0 Hz), 5.58 (s, 1H), 4.26 (dd, 1H, J=12, 1.8 Hz), 4.05 (dd, 1H, J=12, 1.2 Hz), 3.88 (d, 1H, J=8.8 Hz), 3.70 (dd, 1H, J=7.7, 0.9 Hz), 3.08 (dd, 1H, J=14, 3.7 Hz), 2.95 (dd, 1H, J=10 Hz), 2.79–2.72 (m, 1H), 2.33 (s, 3H), 2.11 (d, 1H, J=4.7 Hz) |
| 11 | (structure: sugar with OH, OH, OBn, CH₂-(2-chloropyridin-3-yl)) | 0.25 (Et₂O:AcOEt = 6:1) | 336 (M + H) (FAB+) | 8.28 (dd, 1H, J=4.7, 1.9 Hz), 7.70 (dd, 1H, J=7.6, 1.9 Hz), 7.51–7.48 (m, 2H), 7.42–7.36 (m, 3H), 7.19 (t, 1H, J=6.1 Hz), 5.62 (s, 1H), 4.29 (dd, 1H, J=12, 1.9 Hz), 4.27–4.22 (m, 1H), 4.10 (dd, 1H, J=11, 1.6 Hz), 3.82 (dd, 1H, J=1.4 Hz), 3.90 (dd, 1H, J=11, 1.6 Hz), 3.82 (dd, 1H, J=7.6, 1.4 Hz), 3.32 (dd, 1H, J=14, 3.1 Hz), 2.99 (d, 1H, J=11 Hz), 2.89 (dd, 1H, J=14, 9.1 Hz), 2.41 (d, 1H, J=5 Hz) |
| 12 | (structure: sugar with OMs, OH, OBn, C₅H₁₁) | 0.32 (Hex:AcOEt = 3:2) | 359 (M + H) (FAB) | 7.51–7.48 (m, 2H), 7.42–7.35 (m, 3H), 5.59 (s, 1H), 4.99 (d, 1H, J=1.4 Hz), 4.53 (dd, 1H, J=13, 1.6 Hz), 4.18 (dd, 1H, J=13, 1.1 Hz), 3.84–3.75 (m, 2H), 3.19 (s, 3H), 1.60–1.27 (m, 8H), 0.90 (t, 3H, J=6.8 Hz) |
| 13 | (structure: sugar with OMs, OH, OBn, C₄H₉) | 0.39 (Hex:AcOEt = 1:1) | 367 (M + Na) (FAB) | 7.47–7.47 (m, 2H), 7.40–7.34 (m, 3H), 5.58 (s, 1H), 4.98 (d, 1H, J=1.4 Hz), 4.51 (dd, 1H, J=13, 1.7 Hz), 4.15 (dd, 1H, J=13, 1.0 Hz), 3.81–3.73 (m, 2H), 3.17 (s, 3H), 2.77 (d, 1H, J=5.1 Hz), 1.88–1.82 (m, 1H), 1.56–1.31 (m, 5H), 0.91 (t, 3H, J=7.2 Hz) |

TABLE I-continued

| Comp. no. | Chemical structure | Rf value | MS | ¹H-NMR (CDCl₃) |
|---|---|---|---|---|
| 14 | (structure: OMs, OH, C₃H₇, O, Ph) | 0.32 (Hex:AcOEt = 1:1) | 331 (M + H) (ESI) | 7.49–7.47 (m, 2H), 7.39–7.35 (m, 3H), 5.57 (s, 1H), 4.97 (d, 1H, J=1.4 Hz), 4.51 (dd, 1H, J=13, 1.6 Hz), 4.15 (dd, 1H, J=13, 1.2 Hz), 3.81–3.73 (m, 2H), 3.17 (s, 3H), 2.77 (d, 1H, J=5.0 Hz), 1.82–1.39 (m, 4H), 0.94 (t, 3H, J=7.1 Hz) |
| 15 | (structure: OMs, OH, C₂H₅, O, Ph) | 0.47 (CH₂Cl₂:Et₂O = 1:3) | 317 (M + H) (FAB) | 7.53–7.32 (m, 5H), 5.60 (s, 1H), 5.00 (d, 1H), 4.53 (dd, 1H, J=13, 1.5 Hz), 4.18 (dd, 1H, J=13, 1.1 Hz), 3.81–3.70 (m, 2H), 3.20 (s, 3H), 2.81 (d, 1H, J=4.6 Hz), 1.98–1.82 (m, 1H), 1.65–1.40 (m, 1H), 1.04 (t, 3H, J=7.4 Hz) |
| 16 | (structure: OMs, OH, C₆H₁₃, O, Ph) | 0.59 (Hex:AcOEt = 1:1) | 373 (M + H) (ESI) | 7.49–7.47(m, 2H), 7.39–7.35 (m, 3H), 5.58 (s, 1H), 4.97 (d, 1H, J=1.4 Hz), 4.51 (dd, 1H, J=13, 1.6 Hz), 4.15 (dd, 1H, J=13, 1.2 Hz), 3.80–3.73 (m, 2H), 3.17 (s, 3H), 2.77 (d, 1H, J=5.1 Hz), 1.83–1.23 (m, 10H), 0.87 (t, 3H, J=6.6 Hz) |
| 17 | (structure: OMs, OH, CH₂CH₂Ph, O, Ph) | 0.33 (Hex:AcOEt = 1:1) | 415 (M + Na) (ESI) | 7.47–7.44 (m, 2H), 7.39–7.34 (m, 3H), 7.29–7.15 (m, 5H), 5.54 (s, 1H), 4.98 (d, 1H, J=1.2 Hz), 4.49 (dd, 1H, J=13, 1.5 Hz), 4.15 (dd, 1H, J=13, 1.2 Hz), 3.86–3.81 (m, 1H), 3.77 (dd, 1H, J=9.0, 1.0 Hz), 3.15 (s, 3H), 2.97–2.89 (m, 2H), 2.74–2.66 (m, 1H), 2.18–2.16 (m, 1H), 2.03–1.74 (m, 1H) |
| 18 | (structure: OMs, OH, cyclopentyl side chain, O, Ph) | 0.56 (Hex:AcOEt = 1:1) | 393 (M + Na) (ESI) | 7.49–7.46 (m, 2H), 7.39–7.35 (m, 3H), 5.57 (s, 1H), 4.98 (d, 1H, J=1.3 Hz), 4.51 (dd, 1H, J=13, 1.6 Hz), 4.15 (dd, 1H, J=13, 1.2 Hz), 3.86–3.80 (m, 1H), 3.72 (dd, 1H, J=7.4, 1.3 Hz), 3.18 (s, 3H), 2.73 (d, 1H, J=5.5 Hz), 2.08–2.03 (m, 1H), 1.83–1.75 (m, 2H), 1.61–1.51 (m, 6H), 1.19–1.03 (m, 2H) |
| 19 | (structure: OMs, OH, CH₂-p-tolyl, O, Ph) | 0.33 (Hex:AcOEt = 1:1) | 415 (M + Na) (ESI) | 7.53 (dd, 2H, J=7.7, 1.9 Hz), 7.49–7.43 (m, 3H), 7.16 (d, 2H, J=8.2 Hz), 7.13 (d, 2H, J=8.1 Hz), 5.59 (s, 1H), 4.91 (d, 1H, J=1.3 Hz), 4.53 (dd, 1H, J=13, 1.4 Hz), 4.12 (dd, 1H, J=13, 0.8 Hz), 4.01–4.06 (m, 1H), 3.77 (dd, 1H, J=9.1, 0.8 Hz), 3.14 (s, 3H), 2.78–2.72 (m, 1H), 2.55 (d, 1H, J=7.2 Hz), 2.33 (s, 3H). |

TABLE I-continued

| Comp. no. | Chemical structure | Rf value | MS | ¹H-NMR (CDCl₃) |
|---|---|---|---|---|
| 20 | (OMs, OH, C5H11 substituents on pyranose with 2-chloropyridin-3-ylmethyl; Ph on ring O) | 0.55 (Hex:AcOEt:MeOH = 5:5:1) | 414 (M + H) (FAB+) | 8.28 (dd, 1H, J=4.6, 1.8 Hz), 7.71 (dd, 1H, J=7.5, 1.8 Hz), 7.53–7.50 (m, 2H), 7.42–7.37 (m, 3H), 7.19 (t, 1H, J=6.1 Hz), 5.65 (s, 1H), 5.00 (s, 1H), 4.52 (dd, 1H, J=13, 1.5 Hz), 4.19 (d, 1H, J=13 Hz), 4.17–4.11 (m, 1H), 3.88 (d, 1H, J=9.0 Hz), 3.42 (dd, 1H, J=14, 2.7 Hz), 3.18 (s, 3H), 3.07 (d, 1H, J=5.4 Hz), 2.83 (dd, 1H, J=14, 8.8 Hz) |
| 21 | (N₃, OH, C4H9; Ph) | 0.41 (Hex:AcOEt = 4:1) | 305 (M + Na) (ESI) | 7.47–7.37 (m, 5H), 5.49 (s, 1H), 4.43–4.40 (m, 1H), 3.93–3.88 (m, 1H), 3.75–3.67 (m, 3H), 2.09 (d, 1H, J=6.2 Hz), 1.67–1.59 (m, 2H), 1.43–1.34 (m, 6H), 0.91 (t, 3H, J=6.8 Hz) |
| 22 | (N₃, OH, C4H9; Ph) | 0.44 (Hex:AcOEt = 4:1) | 264 (M−N₂+H) (ESI) | 7.46–7.43 (m, 2H), 7.38–7.36 (m, 3H), 5.47(s, 1H), 4.41–4.38 (m, 1H), 3.92–3.86 (m, 1H), 3.74–3.65 (m, 3H), 2.05 (d, 1H, J=6.2 Hz), 1.65–1.61 (m, 2H), 1.58–1.34 (m, 4H), 0.92 (t, 3H, J=7.1 Hz) |
| 23 | (N₃, OH, C3H7; Ph) | 0.46 (Hex:AcOEt = 4:1) | 250 (M−N₂+H) (ESI) | 7.39–7.44 (m, 2H), 7.39–7.35 (m, 3H), 5.46(s, 1H), 4.41–4.38 (m, 1H), 3.91–3.89 (m, 1H), 3.73–3.64 (m, 3H), 2.12 (d, 1H, J=6.3Nz), 1.65–1.42 (m, 4H), 0.97 (t, 3H, J=6.9 Hz) |
| 24 | (N₃, OH, C2H5; Ph) | 0.22 (Hex:AcOEt = 4:1) | 264 (M + H) (FAB) | 7.50–7.32 (m, 5H), 5.49(s, 1H), 4.47–4.38 (m, 1H), 3.88–3.79 (m, 1H), 3.76–3.62 (m, 3H), 2.09 (m, 1H, J=6.1 Hz), 1.80–1.60 (m, 1H), 1.07 (t, 3H, J=7.4 Hz) |
| 25 | (N₃, OH, C6H13; Ph) | 0.39 (Hex:AcOEt = 4:1) | 292 (M−N₂+H) (ESI) | 7.46–7.36 (m, 5H), 5.47 (s, 1H), 4.40–4.37 (m, 1H), 3.89–3.87 (m, 1H), 3.74–3.65 (m, 3H), 2.08 (d, 1H, J=6.2 Hz), 1.64–1.30 (m, 10H), 0.88 (t, 3H, J=6.8 Hz) |
| 26 | (N₃, OH, CH₂CH₂Ph; Ph) | 0.39 (Hex:AcOEt = 1:1) | 312 (M−N₂+H) (ESI) | 7.45–7.42 (m, 2H), 7.38–7.36 (m, 3H), 7.31–7.17 (m, 5H), 5.45 (s, 1H), 4.40–4.37 (m, 1H), 3.92–3.89 (m, 1H), 3.73–3.63 (m, 3H), 2.94–2.91 (m, 1H), 2.75–2.71 (m, 1H), 2.20 (d, 1H, J=6.2 Hz), 1.99–1.93 (m, 2H) |

TABLE I-continued

| Comp. no. | Chemical structure | Rf value | MS | $^1$H-NMR (CDCl$_3$) |
|---|---|---|---|---|
| 27 | Ph–O–tetrahydropyran with N$_3$, OH, cyclopentylmethyl substituents | 0.58 (Hex:AcOEt = 3:1) | 290 (M−N$_2$+H) (ESI) | 7.46–7.43 (m, 2H), 7.40–7.36 (m, 3H), 5.47 (s, 1H), 4.39 (dd, 1H, J=9.5, 3.5 Hz), 3.98–3.92 (m, 1H), 3.73–3.66 (m, 3H), 2.10–2.00 (m, 1H), 2.02 (d, 1H, J=6.5 Hz), 1.90–1.72 (m, 3H), 1.67–1.49 (m, 5H), 1.21–1.05 (m, 2H) |
| 28 | Ph–O–tetrahydropyran with N$_3$, OH, 4-methylbenzyl substituents | 0.47 (Hex:AcOEt = 1:1) | 312 (M−N$_2$+H) (ESI) | 7.49–7.40 (m, 2H), 7.39–7.37 (m, 3H), 7.18 (d, 2H, J=8.0 Hz), 7.14 (d, 2H, J=8.0 Hz), 5.48 (s, 1H), 4.40 (dd, 1H, J=10.4.5 Hz), 4.16–4.13 (m, 1H), 3.77–3.66 (m, 2H), 3.04 (dd, 1H, J=14, 4.4 Hz), 2.90–2.85 (m, 1H), 2.34 (s, 3H), 2.09 (d, 1H, J=7.2 Hz). |
| 29 | Ph–O–tetrahydropyran with N$_3$, OH, (2-chloropyridin-3-yl)methyl substituents | 0.85 (CHCl$_3$:MeOH = 10:1) | 361 (M+H) (FAB+) | 8.27 (dd, 1H, J=4.8, 1.9 Hz), 7.69 (dd, 1H, J=7.5, 1.9 Hz), 7.50–7.44 (m, 2H), 7.42–7.36 (m, 3H), 7.19 (t, 1H, J=6.2 Hz), 5.52 (s, 1H), 4.48–4.44 (m, 1H), 4.24–4.27 (m, 1H), 3.87–3.73 (m, 3H), 3.24 (dd, 1H, J=14, 2.9 Hz), 2.91 (dd, 1H, J=14, 10 Hz), 2.36–2.38 (m, 1H) |
| 30 | Open-chain polyol: HO–CH$_2$–CH(N$_3$)–CH(OH)–CH(OH)–C$_5$H$_{11}$ | 0.35 (Hex:AcOEt = 1:1) | 218 (M+H) (FAB) | 4.05–3.98 (m, 1H), 3.91–3.74 (m, 3H), 2.67 (brs 1H), 2.52 (d, 1H, J=4.4 Hz), 2.20 (brs, 1H), 1.61–1.52 (m, 2H), 1.40–1.31 (m, 6H), 0.91 (t, 3H, J=6.6 Hz) |
| 31 | Open-chain polyol: HO–CH$_2$–CH(N$_3$)–CH(OH)–CH(OH)–C$_4$H$_9$ | 0.21 (CH$_2$Cl$_2$:MeOH = 20:1) | 176 (M+H) (FAB) | 4.01–3.98 (m, 1H), 3.89–3.74 (m, 3H), 3.69–3.65 (m, 1H), 2.64 (brs, 1H), 2.49 (d, 1H, J=4.5 Hz), 2.18–2.17 (brs, 1H), 1.62–1.51 (m, 3H), 1.48–1.33 (m, 3H), 0.92 (t, 3H, J=7.1 Hz) |
| 32 | Open-chain polyol: HO–CH$_2$–CH(N$_3$)–CH(OH)–CH(OH)–C$_3$H$_7$ | 0.19 (CH$_2$Cl$_2$:MeOH = 15:1) | 162 (M−N$_2$+H) (ES) | 4.01–3.96 (m, 1H), 3.89–3.73 (m, 3H), 3.67–3.63 (m, 1H), 2.85–2.70 (m, 2H), 2.38 (brs, 1H), 1.59–1.34 (m, 4H), 0.96 (t, 3H, J=7.0 Hz) |

TABLE I-continued

| Comp. no. | Chemical structure | Rf value | MS | ¹H-NMR (CDCl₃) |
|---|---|---|---|---|
| 33 | (structure: N₃, OH, OH, C₂H₅, HO-CH₂ backbone) | 0.19 (Hex:AcOEt = 1:1) | 176 (M + H) (FAB) | 4.05–3.95 (m, 1H), 3.94–3.82 (m, 1H), 3.80–3.61 (m, 3H), 2.67–2.53 (m, 1H), 2.48 (d, 1H, J=4.6 Hz), 2.22–2.10 (m, 1H), 1.75–1.39 (m, 2H), 1.02 (t, 3H, J=7.4 Hz) |
| 34 | (structure with C₆H₁₃) | 0.14 (Hex:AcOEt = 2:1) | 254 (M + Na) (ESI) | 4.05–3.95 (m, 1H), 3.91–3.63 (m, 4H), 2.67 (brs 1H), 2.52 (brd, 1H, J=4.3 Hz), 2.20 (brs, 1H), 1.62–1.25 (m, 10H), 0.90 (t, 3H, J=6.8 Hz) |
| 35 | (structure with CH₂CH₂Ph) | 0.14 (Hex:AcOEt = 1:1) | 224 (M—N₂ + H) (ESI) | 7.30–7.16 (m, 5H), 3.96–3.91 (m, 1H), 3.86–3.72 (m, 3H), 3.62–3.57 (m, 1H), 3.17 (brs 1H), 3.08 (d, 1H, J=4.6 Hz), 2.90–2.77 (m, 2H), 2.72–2.66 (m, 1H), 1.93–1.81 (m, 2H) |
| 36 | (structure with CH₂-cyclopentyl) | 0.25 (CH₂Cl₂:MeOH = 20:1) | 252 (M + Na) (ESI) | 4.04–3.97 (m, 1H), 3.89–3.85 (m, 2H), 3.75 (m, 1H), 3.66 (m, 1H), 2.66 (m, 1H), 2.49 (d, 1H, J=4.6 Hz), 2.17 (d, 1H, J=4.2 Hz), 2.04–1.91 (m, 1H), 1.84–1.80 (m, 2H), 1.67–1.49 (m, 6H), 1.21–1.05 (m, 2H) |
| 37 | (structure with CH₂-p-tolyl) | 0.10 (Hex:AcOEt = 1:1) | 224 (M—N₂ + H) (ESI) | 7.17–7.12 (m, 4H), 4.04–3.93 (m, 2H), 3.84–3.81 (m, 1H), 3.75 (q, 1H, J=4.9 Hz), 3.03 (dd, 1H, J=13, 3.3 Hz), 2.71 (dd, 1H, J=13, 9.6 Hz), 2.34 (s, 3H). |
| 38 | (structure with CH₂-(2-chloropyridin-3-yl)) | 0.20 (CHCl₃:MeOH = 10:1) | 273 (M + H) (FAB+) | 8.31 (dd, 1H, J=4.7, 1.7 Hz), 7.68 (dd, 1H, J=9.3, 1.8 Hz), 7.25–7.21 (m, 1H), 4.21–4.06 (m, 2H), 3.99–3.93 (m, 1H), 3.92–3.81 (m, 1H), 3.80–3.75 (m, 1H), 3.24 (dd, 1H, J=14, 2.8 Hz), 2.84 (dd, 1H, J=14, 10.0 Hz), 2.70–2.60 (m, 1H), 2.40–2.30 (1H, m), 2.67–2.25 (1H, m) |

TABLE I-continued

| Comp. no. | Chemical structure | Rf value | MS | ¹H-NMR (CDCl₃) |
|---|---|---|---|---|
| 39 | (structure: OMs, OH, OH, HO, C-chain) | 0.11 (Hex:AcOEt = 1:1) | 293 (M + Na) (ESI) | 5.03–5.00 (m, 1H), 4.02–4.00 (m, 2H), 3.62–3.60 (m, 2H), 3.19 (s, 3H), 1.76–1.72 (m, 1H), 1.56–1.28 (m, 7H), 0.90 (t, 3H, J=6.7 Hz) |
| 40 | (structure: C₅H₁₁, dioxolane, N₃, HO) | 0.21 (Hex:AcOEt = 5:1) | 280 (M + Na) (ESI) | 4.21–4.16 (m, 1H), 4.02–3.95 (m, 2H), 3.90–3.84 (m, 1H), 3.50–3.45 (m, 1H), 2.11 (t, 1H, J=5.6 Hz), 1.63–1.54 (m, 2H), 1.43 (s, 3H), 1.40–1.34 (m, 9H), 0.91 (t, 3H, J=6.9 Hz) |
| 41 | (structure: C₄H₉, dioxolane, N₃, HO) | 0.38 (Hex:AcOEt = 3:1) | 216 (M—N₂ + H) (ESI) | 4.20–4.15 (m, 1H), 4.01–3.94 (m, 2H), 3.89–3.83 (m, 1H), 3.49–3.44 (m, 1H), 2.06 (dd, 1H, J=6.8, 5.7 Hz), 1.63–1.54 (m, 2H), 1.42 (s, 3H), 1.42–1.33 (m, 4H), 1.33 (s, 3H), 0.92 (t, 3H, J=7.1 Hz) |
| 42 | (structure: C₃H₇, dioxolane, N₃, HO) | 0.21 (Hex:AcOEt = 4:1) | 202 (M—N₂ + H) (ESI) | 4.21–4.15 (m, 1H), 4.01–3.92 (m, 2H), 3.88–3.81 (m, 1H), 3.48–3.42 (m, 1H), 2.23 (t, 1H, J=6.2 Hz), 1.60–1.35 (m, 7H), 1.32 (s, 3H), 0.97(t, 3H, J=7.1 Hz) |
| 43 | (structure: C₂H₅, dioxolane, N₃, HO) | 0.25 (Hex:AcOEt = 4:1) | 216 (M + H) (FAB) | 4.16–4.08 (m, 1H), 4.04–3.95 (m, 2H), 3.92–3.84 (m, 1H), 3.51–3.44 (m, 1H), 2.10 (t, 1H, J=6.2 Hz), 1.76–1.50 (m, 2H), 1.44 (s, 3H), 1.35 (S, 3M), 1.08 (t, 3H, J=7.4 Hz) |

TABLE I-continued

| Comp. no. | Chemical structure | Rf value | MS | ¹H-NMR (CDCl₃) |
|---|---|---|---|---|
| 44 | (structure with C₆H₁₃) | 0.26 (Hex:AcOEt = 5:1) | 244 (M−N₂+H) (ESI) | 4.21–4.16 (m, 1H), 4.02–3.94 (m, 2H), 3.91–3.84 (m, 1H), 3.51–3.45 (m, 1H), 2.10 (t, 1H, J=6.2 Hz), 1.65–1.25 (m, 16H), 0.90 (t, 3H, J=6.8 Hz) |
| 45 | (structure with CH₂CH₂Ph) | 0.34 (Hex:AcOEt = 4:1) | 264 (M−N₂+H) (ESI) | 7.31–7.17 (m, 5H), 4.19–4.14 (m, 1H), 4.02–3.94 (m, 2H), 3.89–3.83 (m, 1H), 3.48–3.43 (m, 1H), 2.92–2.88 (m, 1H), 2.74–2.68 (m, 1H), 2.16–2.13 (m, 1H), 1.94–1.85 (m, 2H), 1.46 (s, 3H), 1.34 (s, 3H) |
| 46 | (structure with cyclopentylmethyl) | 0.65 (CH₂Cl₂:MeOH = 20:1) | 242 (M−N₂+H) (ESI) | 4.26–4.21 (m, 1H), 4.01–3.94 (m, 2H), 3.89–3.83 (m, 1H), 3.48–3.43 (m, 1H), 2.06–1.97 (m, 2H), 1.84–1.82 (m, 2H), 1.72–1.47 (m, 6H), 1.42 (s, 3H), 1.33 (s, 3H), 1.21–1.08 (m, 2H) |
| 47 | (structure with p-tolylmethyl) | 0.23 (Hex:AcOEt = 4:1) | 264 (M−N₂+H) (ESI) | 7.17 (d, 2H, J=8.0 Hz), 7.14 (d, 2H, J=8.0 Hz), 4.46–4.41 (m, 1H), 4.08–4.03 (m, 1H), 3.95–3.89 (m, 1H), 3.63–3.60 (m, 1H), 2.97 (dd, 1H, J=14,3.0 Hz), 2.78 (dd, 1H, J=14, 10 Hz), 2.33 (s, 3H), 2.11 (dd, 1H, J=6.7, 5.4 Hz), 1.49 (s, 3H), 1.30 (s, 3H) |

TABLE I-continued

| Comp. no. | Chemical structure | Rf value | MS | ¹H-NMR (CDCl₃) |
|---|---|---|---|---|
| 48 | (structure with C₅H₁₁, N₃, OBn, BnO, OBn, OBn) | 0.43 (Hex:AcOEt = 3:1) | 803 (M + Na) (ESI) | 7.40–7.26 (m, 20 H), 4.97–4.93 (m, 2H), 4.87–4.79 (m, 2H), 4.74–4.70 (m, 2H), 4.57 (d, 1H, J=12 Hz), 4.49 (d, 1H, J=12 Hz), 4.41 (d, 1H, J=12 Hz), 4.10–3.94 (m, 7H), 3.75–3.70 (m, 1H), 3.56–3.44 (m, 3H), 1.62–1.49 (m, 2H), 1.40–1.26 (m, 12H), 0.91 (t, 3H, J=6.6 Hz) |
| 49 | (structure with C₄H₉, N₃, OBn, BnO, OBn, OBn) | 0.42 (Hex:AcOEt = 4:1) | 738 (M – N₂ + H) (FAB) | 7.38–7.25 (m, 20 H), 4.94–4.91 (m, 2H), 4.83 (d, 1H, J=12 Hz), 4.78 (d, 1H, J=12 Hz), 4.72–4.69 (m, 2H), 4.55 (d, 1H, J=12 Hz), 4.47 (d, 1H, J=12 Hz), 4.39 (d, 1H, J=12 Hz), 4.11–3.92 (m, 7H), 3.72–3.68 (m, 1H), 3.50–3.43 (m, 3H), 1.61–1.49 (m, 2H), 1.41–1.26 (m, 4H), 1.36 (s, 3H), 1.26 (s, 3H), 0.91 (t, 3H, J=7.1 Hz) |
| 50 | (structure with C₃H₇, N₃, OBn, BnO, OBn, OBn) | 0.43 (Hex:AcOEt = 4:1) | 774 (M + Na) (ESI) | 7.38–7.22 (m, 20 H), 4.94–4.92 (m, 2H), 4.83 (d, 1H, J=12 Hz), 4.78 (d, 1H, J=12 Hz), 4.72–4.68 (m, 2H), 4.55 (d, 1H, J=12 Hz), 4.47 (d, 1H, J=12 Hz), 4.39 (d, 1H, J=12 Hz), 4.13–3.92 (m, 7H), 3.73–3.68 (m, 1H), 3.53–3.43 (m, 3H), 1.58–1.48 (m, 2H), 1.35 (s, 3H), 1.26 (s, 3H), 0.91 (t, 3H, J=6.9 Hz) |
| 51 | (structure with C₂H₅, N₃, OBn, BnO, OBn, OBn) | 0.30 (Hex:Acetone = 5:1) | 712 (M – N₂ + H) (FAB) | 7.40–7.18 (m, 20 H), 4.96–4.89 (m, 2H), 4.83 (d, 1H, J=12 Hz), 4.78 (d, 1H, J=12 Hz), 4.69 (dd, 2H, J=12, 5.2 Hz), 4.55 (d, 1H, J=12 Hz), 4.46 (d, 1H, J=12 Hz), 4.39 (d, 1H, J=12 Hz), 4.10–3.87 (m, 7H), 3.73–3.68 (m, 1H), 3.60–3.41 (m, 3H), 1.71–1.46 (m, 2H), 1.36 (s, 3H), 1.26 (s, 3H), 1.02 (t, 3H, J=7.3 Hz) |

TABLE I-continued

| Comp. no. | Chemical structure | Rf value | MS | ¹H-NMR (CDCl₃) |
|---|---|---|---|---|
| 52 | 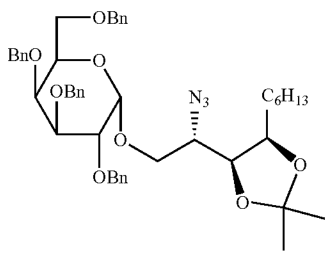 | 0.28 (Hex:Et₂O = 3:1) | 766 (M—N₂+H) (FAB) | 7.40–7.24 (m, 20H), 4.97–4.93 (m, 2H), 4.87–4.78 (m, 2H), 4.74–4.69 (m, 2H), 4.57 (d, 1H, J=12 Hz), 4.49 (d, 1H, J=12 Hz), 4.41 (d, 1H, J=12 Hz), 4.14–3.93 (m, 7H), 3.75–3.70 (m, 1H), 3.52–3.47 (m, 3H), 1.62–1.49 (m, 2H), 1.42–1.26 (m, 14H), 0.90 (t, 3H, J=6.7 Hz) |
| 53 | 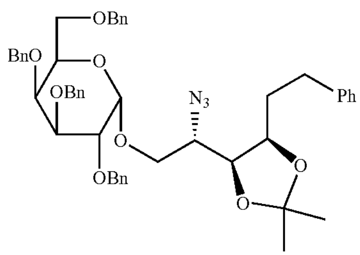 | 0.39 (Hex:AcOEt = 5:1) | 787 (M—N₂+H) (ESI) | 7.38–7.18 (m, 25H), 4.95–4.92 (m, 2H), 4.85–4.77 (m, 2H), 4.72–4.67 (m, 2H), 4.56 (d, 1H, J=12 Hz), 4.46 (d, 1H, J=12 Hz), 4.38 (d, 1H, J=12 Hz), 4.13–3.92 (m, 7H), 3.75–3.70 (m, 1H), 3.53–3.44 (m, 3H), 2.91–2.85 (m, 1H), 2.72–2.66 (m, 1H), 1.94–1.84 (m, 2H), 1.41 (s, 3H), 1.28 (s, 3H) |
| 54 | 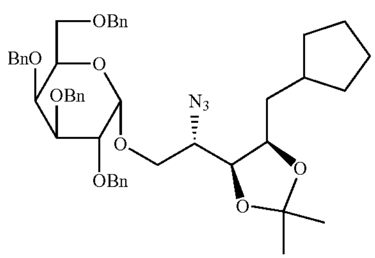 | 0.45 (Hex:AcOEt = 1:1) | 764 (M—N₂+H) (ESI) | 7.38–7.25 (m, 20H), 4.94–4.92 (m, 2H), 4.83 (d, 1H, J=12 Hz), 4.78 (d, 1H, J=12 Hz), 4.70 (d, 1H, J=12 Hz), 4.69 (d, 1H, J=12 Hz), 4.55 (d, 1H, J=12 Hz), 4.47 (d, 1H, J=12 Hz), 4.39 (d, 1H, J=12 Hz), 4.17–4.12 (m, 1H), 4.07–3.92 (m, 6H), 3.70 (dd, 1H, J=11, 6.6 Hz), 3.50–3.44 (m, 3H), 2.01–1.93 (m, 1H), 1.88–1.75 (m, 2H), 1.68–1.46 (m, 6H), 1.36 (s, 3H), 1.26 (s, 3H), 1.18–1.06 (m, 2H) |
| 55 | 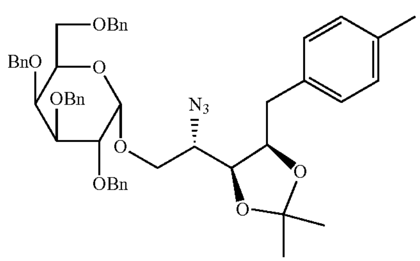 | 0.63 (Hex:AcOEt = 3:1) | 787 (M—N₂+H) (FAB) | 7.51–7.24 (m, 20H), 7.14 (d, 2H, J=8.0 Hz), 7.10 (d, 2H, J=8.0 Hz), 4.96–4.93 (m, 2H), 4.85–4.78 (m, 2H), 4.73–4.69 (m, 2H), 4.56 (d, 1H, J=10 Hz), 4.48 (d, 1H, J=13 Hz), 4.41 (d, 1H, J=13 Hz), 4.38–4.34 (m, 1H), 4.16–3.96 (m, 6H), 3.78–3.74 (m, 1H), 3.63–3.60 (m, 1H), 3.55–3.49 (m, 2H), 2.95 (dd, 1H, J=14, 2.7 Hz), 2.77–2.71 (m, 1H), 2.32 (s, 3H), 1.43 (s, 3H), 1.23 (s, 3H). |

TABLE I-continued

| Comp. no. | Chemical structure | Rf value | MS | ¹H-NMR (CDCl₃) |
|---|---|---|---|---|
| 56 | (structure with C₅H₁₁) | 0.28 (CH₂Cl₂:MeOH = 20:1) | 754 (M + H) (ESI) | 7.40–7.25 (m, 20 H), 4.96-4.92 (m, 2H), 4.84-4.64 (m, 4H), 4.58 (d, 1H, J=11 Hz), 4.50 (d, 1H, J=12 Hz), 4.41 (d, 1H, J=12 Hz), 4.13–3.86 (m, 6H), 3.58–3.51 (m, 2H), 3.42–3.37 (m, 1H), 3.07–3.01 (m, 1H), 1.65–1.20 (m, 14H), 0.90 (t, 3H, J=5.6 Hz) |
| 57 | (structure with C₄H₉) | 0.39 (CH₂Cl₂:MeOH = 20:1) | 740 (M + H) (FAB) | 7.37–7.25 (m, 20H), 4.94-4.91 (m, 2H), 4.82-4.65 (m, 4H), 4.55 (d, 1H, J=11 Hz), 4.46 (d, 1H, J=12 Hz), 4.39 (d, 1H, J=12 Hz), 4.10-4.03 (m, 2H), 3.97–3.90 (m, 3H), 3.87–3.84 (m, 1H), 3.56–3.49 (m, 2H), 3.39–3.35 (m, 3H), 3.07–3.02 (m, 1H), 1.53 (m, 1H), 1.37 (s, 3H), 1.37–1.24 (m, 4H), 1.27 (s, 3H), 0.90 (t, 3H, J=7.1 Hz) |
| 58 | (structure with C₃H₇) | 0.19 (CH₂Cl₂:MeOH = 30:1) | 726 (M + H) (FAB) | 7.38–7.23 (m, 20H), 4.94-4.91 (m, 2H), 4.82-4.65 (m, 4H), 4.56 (d, 1H, J=11 Hz), 4.46 (d, 1H, J=12 Hz), 4.39 (d, 1H, J=12 Hz), 4.14-4.09 (m, 1H), 4.06–4.03 (m, 1H), 3.97–3.90 (m, 4H), 3.87–3.84 (m, 1H), 3.56–3.49 (m, 2H), 3.39–3.35 (m, 1H), 3.06–3.02 (m, 1H), 1.60–1.24 (m, 4H), 1.37 (s, 3H), 1.27 (s, 3H), 0.93 (t, 3H, J=7.2 Hz) |
| 59 | (structure with C₆H₁₃) | 0.32 (CH₂Cl₂:MeOH = 20:1) | 768 (M + H) (FAB) | 7.38–7.23 (m, 20H), 4.94-4.91 (m, 2H), 4.82-4.71 (m, 3H), 4.66 (d, 1H, J=12 Hz), 4.56 (d, 1H, J=11 Hz), 4.47 (d, 1H, J=12 Hz), 4.39 (d, 1H, J=12 Hz), 4.12–4.07 (m, 1H), 4.04 (dd, 1H, J=10, 3.7 Hz), 3.97–3.90 (m, 4H), 3.85 (dd, 1H, J=9.1, 5.6 Hz), 3.56–3.49 (m, 2H), 3.37 (dd, 1H, J=10, 7.5 Hz), 3.06–3.02 (m, 1H), 1.51–1.24 (m, 10H), 1.37 (s, 3H), 1.27 (s, 3H), 0.87 (t, 3H, J=6.7 Hz) |

TABLE I-continued

| Comp. no. | Chemical structure | Rf value | MS | ¹H-NMR (CDCl₃) |
|---|---|---|---|---|
| 60 | 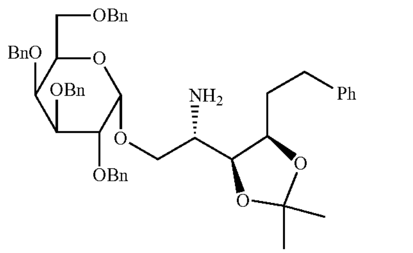 | 0.21 (Hex:AcOEt = 1:1) | 788 (M+) (ESI) | 7.37–7.14 (m, 25H), 4.94-4.90 (m, 2H), 4.81-4.76 (m, 2H), 4.72 (d, 1H, J=12 Hz), 4.66 (d, 1H, J=12 Hz), 4.55 (d, 1H, J=11 Hz), 4.44 (m, 1H), 4.36 (d, 1H, J=12 Hz), 4.15–4.08 (m, 1H), 4.05–4.02 (m, 1H), 3.95–3.84 (m, 5H), 3.54–3.49 (m, 2H), 3.40–3.35 (m, 1H), 3.05–3.00 (m, 1H), 2.92–2.86 (m, 1H), 2.68–2.60 (m, 1H), 1.88–1.79 (m, 2H), 1.43 (s, 3H), 1.29 (s, 3H) |
| 61 | 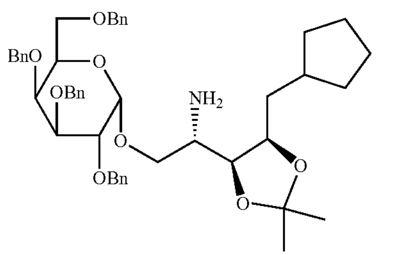 | 0.21 (CH₂Cl₂:MeOH = 20:1) | 766 (M + H) (FAB) | 7.38–7.25 (m, 20H), 4.94-4.91 (m, 2H), 4.82–4.74 (m, 2H), 4.71–4.65 (m, 2H), 4.56 (d, 1H, J=11 Hz), 4.46 (d, 1H, J=12 Hz), 4.39 (d, 1H, J=12 Hz), 4.18–4.13 (m, 1H), 4.04 (dd, 1H, J=10, 3.6 Hz), 3.97–3.90 (m, 4H), 3.85 (dd, 1H, J=9.0, 5.5 Hz), 3.66–3.49 (m, 2H), 3.37 (dd, 1H, J=10, 7.6 Hz), 3.06–3.02 (m, 1H), 2.04–1.93 (m, 1H), 1.87–1.74 (m, 2H), 1.71–1.39 (m, 6H), 1.37 (s, 3H), 1.27 (s, 3H), 1.17–1.00 (m, 2H) |
| 62 | 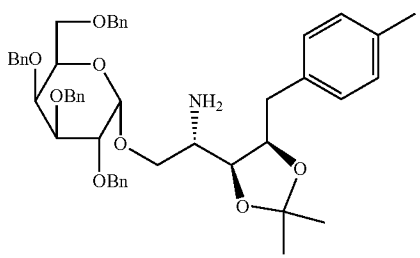 | 0.42 (Hex:AcOEt = 1:1) | 788 (M + H) (ESI) | 7.25–7.39 (m, 20H), 7.14 (d, 2H, J=8.0 Hz), 7.09 (d, 2H, J=8.0 Hz), 4.95–4.92 (m, 2H), 4.80–4.55 (m, 5H), 4.48–4.31 (m, 3H), 4.08–3.94 (m, 6H), 3.74–3.55 (m, 4H), 2.95 (dd, 1H, J=14, 3.4 Hz), 2.74–2.68 (m, 1H), 2.30 (s, 3 H), 1.46 (s, 3H), 1.24 (s, 3H). |
| 63 | 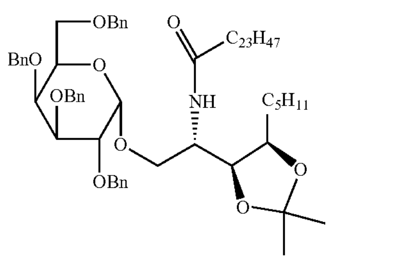 | 0.23 (Hex:AcOEt = 4:1) | 1105 (M + H) (FAB) | 7.41–7.24 (m, 20H), 6.28 (d, 1H, J=8.4 Hz), 4.95–4.90 (m, 2H), 4.83–4.73 (m, 2H), 4.75 (d, 1H, J=12 Hz), 4.66 (d, 1H, J=11 Hz), 4.58 (d, 1H, J=12 Hz), 4.49 (d, 1H, J=12 Hz), 4.38 (d, 1H, J=12 Hz), 4.13–4.03 (m, 4H), 3.98 (t, 1H, J=6.2 Hz), 3.93–3.90 (m, 3H), 3.63–3.53 (m, 2H), 3.40–3.37 (m, 1H), 2.08–1.95 (m, 2H), 1.55–1.25 (m, 50H), 1.40 (s, 3H), 1.32 (s, 3H), 0.90–0.84 (m, 6H) |

| Comp. no. | Chemical structure | Rf value | MS | $^1$H-NMR (CDCl$_3$) |
|---|---|---|---|---|
| 64 | (structure with C$_{22}$H$_{45}$, C$_5$H$_{11}$, OBn groups) | 0.44 (Hex:AcOEt = 4:1) | 1090 (M+) (FAB) | 7.41–7.24 (m, 20H), 6.27 (d, 1H, J=8.2 Hz), 4.95–4.90 (m, 2H), 4.83–4.79 (m, 2H), 4.75 (d, 1H, J=12 Hz), 4.67 (d, 1H, J=12 Hz), 4.59 (d, 1H, J=12 Hz), 4.50 (d, 1H, J=12 Hz), 4.39 (d, 1H, J=12 Hz), 4.13–3.90 (m, 7H), 3.63–3.53 (m, 3H), 3.41–3.36 (m, 1H), 2.10–1.94 (m, 2H), 1.48–1.36 (m, 5H), 1.35–1.05 (m, 49H), 0.94–0.78 (m, 6H) |
| 65 | (structure with C$_{21}$H$_{43}$, C$_5$H$_{11}$, OBn groups) | 0.37 (Hex:AcOEt = 3:1) | 1076 (M+) (FAB) | 7.40–7.23 (m, 20H), 6.27 (d, 1H, J=8.4 Hz), 4.96–4.89 (m, 2H), 4.85–4.78 (m, 2H), 4.75 (d, 1H, J=12 Hz), 4.67 (d, 1H, J=11 Hz), 4.59 (d, 1H, J=12 Hz), 4.49 (d, 1H, J=12 Hz), 4.38 (d, 1H, J=12 Hz), 4.10–3.89 (m, 7H), 3.63–3.52 (m, 3H), 3.39 (dd, 1H, J=9.5, 5.6 Hz), 2.09–1.95 (m, 2H), 1.49–1.41 (m, 5H), 1.32 (s, 3H), 1.31–1.22 (m, 44H), 0.91–0.83 (m, 6H) |
| 66 | (structure with C$_{22}$H$_{45}$, C$_4$H$_9$, OBn groups) | 0.33 (Hex:AcOEt = 3:1) | 1076 (M+) (FAB) | 7.39–7.22 (m, 20H), 6.25 (d, 1H, J=8.4 Hz), 4.93–4.88 (m, 2H), 4.82–4.77 (m, 2H), 4.73 (d, 1H, J=12 Hz), 4.64 (d, 1H, J=11 Hz), 4.56 (d, 1H, J=12 Hz), 4.47 (d, 1H, J=12 Hz), 4.36 (d, 1H, J=12 Hz), 4.10–4.02 (m, 4H), 3.96 (t, 1H, J=6.3 Hz), 3.91–3.88 (m, 3H), 3.61–3.52 (m, 2H), 3.38–3.38 (m, 1H), 2.05–1.97 (m, 2H), 1.53–1.23 (m, 46H), 1.39 (s, 3H), 1.30 (s, 3H), 0.88–0.82 (m, 6H) |
| 67 | (structure with C$_{21}$H$_{43}$, C$_3$H$_7$, OBn groups) | 0.31 (Hex:AcOEt = 3:1) | 1048 (M+) (FAB) | 7.39–7.22 (m, 20H), 6.25 (d, 1H, J=8.5 Hz), 4.93–4.88 (m, 2H), 4.82–4.78 (m, 2H), 4.73 (d, 1H, J=12 Hz), 4.64 (d, 1H, J=11 Hz), 4.57 (d, 1H, J=12 Hz), 4.47 (d, 1H, J=12 Hz), 4.36 (d, 1H, J=12 Hz), 4.12–3.89 (m, 8H), 3.61–3.52 (m, 2H), 3.38–3.35 (m, 1H), 2.06–1.95 (m, 2H), 1.53–1.23 (m, 42H), 1.38 (s, 3H), 1.30 (s, 3H), 0.88–0.83 (m, 6H) |

TABLE I-continued

TABLE I-continued

| Comp. no. | Chemical structure | Rf value | MS | ¹H-NMR (CDCl₃) |
|---|---|---|---|---|
| 68 | (structure with $C_{22}H_{45}$, $C_2H_5$, OBn groups) | 0.19 (Hex:AcOEt = 3:1) | 1048 (M+) (FAB) | 7.40–7.18 (m, 20H), 6.28 (d, 1H, J=9.0 Hz), 4.97–4.85 (m, 2H), 4.83–4.78 (m, 2H), 4.73 (d, 1H, J=12 Hz), 4.64 (d, 1H, J=12 Hz), 4.57 (d, 1H, J=12 Hz), 4.46 (d, 1H, J=12 Hz), 4.36 (d, 1H, J=12 Hz), 4.12–3.88 (m, 7H), 3.82–3.77 (m, 1H), 3.60–3.48 (m, 2H), 3.40–3.32 (m, 1H), 2.08–1.92 (m, 2H), 1.48–1.12 (m, 42H), 1.39 (s, 3H), 1.30 (s, 3H), 0.93–0.82 (m, 6H) |
| 69 | (structure with $C_{21}H_{43}$, $C_6H_{13}$, OBn groups) | 0.35 (Hex:AcOEt = 3:1) | 1091 (M + H) (FAB) | 7.39–7.22 (m, 20H), 6.22 (d, 1H, J=8.4 Hz), 4.93–4.88 (m, 2H), 4.82–4.78 (m, 2H), 4.73 (d, 1H, J=12 Hz), 4.64 (d, 1H, J=12 Hz), 4.57 (d, 1H, J=12 Hz), 4.47 (d, 1H, J=12 Hz), 4.36 (d, 1H, J=12 Hz), 4.09–4.01 (m, 4H), 3.97 (t, 1H, J=6.1 Hz), 3.91–3.89 (m, 3H), 3.61–3.52 (m, 2H), 3.37 (dd, 1H, J=9.5, 5.6 Hz), 2.06–1.95 (m, 2H), 1.57–1.23 (m, 48H), 1.39 (s, 3H), 1.30 (s, 3H), 0.88–0.83 (m, 6H) |
| 70 | (structure with $C_{22}H_{45}$-n, $C_6H_{13}$-n, OBn groups) | 0.39 (Hex:AcOEt = 3:1) | 1104 (M+) (FAB) | 7.40–7.22 (m, 20H), 6.22 (d, 1H, J=8.5 Hz), 4.93–4.88 (m, 2H), 4.83–4.78 (m, 2H), 4.74 (d, 1H, J=12 Hz), 4.65 (d, 1H, J=12 Hz), 4.58 (d, 1H, J=12 Hz), 4.48 (d, 1H, J=12 Hz), 4.37 (d, 1H, J=12 Hz), 4.09–4.01 (m, 4H), 3.99–3.95 (m, 1H), 3.92–3.89 (m, 3H), 3.62–3.52 (m, 2H), 3.39–3.36 (m, 1H), 2.08–1.94 (m, 2H), 1.52–1.39 (m, 7H), 1.30–1.21 (m, 49H), 0.89–0.83 (m, 6H) |
| 71 | (structure with $C_{23}H_{47}$-n, CH₂CH₂Ph, OBn groups) | 0.19 (Hex:AcOEt = 5:1) | 1138 (M+) (FAB) | 7.38–7.09 (m, 25H), 6.27 (d, 1H, J=8.3 Hz), 4.92–4.86 (m, 2H), 4.81–4.76 (m, 2H), 4.72 (d, 1H, J=12 Hz), 4.63 (d, 1H, J=11 Hz), 4.55 (d, 1H, J=12 Hz), 4.38 (d, 1H, J=12 Hz), 4.28 (d, 1H, J=12 Hz), 4.09–4.07 (m, 3H), 4.02 (dd, 1H, J=10, 3.7 Hz), 3.94 (t, 1H, J=6.2 Hz), 3.89–3.85 (m, 3H), 3.60–3.58 (m, 1H), 3.51–3.47 (m, 1H), 3.33–3.29 (m, 1H), 2.85–2.75 (m, 1H), 2.63–2.53 (m, 1H), 2.05–1.88 (m, 2H), 1.86–1.74 (m, 1H), 1.65–1.55 (m, 1H), 1.50–1.43 (m, 5H), 1.30–1.20 (m, 43H), 0.87 (t, 3H, J=6.8 Hz) |

TABLE I-continued

| Comp. no. | Chemical structure | Rf value | MS | ¹H-NMR (CDCl₃) |
|---|---|---|---|---|
| 72 | (structure with C₂₃H₄₇-n acyl, cyclopentylmethyl, acetonide, OBn groups) | 0.20 (Hex:AcOEt = 4:1) | 1116 (M+) (FAB) | 7.42–7.23 (m, 20H), 6.19 (d, 1H, J=8.3 Hz), 4.92–4.89 (m, 2H), 4.80 (d, 1H, J=12 Hz), 4.79 (d, 1H, J=11 Hz), 4.73 (d, 1H, J=12 Hz), 4.64 (d, 1H, J=11 Hz), 4.56 (d, 1H, J=12 Hz), 4.49 (d, 1H, J=12 Hz), 4.36 (d, 1H, J=12 Hz), 4.13–3.89 (m, 8H), 3.62–3.60 (m, 1H), 3.54–3.50 (m,1H), 3.38–3.34 (m, 1H), 2.07–1.89 (m, 3H), 1.77–1.69 (m, 2H), 1.64–1.45 (m, 6H), 1.39 (s, 3H), 1.30 (s, 3H), 1.24–1.22 (m, 42H), 1.11–1.01 (m, 2H), 0.87 (t, 3H, J=6.8 Hz) |
| 73 | (structure with C₂₃H₄₇-n acyl, p-tolylmethyl, acetonide, OBn groups) | 0.42 (Hex:AcOEt = 3:1) | 1139 (M + H) (FAB) | 7.39–7.22 (m, 20H), 7.05 (d, 2H, J=7.8 Hz), 7.00 (d, 2H, J=8.0 Hz), 6.40 (d, 1H, J=8.4 Hz), 4.94–4.92 (m, 2H), 4.83–4.76 (m, 2H), 4.75–4.72 (m, 1H), 4.66 (d, 1H, J=11 Hz), 4.58 (d, 1H, J=11 Hz), 4.48 (d, 1H, J=12 Hz), 4.29–4.12 (m, 3H), 4.09–4.04 (m, 2H), 3.99–3.96 (m, 1H), 3.93–3.90 (m, 2H), 3.65 (d, 1H, J=11 Hz), 3.53 (d, 1H, J=6.8 Hz), 3.41–3.37 (m, 1H), 2.68 (d, 1H, J=7.4 Hz), 2.29 (s, 3H), 2.09–2.01 (m, 2H), 1.47–1.45 (m, 5H), 1.28–1.23 (m, 43H), 0.88 (t, 3H, J=6.8 Hz). |
| 74 | (structure with C₅H₁₁-n, Ph-propyl acyl, acetonide, OBn groups) | 0.79 (Hex:AcOEt = 1:1) | 887 (M + H) (ESI) | 7.37–7.12 (m, 25H), 6.35 (d, 1H, J=8.2 Hz), 4.92 (d, 1H, J=12 Hz), 4.80–4.75 (m, 3H), 4.72 (d, 1H, J=12 Hz), 4.62 (d, 1H, J=12 Hz), 4.57 (d, 1H, J=12 Hz), 4.45 (d, 1H, J=12 Hz), 4.35 (d, 1H, J=12 Hz), 4.09–3.98 (m, 4H), 3.92–3.84 (m, 4H), 3.56–3.51 (m, 2H), 3.37–3.32 (m, 1H), 2.88–2.83 (m, 2H), 2.35–2.28 (m, 2H), 1.45–1.37 (m, 5H), 1.29–1.15 (m, 9H), 0.85 (t, 3H, J=6.9 Hz) |
| 75 | (structure with C₅H₁₁-n, Ph-butyl acyl, acetonide, OBn groups) | 0.56 (Hex:AcOEt = 2:1) | 915 (M + H) (ESI) | 7.38–7.10 (m, 25H), 6.29 (d, 1H, J=8.4 Hz), 4.92–4.86 (m, 2H), 4.79–4.74 (m, 2H), 4.69 (d, 1H, J=12 Hz), 4.63 (d, 1H, J=11 Hz), 4.56 (d, 1H, J=12 Hz), 4.46 (d, 1H, J=12 Hz), 4.35 (d, 1H, J=12 Hz), 4.09–3.84 (m, 8H), 3.60–3.51 (m, 2H), 3.37–3.32 (m, 1H), 2.57–2.54 (m, 2H), 2.04–2.00 (m, 2H), 1.59–1.18 (m, 18H), 0.84 (t, 3H, J=6.9 Hz) |

TABLE I-continued

| Comp. no. | Chemical structure | Rf value | MS | $^1$H-NMR (CDCl$_3$) |
|---|---|---|---|---|
| 76 | (structure with C$_8$H$_{17}$-n phenoxy group, C$_5$H$_{11}$-n, acetonide, and tribenzyl sugar) | 0.32 (Hex:AcOEt = 1:1) | 1015 (M + H) (FAB) | 7.31-7.25(m, 20H), 7.22 (d, 2H, J=8.08z), 6.77 (d, 2H, J=8.0 Hz), 4.94 (d, 1H, J=11 Hz), 4.85-4.77 (m, 4H), 4.65-4.55 (m, 2H), 4.49-4.31 (m, 2H), 4.11-4.01 (m, 4H), 3.92-3.85 (m, 5H), 3.58-3.52 (m, 2H), 3.40-3.36 (m, 1H), 2.84-2.80 (m, 2H), 2.36-2.23 (m, 2H), 1.79-1.71 (m, 2H), 1.49-1.45 (m, 2H), 1.41 (s, 3H), 1.32 (s, 3H), 1.32-1.24 (m, 18␣), 0.90 (t, 6H, J=7.2 Hz). |
| 77 | (structure with C$_{16}$H$_{33}$-n phenoxy group, C$_5$H$_{11}$-n, acetonide, and tribenzyl sugar) | 0.32 (Hex:AcOEt = 1:1) | 1127 (M + H) (FAB) | 7.38-7.27 (m, 20H), 7.04 (d, 2H, J=8.5 Hz), 6.78 (d, 2H, J=8.5 Hz), 6.38 (d, 1H, J=7.7 Hz), 4.93 (d, 1H, J=12 Hz), 4.80-4.71 (m, 4H), 4.63 (d, 1H, J=11 Hz), 4.57 (d, 1H, J=12 Hz), 4.45 (d, 1H, J=12 Hz), 4.35 (d, 1H, 12 Hz), 4.10-4.00 (m, 4H), 3.96-3.85 (m, 6H), 3.57-3.53 (m, 3H), 3.37-3.35 (m, 1H), 2.81 (t, 2H, J=6.8 Hz), 2.34-2.27 (m, 2H), 1.74-1.70 (m, 2H), 1.44-1.39 (m, 2H), 1.39 (s, 3H), 1.30 (s, 3H), 1.36-1.20 (m, 34H), 0.89-0.84 (m, 6H). |
| 78 | (structure with C$_8$H$_{17}$-n-phenyl-C(O)NH-phenyl-(CH$_2$)$_4$- group, C$_5$H$_{11}$-n, acetonide, and tribenzyl sugar) | 0.25 (Hex:AcOEt = 7:1) | 1146 (M + H) (FAB) | 7.74 (d, 2H, J=8.0 Hz), 7.66 (s, 1H), 7.49 (d, 2H, J=8.2 Hz), 7.39-7.23 (m, 22H), 7.13 (d, 2H, J=8.3 Hz), 6.38 (d, 1H, J=8.4 Hz), 4.93-4.88 (m, 2H), 4.80-4.70 (m, 3H), 4.63 (d, 1H, J=11 Hz), 4.56 (d, 1H, J=11 Hz), 4.46(d, 1H, J=12 Hz), 4.36 (d, 1H, J=12 Hz), 4.13-4.00 (m, 4H), 3.97-3.86 (m, 3H), 3.61-3.54 (m, 2H), 3.40-3.37 (m, 1H), 2.66 (t, 2H, J=7.8 Hz), 2.58-2.54 (m, 2H), 2.06-2.01 (m, 2H), 1.66-1.60 (m, 4H), 1.46-1.40 (m, 2H), 1.40 (s, 3H), 1.31 (s, 3H), 1.32-1.21 (m, 20H), 0.90-0.84 (m, 6H). |

TABLE I-continued

| Comp. no. | Chemical structure | Rf value | MS | ¹H-NMR (CDCl₃) |
|---|---|---|---|---|
| 79 | (structure with C₁₈H₃₇-n) | 0.20 (Hex:AcOEt = 4:1) | 1139 (M + H) (FAB) | 7.38-7.20 (m, 20H), 6.37 (d, 1H, J=7.6 Hz), 4.92 (d, 1H, J=12 Hz), 4.87 (d, 1H, J=3.6 Hz), 4.77-4.71 (m, 3H), 4.63 (d, 1H, J=1 Hz), 4.56 (d, 1H, J=12 Hz), 4.45 (d, 1H, J=12 Hz), 4.35 (d, 1H, J=12 Hz), 4.15-3.93 (m, 5H), 3.9.-3.86 (m, 4H), 3.60-3.52 (m, 2H), 3.39-3.35 (m, 1H), 2.84 (t, 2␤, J=7.8 Hz), 2.53 (t, 2H, J=7.8 Hz), 2.34-2.28 (m, 2H), 1.46-1.39 (m, 2H), 1.39 (s, 3H), 1.30 (s, 3H), 1.30-1.25 (m, 40H), 0.89-0.85 (m, 6H). |
| 80 | (structure with C₁₉H₃₉-n) | 0.40 (Hex:AcOEt = 4:1) | 1124 (M + H) (FAB) | 7.66 (d, 2H, J=8.2 Hz), 7.40-7.27 (m, 20H), 7.20 (d, 2H, J=8.0 Hz), 7.03 (d, 1H, J=7.2 Hz), 4.97 (d, 1H, J=3.6 Hz), 4.92 (d, 1H, J=11 Hz), 4.82-4.77 (m, 2H), 4.70 (d, 1H, J=12 Hz), 4.67 (d, 1H, J=11 Hz), 4.57 (d, 1H, J=12 Hz), 4.39 (d, 1H, J=12 Hz), 4.37-4.30 (m, 2H), 4.29-4.21 (m, 2H), 4.11-4.01 (m, 2H), 4.00-3.85 (m, 3H), 3.73-3.69 (m, 1H), 3.59-3.55 (m, 1H), 3.41-3.37 (m, 1H), 2.63 (t, 2␤, J=7.6 Hz), 1.55-1.45 (m, 2H), 1.43 (s, 3H), 1.33 (s, 3H), 1.37-1.24 (m, 50H), 0.88 (t, 3H, J=6.8 Hz), 0.78 (t, 3H, J=6.8 Hz). |
| 81 | (structure with piperazine-C₁₄H₂₉-n) | 0.39 (CH₂Cl₂:MeOH = 10:1) | 1119 (M + H) (ESI) | 7.41-7.20 (m, 20H), 6.38-6.25 (m, 1H), 4.93-4.88 (m, 2H), 4.84-4.78 (m, 2H), 4.75 (d, 1H, J=12 Hz), 4.66 (d, 1H, J=12 Hz), 4.50 (d, 1H, J=12 Hz), 4.49 (d, 1H, J=12 Hz), 4.38 (d, 1H, J=12 Hz), 4.13-3.85 (m, 8H), 3.62-3.53 (m, 2H), 3.39-3.34 (m, 1H), 2.75-1.97 (m, 14H), 1.55-1.13 (m, 42H), 0.90-0.83 (m, 6H). |

TABLE I-continued

| Comp. no. | Chemical structure | Rf value | MS | $^1$H-NMR (CDCl$_3$) |
|---|---|---|---|---|
| 82 | 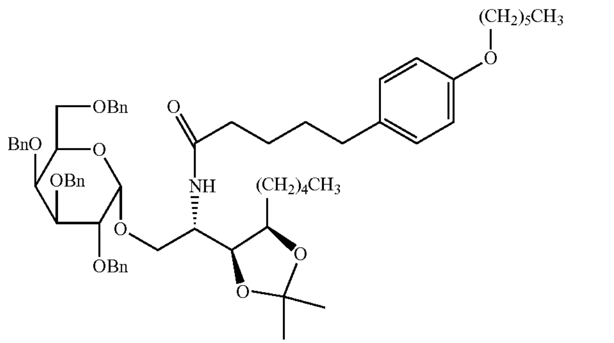 | 0.18 (Hex:AcOEt = 4:1) | 1015 (M + H) (FAB) | 7.39-7.23 (m, 20H), 7.04 (d, 2H, J=8.5 Hz), 6.78 (d, 2H, J=8.5 Hz), 6.33 (d, 1H, J=8.5 Hz), 4.93-4.88 (m, 2H), 4.79 (d, 1H, J=11 Hz), 4.77 (d, 1H, J=12 Hz), 4.71 (d, 1H, J=12 Hz), 4.63 (d, 1H, J=11 Hz), 4.57 (d, 1H, J=12 Hz), 4.47 (d, 1H, J=12 Hz), 4.36 (d, 1H, J=12 Hz), 4.10-4.01 (m, 3H), 3.96 (m, 1H), 3.92-3.86 (m, 4H), 3.61-3.53 (m, 2H), 3.37 (dd, 1H, J=9.3, 5.5 Hz), 2.53-2.50 (m, 1H), 2.08-1.97 (m, 2H), 1.74 (m, 2H), 1.64-1.51 (m, 6H), 1.47-1.38 (m, 4H), 1.40 (s, 3H), 1.36-1.17 (m, 10H), 1.31 (s, 3H), 0.91-0.88 (m, 3H), 0.87-0.83 (m, 3H) |
| 83 | 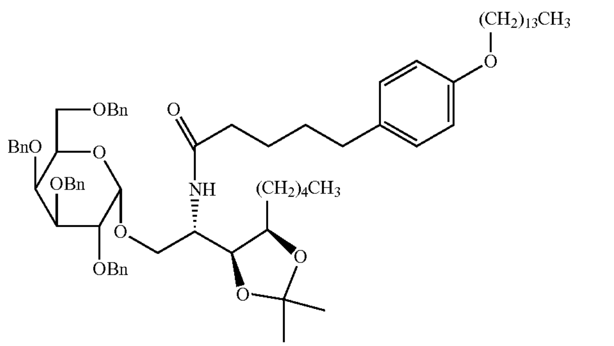 | 0.36 (Hex:AcOEt = 3:1) | 1127 (M + H) (FAB) | 7.39-7.23 (m, 20H), 7.03 (d, 2H, J=8.5 Hz), 6.78 (d, 2H, J=8.5 Hz), 6.32 (d, 1H, J=8.5 Hz), 4.93-4.88 (m, 2H), 4.79 (d, 1H, J=11 Hz), 4.77 (d, 1H, J=12 Hz), 4.71 (d, 1H, J=12 Hz), 4.63 (d, 1H, J=11 Hz), 4.57 (d, 1H, J=12 Hz), 4.47 (d, 1H, J=12 Hz), 4.36 (d, 1H, J=12 Hz), 4.11-4.01 (m, 3H), 3.97 (m, 1H), 3.92-3.86 (m, 4H), 3.61-3.53 (m, 2H), 3.37 (dd, 1H, J=9.4, 5.5 Hz), 2.53-2.50 (m, 2H), 2.07-1.98 (m, 2H), 1.74 (m, 2H), 1.64-1.51 (m, 6H), 1.47-1.38 (m, 4H), 1.40 (s, 3H), 1.36-1.17 (m, 26H), 1.31 (s, 3H), 0.90-0.83 (m, 6H) |
| 84 | 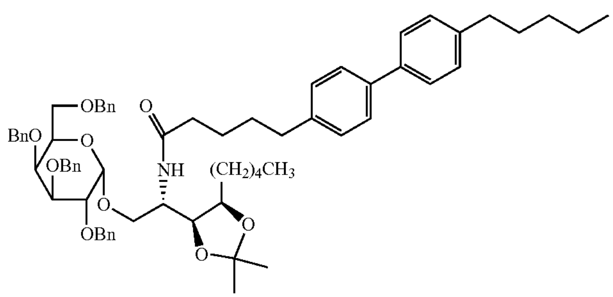 | 0.40 (Hex:AcOEt = 4:1) | 1061 (M + H) (FAB) | 7.48-7.45 (m, 4H), 7.38-7.19 (m, 24H), 6.35 (d, 1H, J=7.7 Hz), 4.91-4.88 (m, 2H), 4.78 (d, 1H, J=11 Hz), 4.76 (d, 1H, J=12 Hz), 4.69 (d, 1H, J=12 Hz), 4.62 (d, 1H, J=11 Hz), 4.54 (d, 1H, J=12 Hz), 4.47 (d, 1H, J=12 Hz), 4.36 (d, 1H, J=12 Hz), 4.11-3.86 (m, 8H), 3.62-3.53 (m, 2H), 3.36 (dd, 1H, J=9.4, 5.5 Hz), 2.64-2.60 (m, 4H), 2.10-1.98 (m, 2H), 1.68-1.53 (m, 8H), 1.50-1.16 (m, 10H), 1.40 (s, 3H), 1.31 (s, 3H), 0.90 (t, 3H, J=6.8 Hz), 0.84 (t, 3H, J=6.9 Hz) |

TABLE I-continued

| Comp. no. | Chemical structure | Rf value | MS | $^1$H-NMR (CDCl$_3$) |
|---|---|---|---|---|
| 85 | Structure with C$_{23}$H$_{47}$ acyl group, ceramide with OH, OH, C$_5$H$_{11}$, linked via CH$_2$O to sugar with OBn, OBn, OBn, BnO | 0.55 (CH$_2$Cl$_2$:MeOH = 20:1) | 1064 (M+) (FAB) | 7.39-7.27 (m, 20H), 6.38 (d, 1H, J=8.4 Hz), 4.93-4.84 (m, 4H), 4.77-4.76 (m, 1H), 4.68 (d, 1H, J=12 Hz), 4.57 (d, 1H, J=11 Hz), 4.48 (d, 1H, J=12 Hz), 4.39 (d, 1H, J=12 Hz), 4.22-4.19 (m, 1H), 4.05 (dd, 1H, J=10, 3.8 Hz), 3.97 (m, 1H), 3.89-3.85 (m, 4H), 3.80 (d, 1H, J=8.3 Hz), 3.52-3.44 (m, 3H), 2.14-2.10 (m, 2H), 1.56-1.26 (m, 50H), 0.90-0.87 (m, 6H) |
| 86 | Structure with C$_{22}$H$_{45}$ acyl group, ceramide with OH, OH, C$_5$H$_{11}$, linked via CH$_2$O to sugar with OBn, OBn, OBn, BnO | 0.18 (Hex:AcOEt = 2:1) | 1051 (M + H) (FAB) | 7.37-7.26 (m, 20H), 6.37 (d, 1H, J=8.4 Hz), 4.93-4.84 (m, 3H), 4.80-4.73 (m, 2H), 4.68 (d, 1H, J=12 Hz), 4.57 (d, 1H, J=11 Hz), 4.48 (d, 1H, J=12 Hz), 4.39 (d, 1H, J=12 Hz), 4.22-4.18 (m, 1H), 4.05 (dd, 1H, J=10, 3.8 Hz), 3.97-3.77 (m, 6H), 3.53-3.43 (m, 5H), 2.14-2.09 (m, 2H), 1.63-1.13 (m, 46H), 0.88 (t, 6H, J=6.8 Hz) |
| 87 | Structure with C$_{21}$H$_{43}$ acyl group, ceramide with OH, OH, C$_5$H$_{11}$, linked via CH$_2$O to sugar with OBn, OBn, OBn, BnO | 0.18 (Hex:AcOEt = 2:1) | 1036 (M+) (FAB) | 7.39-7.26 (m, 20H), 6.37 (d, 1H, J=8.3 Hz), 4.94-4.83 (m, 3H), 4.81-4.72 (m, 2H), 4.68 (d, 1H, J=12 Hz), 4.57 (d, 1H, J=11 Hz), 4.48 (d, 1H, J=12 Hz), 4.39 (d, 1H, J=12 Hz), 4.22-4.18 (m, 1H), 4.05 (dd, 1H, J=10, 3.8 Hz), 3.97 (brs, 1H), 3.90-3.82 (m, 4H), 3.80 (d, 1H, J=8.3 Hz), 3.53-3.43 (m, 5H), 2.14-2.10 (m, 2H), 1.60-1.20 (m, 44H), 0.89 (t, 6S, J=6.9 Hz) |
| 88 | Structure with C$_{22}$H$_{45}$ acyl group, ceramide with OH, OH, C$_4$H$_9$, linked via CH$_2$O to sugar with OBn, OBn, OBn, BnO | 0.50 (CH$_2$Cl$_2$:MeOH = 20:1) | 1036 (M+) (FAB) | 7.35-7.25 (m, 20H), 6.36 (d, 1H, J=8.0 Hz), 4.92-4.83 (m, 3H), 4.75-4.74 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.20-4.18 (m, 1H), 4.03 (dd, 1H, J=10, 3.7 Hz), 3.95 (brs, 1H), 3.87-3.83 (m, 4H), 3.77 (d, 1H, J=8.4 Hz), 3.50-3.45 (m, 4H), 2.12-2.08 (m, 3H), 1.53-1.24 (m, 46H), 0.89-0.85 (m, 6H) |

TABLE I-continued

| Comp. no. | Chemical structure | Rf value | MS | ¹H-NMR (CDCl₃) |
|---|---|---|---|---|
| 89 | [structure with $C_{21}H_{43}$, $C_3H_7$, OBn groups] | 0.37 (CH₂Cl₂:MeOH = 20:1) | 1008 (M+) (FAB) | 7.37-7.25 (m, 20H), 6.36 (d, 1H, J=8.3 Hz), 4.92-4.83 (m, 3H), 4.78-4.71 (m, 2H), 4.65 (d, 1H, J=12 Hz), 4.55 (d, 1H, J=11 Hz), 4.46 (d, 1H, J=12 Hz), 4.37 (d, 1H, J=12 Hz), 4.20-4.17 (m, 1H), 4.03 (dd, 1H, J=10, 3.7 Hz), 3.95 (brs, 1H), 3.91-3.83 (m, 4H), 3.77 (d, 1H, J=8.4 Hz), 3.50-3.42 (m, 4H), 2.12-2.07 (m, 3H), 1.53-1.24 (m, 42H), 0.90-0.85 (m, 6H) |
| 90 | [structure with $C_{22}H_{45}$, $C_2H_5$, OBn groups] | 0.31 (Hex:AcOEt = 1:1) | 1008 (M+) (FAB) | 7.40-7.20 (m, 20H), 6.37 (d, 1H, J=8.5 Hz), 4.93-4.80 (m, 3H), 4.75 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.20 (m, 1H), 4.03 (dd, 1H, J=10, 3.8 Hz), 3.95 (brs, 1H), 3.91-3.81 (m, 4H), 3.75 (d, 1H, J=8.5 Hz), 3.52-3.37 (m, 4H), 2.13-2.02 (m, 3H), 1.42-1.15 (m, 42H), 0.92 (t, 3H, J=7.5 Hz), 0.87 (t, 3H, J=7.3 Hz) |
| 91 | [structure with $C_{21}H_{43}$, $C_6H_{13}$, OBn groups] | 0.54 (CH₂Cl₂:MeOH = 20:1) | 1050 (M+) (FAB) | 7.27-7.25 (m, 20H), 6.35 (d, 1H, J=8.4 Hz), 4.92-4.83 (m, 3H), 4.75 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.20-4.17 (m, 1H), 4.03 (dd, 1H, J=10, 3.8 Hz), 3.95 (brs, 1H), 3.87-3.83 (m, 4H), 3.77 (d, 1H, J=8.4 Hz), 3.50-3.45 (m, 4H), 2.12-2.06 (m, 3H), 1.56-1.24 (m, 48H), 0.88-0.85 (m, 6H) |
| 92 | [structure with $C_{22}H_{45}$, $C_6H_{13}$-n, OBn groups] | 0.31 (CH₂Cl₂:MeOH = 20:1) | 1063 (M − H) (FAB) | 7.38-7.23 (m, 20H), 6.36 (d, 1H, J=8.4 Hz), 4.92-4.83 (m, 3H), 4.79-4.70 (m, 2H), 4.67 (d, 1H, J=12 Hz), 4.56 (d, 1H, J=11 Hz), 4.47 (d, 1H, J=12 Hz), 4.38 (d, 1H, J=12 Hz), 4.21-4.18 (m, 1H), 4.03 (dd, 1H, J=10, 3.8 Hz), 3.96 (d, 1H, J=1.9 Hz), 3.88-3.83 (m, 4H), 3.78 (d, 1H, J=8.3 Hz), 3.51-3.44 (m, 4H), 2.14-2.08 (m, 3H), 1.63-1.19 (m, 50H), 0.89-0.85 (m, 6H) |

TABLE I-continued

| Comp. no. | Chemical structure | Rf value | MS | $^1$H-NMR (CDCl$_3$) |
|---|---|---|---|---|
| 93 | [Structure: sugar with OBn groups (BnO, OBn, OBn) linked via O to a chain with NH-C(=O)-C$_{23}$H$_{47}$, OH, OH, and terminal -CH$_2$CH$_2$-Ph] | 0.12 (Hex:AcOEt = 2:1) | 1098 (M+) (FAB) | 7.37-7.22 (m, 22H), 7.16-7.13 (m, 3H), 6.32 (d, 1H, J=8.4 Hz), 4.90 (d, 1H, J=11 Hz), 4.87-4.81 (m, 2H), 4.75-4.73 (m, 1H), 4.64 (d, 1H, J=12 Hz), 4.56 (d, 1H, J=11 Hz), 4.45 (d, 1H, J=12 Hz), 4.36 (d, 1H, J=12 Hz), 4.20-4.17 (m, 1H), 4.03 (dd, 1H, J=10, 3.8 Hz), 3.94-3.93 (m, 1H), 3.90-3.81 (m, 4H), 3.72 (d, 1H, J=7.8 Hz), 3.53-3.42 (m, 4H), 2.80-2.76 (m, 1H), 2.61-2.57 (m, 1H), 2.25 (brs, 1H), 2.08 (t, 2H, J=7.6 Hz), 1.92-1.87(m, 1H), 1.69-1.64 (m, 1H), 1.31-1.20(m, 42H), 0.87 (t, 3H, J=6.8 Hz) |
| 94 | [Structure: sugar with OBn groups linked via O to a chain with NH-C(=O)-C$_{23}$H$_{47}$, OH, OH, and terminal cyclopentyl group] | 0.25 (CH$_2$Cl$_2$:MeOH = 20:1) | 1076 (M+) (FAB) | 7.37-7.25 (m, 20H), 6.35 (d, 1H, 3=8.3 Hz), 4.92-4.83 (m, 3H), 4.78-4.71 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.19-4.16 (m, 1H), 4.03 (dd, 1H, J=10, 3.8 Hz), 3.95 (m, 1H), 3.84-3.82 (m, 3H), 3.78 (d, 1H, J=8.5 Hz), 3.57-3.42 (m, 4H), 3.50 (d, 1H, J=6.4 Hz), 2.14-2.08 (m, 3H), 1.93-1.87 (m, 1H), 1.78-1.69 (m, 2H), 1.61-1.42 (m, 6H), 1.34-0.92 (m, 44H), 0.87 (t, 3H, J=6.8 Hz) |
| 95 | [Structure: sugar with OBn groups linked via O to a chain with NH-C(=O)-C$_{23}$H$_{47}$, OH, OH, and terminal -CH$_2$CH$_2$-(p-tolyl) with CH$_3$] | 0.10 (CH$_2$Cl$_2$:MeOH = 20:1) | 1099 (M + H) (FAB) | 7.36-7.26 (m, 20H), 7.09 (d, 2H, J=7.4 Hz), 7.04 (d, 2H, J=8.0 Hz), 6.45 (d, 1H, J=7.8 Hz), 4.92-4.88 (m, 2H), 4.85-4.83 (m, 2H), 4.73 (d, 2H, J=3.7 Hz), 4.68 (d, 1H, J=7.6 Hz), 4.56 (d, 1H, J=11 Hz), 4.46 (d, 1H, J=7.6 Hz), 4.36 (d, 1H, J=7.7 Hz), 4.05-4.02 (m, 1H), 3.94-3.84 (m, 5H), 3.69-3.65 (m, 1H), 3.51-3.48 (m, 3H), 2.31 (s, 3H), 2.10-2.08 (m, 2H), 1.47-1.45 (m, 2H), 1.33-1.22 (m, 40H), 0.88 (t, 3H, J=7.6 Hz). |
| 96 | [Structure: sugar with OBn groups linked via O to a chain with NH-C(=O)-CH$_2$CH$_2$-Ph, OH, OH, and terminal n-hexyl chain] | 0.42 (Hex:AcOEt = 1:1) | 847 (M + H) (ESI) | 7.37-7.14 (m, 25H), 6.35 (d, 1H, J=8.1 Hz), 4.89 (d, 1H, J=11 Hz), 4.86 (d, 1H, J=12 Hz), 4.79 (d, 1H, J=3.7 Hz), 4.74-4.73 (m, 2H), 4.65 (d, 1H, J=12 Hz), 4.55 (d, 1H, J=11 Hz), 4.45 (d, 1H, J=12 Hz), 4.36 (d, 1H, J=12 Hz), 4.16-4.14 (m, 1H), 4.01 (dd, 1H, J=10, 3.8 Hz), 3.91-3.71 (m, 6H), 3.51-3.38 (m, 4H), 2.90 (t, 2H, J=7.4 Hz), 2.40 (t, 2H, J=7.3 Hz), 2.09 (t, 1H, J=5.4 Hz), 1.55-1.20 (m, 8H), 0.87 (t, 3H, J=7.0 Hz) |

TABLE I-continued

| Comp. no. | Chemical structure | Rf value | MS | $^1$H-NMR (CDCl$_3$) |
|---|---|---|---|---|
| 97 | 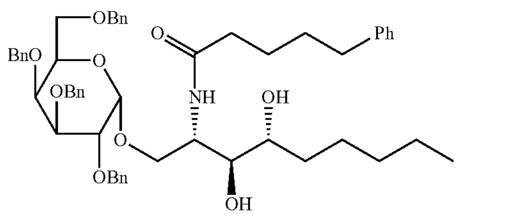 | 0.13 (Hex:AcOEt = 2:1) | 875 (M + H) (ESI) | 7.37-7.11 (m, 25H), 6.39 (d, 1H, J=8.3 Hz), 4.92-4.81 (m, 3H), 4.74-4.71 (m, 2H), 4.66 (d, 1H, J=12 Hz), 4.55 (d, 1H, J=11 Hz), 4.45 (d, 1H, J=12 Hz), 4.36 (d, 1H, J=12 Hz), 4.20-4.16 (m, 1H), 4.03 (dd, 1H, J=10, 3.8 Hz), 3.92-3.76 (m, 6H), 3.50-3.42 (m, 4H), 2.58 (t, 2H, J=6.9 Hz), 2.14-2.08 (m, 2H), 1.62-1.20 (m, 12H), 0.87 (t, 3H, J=6.9 Hz) |
| 98 | 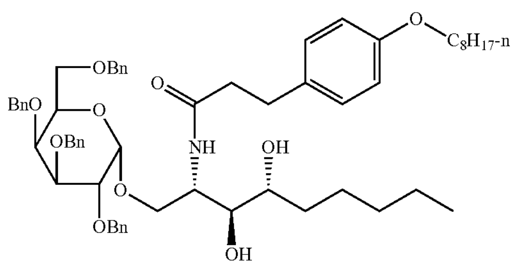 | 0.46 (Hex:AcOEt = 1:1) | 975 (M + H) (ESI) | 7.37-7.23 (m, 20H), 7.06 (d, 2H, J=8.4 Hz), 6.79 (d, 2H, J=8.4 Hz), 6.37 (d, 1H, J=8.1 Hz), 4.92 (d, 1H, J=11 Hz), 4.85 (d, 1H, J=12 Hz), 4.80 (d, 1H, J=3.7 Hz), 4.75 (s, 2H), 4.66 (d, 1H, J=11 Hz), 4.55 (d, 1H, 11 Hz), 4.45 (d, 1H, J=11 Hz), 4.36 (d, 1H, J=11 Hz), 4.18-4.16 (m, 1H), 4.02 (dd, 1H, J=10, 3.7 Hz), 3.93-3.81 (m, 6H), 3.74 (d, 1H, J=8.3 Hz), 3.70 (s, 1H), 3.50-3.40 (m, 4H), 2.86-2.83 (m, 2H), 2.40-2.37 (m, 2H), 2.10 (d, 1H, J=5.5 Hz), 1.44-1.42 (m, 2H), 1.33-1.26 (m, 18H), 0.88 (t, 6H, J=6.8 Hz). |
| 99 | 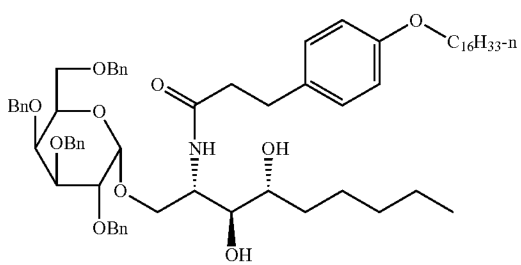 | 0.67 (Hex:AcOEt = 1:1) | 1087 (M + H) (FAB) | 7.35-7.27 (m, 20H), 7.04 (d, 2H, J=8.4 Hz), 6.79 (d, 2H, J=8.4 Hz), 6.37 (d, 1H, J=8.4 Hz), 4.90 (d, 1H, J=11 Hz), 4.86 (d, 1H, J=12 Hz), 4.80 (d, 1H, J=3.9 Hz), 4.75 (s, 2H), 4.64 (d, 1H, J=11 Hz), 4.55 (d, 1H, J=12 Hz), 4.46 (d, 1H, J=11 Hz), 4.36 (d, 1H, J=12 Hz), 4.17-4.16 (m, 1H), 4.01 (dd, 1H, J=9.8, 3.7 Hz), 3.94-3.80 (m, 7H), 3.74 (d, 1H, J=8.3 Hz), 3.50-3.40 (m, 4H), 2.85-2.82 (m, 2H), 2.40-2.37 (m, 2H), 2.11 (d, 1H, J=5.4 Hz), 1.75-1.72 (m, 2H), 1.45-1.42 (m, 2H), 1.36-1.24 (m, 34H), 0.88-0.86 (m, 6H). |
| 100 | 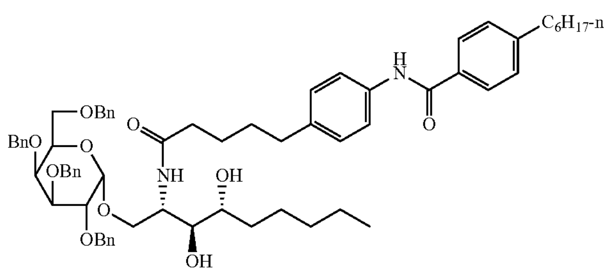 | 0.48 (CH$_2$Cl$_2$:MeOH = 10:1) | 1105 (M + H) (FAB) | 7.75 (d, 2H, J=8.2 Hz), 7.70 (s, 1H), 7.50 (d, 2H, J=8.4 Hz), 7.35-7.26 (m, 22H), 7.14 (d, 2H, J=8.4 Hz), 6.37 (d, 1H, J=7.8 Hz), 4.91-4.83 (m, 3H), 4.76-4.73 (m, 2H), 4.66 (d, 2H, J=12 Hz), 4.55 (d, 1H, J=11 Hz), 4.46 (d, 1H, J=11 Hz), 4.36 (d, 1H, J=12 Hz), 4.25-4.19 (m, 2H), 4.07-4.02 (m, 1H), 3.96-3.80 (m, 5H), 3.51-3.48 (m, 4H), 2.65 (t, 2H, J=7.6 Hz), 2.59-2.56 (m, 2H), 2.16-2.10 (m, 2H), 1.66-1.59 (m, 4H), 1.32-1.27 (m, 22H), 0.90-0.86 (m, 6H). |

TABLE I-continued

| Comp. no. | Chemical structure | Rf value | MS | ¹H-NMR (CDCl₃) |
|---|---|---|---|---|
| 101 | (structure with C₁₈H₃₇-n phenyl propanoyl group attached to amide-linked sphingosine-like core bearing OH, OH, and tri-OBn sugar ether) | 0.24 (CH₂Cl₂:MeOH = 10:1) | 1098 (M + H) (FAB) | 7.37-7.29(m, 20H), 6.37 (d, 1H, J=8.2 Hz), 4.92-4.89 (m, 2H), 4.88-4.75 (m, 3H), 4.75-4.73 (m, 2H), 4.68 (d, 1H, J=12 Hz), 4.54 (d, 1H, J=12 Hz), 4.45 (d, 1H, J=12 Hz), 4.36 (d, 1H, J=12 Hz), 4.14-3.86 (m, 8H), 3.60-3.52 (m, 2H), 3.39-3.35 (m, 1H), 2.88-2.82 (m, 2H), 2.58-2.52 (m, 2H), 2.36-2.26 (m, 2H), 1.55-1.52 (m, 2H), 1.29-1.21(m, 40H), 0.91-0.82 (m, 6H). |
| 102 | (structure with C₁₉H₃₉-n phenyl benzoyl group attached to amide-linked sphingosine-like core bearing OH, OH, and tri-OBn sugar ether) | 0.49 (CH₂Cl₂:MeOH = 15:1) | 1084 (M + H) (FAB) | 7.66 (d, 2H, J=8.0 Hz), 7.38-7.26 (m, 20H), 7.21 (d, 2H, J=8.0 Hz), 7.00(d, 1H, J=7.2 Hz), 4.95 (d, 1H, J=3.6 Hz), 4.92 (d, 1H, J=12 Hz), 4.82-4.77 (m, 2H), 4.72 (d, 1H, J=12 Hz), 4.65 (d, 1H, J=12 Hz), 4.57 (d, 1H, J=12 Hz), 4.42 (d, 1H, J=12 Hz), 4.37-4.30 (m, 1H), 4.29-4.20 (m, 2H), 4.12-4.01 (m, 2H), 4.00-3.85 (m, 2H), 3.73-3.69 (m, 1H), 3.62-3.58 (m, 1H), 3.41-3.38 (m, 1H), 2.63 (t, 28, J=7.6 Hz) 1.52-1.47 (m, 2H), 1.37-1.24 (m, 50 H), 0.88-0.82 (m, 6H). |
| 103 | (structure with N-C₁₄H₂₉-n piperazinyl propanoyl group attached to amide-linked sphingosine-like core bearing OH, OH, and tri-OBn sugar ether) | 0.41 (CH₂Cl₂:MeOH = 10:1) | 1079 (M + H) (ESI) | 7.38-7.24 (m, 20H), 6.40 (d, 1H, J=8.4 Hz), 4.93-4.83 (m, 3H), 4.77-4.75 (m, 2H), 4.68 (d, 1H, J=12 Hz), 4.57 (d, 1H, J=12 Hz), 4.47 (d, 1H, J=12 Hz), 4.37 (d, 1H, J=12 Hz), 4.23-4.18 (m, 1H), 4.04 (dd, 1H, J=10, 3.7 Hz), 3.98-3.95 (m, 1H), 3.90-3.84 (m, 4H), 3.52-3.42 (m, 4H), 2.60-2.11 (m, 14H), 1.70-1.15 (m, 36H), 0.90-0.85 (m, 6H). |

TABLE I-continued

| Comp. no. | Chemical structure | Rf value | MS | $^1$H-NMR (CDCl$_3$) |
|---|---|---|---|---|
| 104 | 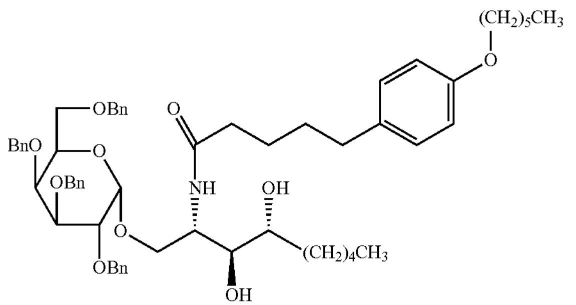 | 0.45 (CH$_2$Cl$_2$:MeOH = 20:1) | 975 (M + H) (FAB) | 7.38-7.24 (m, 20H), 7.04 (d, 2H, J=8.6 Hz) 6.79 (d, 2H, J=8.6 Hz), 6.39 (d, 1H, J=8.4 Hz), 4.92-4.83 (m, 3H), 4.73 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.21-4.18 (m, 1H), 4.03 (dd, 1H, J=10, 3.8 Hz), 3.93-3.77 (m, 7H), 3.53-3.42 (m, 3H), 2.52 (m, 2H), 2.17-2.10 (m, 2H), 1.75 (m, 2H), 1.66-1.51 (m, 6H), 1.50-1.40 (m, 2H), 1.38-1.22 (m, 12H), 0.91-0.86 (m, 6H) |
| 105 | 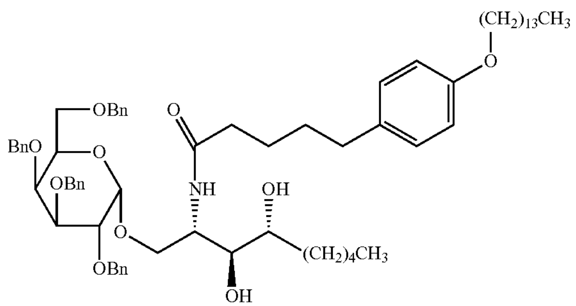 | 0.38 (CH$_2$Cl$_2$:MeOH = 20:1) | 1086 (M + H) (FAB) | 7.38-7.24 (m, 20H), 7.04 (d, 2H, J=8.6 Hz) 6.79 (d, 2H, J=8.6 Hz), 6.39 (d, 1H, J=8.4 Hz), 4.91 (d, 1H, J=11 Hz), 4.87 (d, 1H, J=12 Hz), 4.84 (d, 1H, J=3.8 Hz), 4.73 (m, 2H), 4.66 (d, 1H, J=12 Hz), 4.55 (d, 1H, J=11 Hz), 4.46 (d, 1H, J=12 Hz), 4.37 (d, 1H, J=12 Hz), 4.21-4.18 (m, 1H), 4.03 (dd, 1H, J=10, 3.8 Hz), 3.93-3.78 (m, 7H), 3.53-3.42 (m, 3H), 2.52 (m, 2H), 2.15-2.10 (m, 2H), 1.74 (m, 2H), 1.67-1.51 (m, 6H), 1.50-1.38 (m, 2H), 1.37-1.23 (m, 28H), 0.88 (m, 6H) |
| 106 | 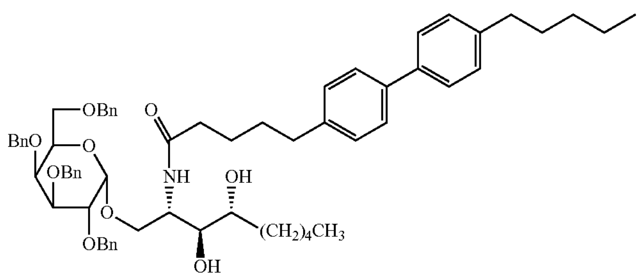 | 0.43 (CH$_2$Cl$_2$:MeOH = 20:1) | 1020 (M+) (FAB) | 7.47 (dd, 4H, J=8.2, 2.9 Hz) 7.35-7.19 (m, 24H), 6.42 (d, 1H, J=8.4 Hz), 4.89 (d, 1H, J=11 Hz), 4.87 (d, 1H, J=12 Hz), 4.84 (d, 1H, J=3.8 Hz), 4.72 (m, 2H), 4.66 (d, 1H, J=12 Hz), 4.53 (d, 1H, J=11 Hz), 4.46 (d, 1H, J=12 Hz), 4.37 (d, 1H, J=12 Hz), 4.21-4.18 (m, 1H), 4.03 (dd, 1H, J=10, 3.8 Hz), 3.92-3.79 (m, 7H), 3.53-3.43 (m, 3H), 2.63 (m, 4H), 2.17-2.11 (m, 3H), 1.63-1.54 (m, 8H), 1.53-1.44 (m, 2H), 1.38-1.25 (m, 8H), 0.92-0.86 (m, 6H) |

TABLE I-continued

| Comp. no. | Chemical structure | Rf value | MS | $^1$H-NMR (CDCl$_3$) |
|---|---|---|---|---|
| 107 | C$_{23}$H$_{47}$ acyl, C$_5$H$_{11}$ chain, sugar-linked ceramide | 0.40 (CH$_2$Cl$_2$:MeOH = 5:1) | 704 (M+) (FAB) | 4.91 (brs, 1H), 4.14 (m, 1H), 3.97 (m, 1H), 3.79-3.76 (m, 7H), 3.64-3.63 (m, 2H), 3.52 (m, 1H), 2.14 (t, 2H, J=7.4 Hz), 1.61-1.13 (m, 50 H), 0.84-0.79 (m, 6H) |
| 108 | C$_{22}$H$_{45}$ acyl, C$_5$H$_{11}$ chain, sugar-linked ceramide | 0.51 (CHCl$_3$:MeOH = 4:1) | 690 (M+) (FAB) | 4.91 (d, 1H, J=3.1 Hz), 4.23-4.15 (m, 1H), 3.95-3.85 (m, 2H), 3.81-3.63 (m, 6H), 3.59-3.51 (m, 2H), 2.21 (t, 2H, J=7.5 Hz), 1.61-1.25 (m, 48H), 0.90-0.85 (m, 6H) |
| 109 | C$_{21}$H$_{43}$ acyl, C$_5$H$_{11}$ chain, sugar-linked ceramide | 0.47 (CH$_2$Cl$_2$:MeOH = 5:1) | 676 (M+) (FAB) | 4.90 (d, 1H, J=3.0 Hz), 4.27-4.20 (m, 1H), 3.96-3.92 (m, 1H), 3.91 (dd, 1H, J=11, 4.0 Hz), 3.82-3.65 (m, 6H), 3.58-3.51 (m, 2H), 2.22 (t, 2H, J=7.6 Hz), 1.70-1.21 (m, 46H), 0.90-0.85 (m, 6H) |
| 110 | C$_{22}$H$_{45}$ acyl, C$_4$H$_9$ chain, sugar-linked ceramide | 0.20 (CH$_2$Cl$_2$:MeOH = 7:1) | 676 (M+) (FAB) | 4.84 (d, 1H, J=3.1 Hz), 4.12-4.11 (m, 1H), 3.89 (m, 1H), 3.82 (dd, 1H, J=11, 4.5 Hz), 3.74-3.59 (m, 6H), 3.50 (m, 1H), 3.31-3.30 (m, 1H), 2.16 (t, 2H, J=7.7 Hz), 1.59-1.12 (m, 46H), 0.85-0.78 (m, 6H) |

TABLE I-continued

| Comp. no. | Chemical structure | Rf value | MS | ¹H-NMR (CDCl₃) |
|---|---|---|---|---|
| 111 | C₂₁H₄₃ acyl, C₃H₇ side chain sphingoid glycoside | 0.24 (CH₂Cl₂:MeOH = 5:1) | 648 (M+H) (FAB) | 4.20 (d, 1H, J=3.1 Hz), 4.20-4.19 (m, 1H), 3.97 (m, 1H), 3.82 (dd, 1H, J=11, 4.5 Hz), 3.74-3.59 (m, 6H), 3.50 (m, 1H), 3.31-3.30 (m, 1H), 2.16 (t, 2H, J=7.7 Hz), 1.61-1.20 (m, 42H), 0.93 (t, 3H, J=6.9 Hz), 0.88 (t, 3H, J=6.8 Hz) |
| 112 | C₂₂H₄₅ acyl, C₂H₅ side chain sphingoid glycoside | 0.35 (CH₂Cl₂:MeOH = 5:1) | 648 (M+H) (FAB) | (Pyridine-d5) 8.42 (d, 1H, J=8.9 Hz), 5.56 (d, 1H, J=3.8 Hz), 5.24 (m, 1H), 4.70-4.59 (m, 2H), 4.54 (m, 1H), 4.49 (m, 1H), 4.39 (m, 4H), 4.30-4.23 (m, 1H), 4.22-4.15 (m, 1H), 2.42 (t, 2H, J=7.5 Hz), 2.32-2.18 (m, 1H), 1.89-1.71 (m, 3H), 1.39-1.15 (m, 38H), 1.21 (t, 3H, J=7.3 Hz), 0.85 (t, 3H, J=6.8 Hz) |
| 113 | C₂₁H₄₃ acyl, C₆H₁₃ side chain sphingoid glycoside | 0.26 (CH₂Cl₂:MeOH = 5:1) | 690 (M+) (FAB) | 4.91 (d, 1H, J=3.6 Hz), 4.22-4.21 (m, 1H), 3.93-3.88 (m, 2H), 3.83-3.67 (m, 6H), 3.56-3.55 (m, 2H), 3.39-3.35 (m, 1H), 2.22 (t, 2H, J=7.6 Hz), 1.68-1.19 (m, 48H), 0.90-0.87 (m, 6H) |
| 114 | C₂₂H₄₅ acyl, C₆H₁₃₋ₙ side chain sphingoid glycoside | 0.05 (CH₂Cl₂:MeOH = 10:1) | 704 (M+) (ESI) | 4.91 (d, 1H, J=3.7 Hz), 4.23-4.20 (m, 1H), 3.95-3.87 (m, 2H), 3.82-3.66 (m, 6H), 3.56-3.51 (m, 2H), 2.21 (t, 2H, J=7.7 Hz), 1.70-1.24 (m, 50H), 0.90-0.86 (m, 6H) |

TABLE I-continued

| Comp. no. | Chemical structure | Rf value | MS | ¹H-NMR (CDCl₃) |
|---|---|---|---|---|
| 115 | (structure) | 0.08 (CH₂Cl₂:MeOH = 10:1) | 738 (M+) (ESI) | 7.45-7.14 (m, 5H), 4.89 (d, 1H, J=3.6 Hz), 4.25-4.22 (m, 1H), 3.91-3.85 (m, 2H), 3.81-3.62 (m, 6H), 3.60-3.50 (m, 2H), 2.95-2.85 (m, 1H), 2.73-2.62 (m, 1H), 2.17 (t, 2H, J=7.7 Hz), 2.07-1.95 (m, 1H), 1.72-1.53 (m, 3H), 1.33-1.18 (m, 40H), 0.88 (t, 3H, J=6.5 Hz) |
| 116 | (structure) | 0.36 (CH₂Cl₂:MeOH = 5:1) | 717 (M+H) (FAB) | 4.78 (d, 1H, J=3.8 Hz), 4.08-4.05 (m, 1H), 3.83-3.81 (m, 1H), 3.78-3.74 (dd, 1H, J=11, 4.8 Hz), 3.72-3.46 (m, 8H), 3.40-3.37 (m, 1H), 2.07 (t, 2H, J=7.7 Hz), 1.94-1.84 (m, 1H), 1.71-1.59 (m, 2H), 1.51-1.42 (m, 6H), 1.19-0.86 (m, 44H), 0.75 (t, 3H, J=6.8 Hz) |
| 117 | (structure) | 0.30 (CH₂Cl₂:MeOH = 5:1) | 738 (M+) (ESI) | 6.87 (d, 2H, J=7.9 Hz), 6.82 (d, 2H, J=7.8 Hz), 4.64 (d, 1H, J=4.0 Hz), 4.25-4.22 (m, 1H), 3.92-3.86 (m, 2H), 3.67-3.65 (m, 2H), 3.52-3.43 (m, 7H), 3.40-3.36 (m, 2H), 3.10-3.08 (s, 3H), 2.80-2.78 (m, 1H), 2.35-2.32 (m, 1H), 2.04 (s, 3H), 1.96 (t, 2H, J=7.6 Hz), 1.35-1.32 (m, 2H), 1.06-1.00 (m, 40H), 0.62 (t, 3H, J=6.8 Hz). |
| 118 | (structure) | 0.24 (CH₂Cl₂:MeOH = 5:1) | 486 (M+H) (ESI) | 7.30-7.17 (m, 5H), 4.88 (d, 1H, J=3.7 Hz), 4.21-4.19 (m, 1H), 3.92-3.62 (m, 8H), 3.50-3.46 (m, 2H), 2.94 (t, 2H, J=7.8 Hz), 2.53 (t, 2H, J=7.8 Hz), 1.66-1.28 (m, 8H), 0.90 (t, 3H, J=6.6 Hz) |

TABLE I-continued

| Comp. no. | Chemical structure | Rf value | MS | ¹H-NMR (CDCl₃) |
|---|---|---|---|---|
| 119 | 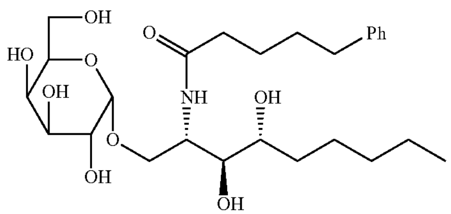 | 0.19 (CH₂Cl₂:MeOH = 7:1) | 514 (M + H) (ESI) | 7.30-7.16 (m, 5H), 4.90 (d, 1H, J=3.7 Hz), 4.21-4.19 (m, 1H), 3.92-3.64 (m, 8H), 3.58-3.48 (m, 2H), 2.68-2.57 (m, 2H), 2.28-2.17 (m, 2H), 1.72-1.19 (m, 12H), 0.89 (t, 3H, J=6.5 Hz) |
| 120 | 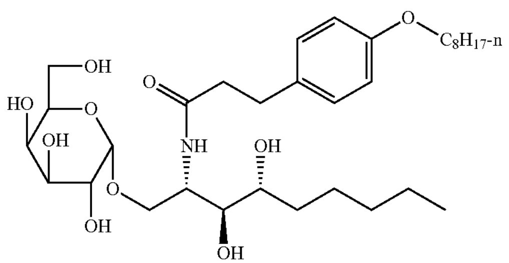 | 0.42 (AcOEt:MeOH = 10:1) | 614 (M + H) (ESI) | 7.12 (d, 2H, J=8.3 Hz), 6.82 (d, 2H, J=8.4 Hz), 4.89 (d, 1H, J=3.6 Hz), 4.22-4.20 (m, 1H), 3.96-3.92 (m, 3H), 3.87-3.63 (m, 6H), 3.51-3.48 (m, 2H), 3.39-3.35 (m, 3H), 2.88 (t, 2H, J=7.6 Hz), 2.49 (t, 2H, J=7.6 Hz), 1.80-1.73 (m, 2H), 1.54-1.45 (m, 2H), 1.38-1.31 (m, 18H), 0.89 (t, 6H, J=6.8 Hz). |
| 121 | 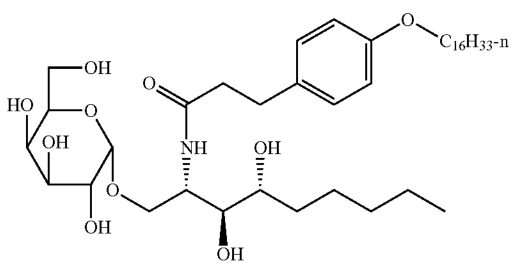 | 0.07 (CH₂Cl₂:MeOH = 10:1) | 725 (M + H) (ESI) | 7.11 (d, 2H, J=8.5 Hz), 6.83 (d, 2H, J=8.5 Hz), 4.90 (d, 1H, J=3.7 Hz), 4.21-4.18 (m, 1H), 3.94-3.89 (m, 3H), 3.86-3.81 (m, 1H), 3.80-3.62 (m, 6H), 3.50-3.46 (m, 2H), 3.40-3.35 (m,3H), 2.90-2.85 (m, 2H), 2.56-2.51 (m, 2H), 1.80-1.76 (m, 2H), 1.50-1.42 (m, 2H), 1.34-1.26 (m, 34H), 0.92-0.87 (m, 6H). |
| 122 | 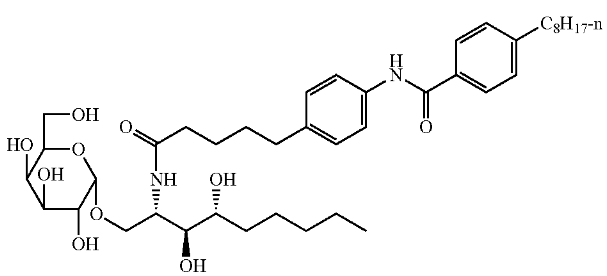 | 0.03 (Hex:AcOEt = 1:1) | 745 (M + H) (FAB) | 7.83 (d, 2H, J=8.4 Hz), 7.72 (s, 1H), 7.54 (d, 2H, J=8.4 Hz), 7.30 (d, 2H, J=7.6 Hz), 7.18 (d, 2H, J=8.0 Hz), 4.87 (d, 1H, J=4.0 Hz), 4.23-4.20 (m, 1H), 3.95-3.92 (m, 3H), 3.83-3.64 (m, 6H), 3.52-3.46 (m, 2H), 3.39-3.35 (m, 3H), 2.71-2.64 (m, 4H), 2.45-2.42 (m, 2H), 1.74-1.68 (m, 6H), 1.48-1.29 (m, 22H), 0.95-0.86 (m, 6H). |

TABLE I-continued

| Comp. no. | Chemical structure | Rf value | MS | ¹H-NMR (CDCl₃) |
|---|---|---|---|---|
| 123 | (structure with C₁₈H₃₇-n phenyl group) | 0.07 (CH₂Cl₂:MeOH = 10:1) | 738 (M + H) (FAB) | 7.12-7.08 (m, 4H), 4.89(d, 1H, J=3.7 Hz) 4.34-4.21 (m, 1H), 3.93 (d, 1H, J=3.6 Hz), 3.89-3.63 (m, 7H), 3.48-3.44 (m, 2H), 2.90 (t, 2H, J=8.0 Hz), 2.58-2.49 (m, 6H), 1.71-1.58 (m, 4H), 1.40-1.23 (m, 36H), 0.90-0.87 (m, 6H). |
| 124 | (structure with C₁₉H₃₉-n phenyl group) | 0.27 (CH₂Cl₂:MeOH = 5:1) | 724 (M + H) (FAB) | 7.73 (d, 2H, J=7.2 Hz), 7.27 (d, 2H, J=7.6 Hz), 4.97 (d, 1H, J=3.3 Hz), 4.48-4.44 (m, 1H), 4.05-3.99 (m, 1H), 3.95-3.90 (m, 1H), 3.80-3.58 (m, 8H), 2.65 (t, 3H, J=7.3 Hz), 1.72-1.54 (m, 4H), 1.43-1.23 (m, 38H), 0.97-0.86 (m, 6H). |
| 125 | (structure with C₁₄H₂₉-n piperazine group) | 0.10 (CH₂Cl₂:MeOH = 5:1) | 719 (M + H) (ESI) | 4.90 (d, 1H, J=3.6 Hz), 4.22-4.17 (m, 1H), 3.93-3.88 (m, 2H), 3.81-3.65 (m, 6H), 3.53-3.51 (m, 2H), 2.80-2.23 (m, 14H), 1.69-1.48 (m, 36H), 0.90-0.86 (m, 6H). |

TABLE I-continued

| Comp. no. | Chemical structure | Rf value | MS | ¹H-NMR (CDCl₃) |
|---|---|---|---|---|
| 126 | 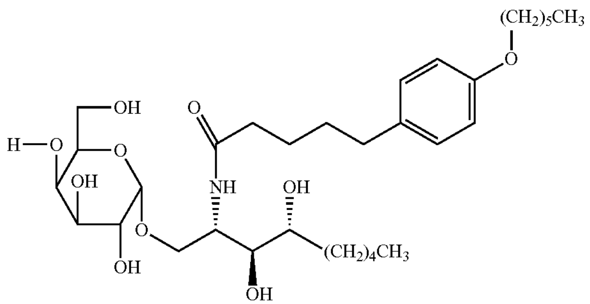 | 0.33 (CH₂Cl₂:MeOH = 5:1) | 614 (M + H) (FAB) | 7.08 (d, 2H, J=8.6 Hz), 6.82 (d, 2H, J=8.6 Hz), 4.91 (d, 1H, J=3.7 Hz), 4.22-4.18 (m, 1H), 3.94 (m, 2H), 3.92-3.67 (m, 7H), 3.57-3.52 (m, 2H), 2.58 (m, 2H), 2.24 (m, 2H), 1.77 (m, 2H), 1.73-1.26 (m, 20H), 0.93-0.88 (m, 6H) |
| 127 | 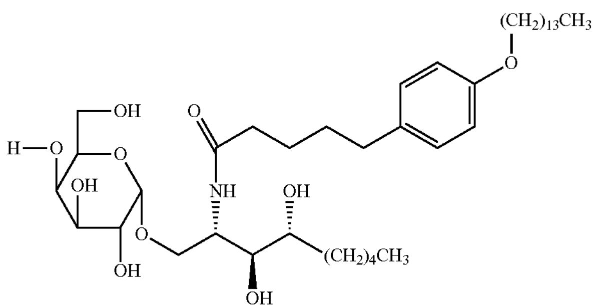 | 0.58 (CH₂Cl₂:MeOH = 5:1) | 727 (M + H) (FAB) | 7.07 (d, 2H, J=8.6 Hz), 6.81 (d, 2H, J=8.6 Hz), 4.91 (brs, 1H), 4.19-4.13 (m, 1H), 3.96-3.64 (m, 9H), 3.57-3.52 (m, 2H), 2.57 (m, 2H), 2.24 (m, 2H), 1.76 (m, 2H), 1.68-1.22 (m, 36H), 0.91-0.86 (m, 6H) |

TABLE I-continued

| Comp. no. | Chemical structure | Rf value | MS | ¹H-NMR (CDCl₃) |
|---|---|---|---|---|
| 128 | (structure with biphenyl-pentyl chain, amide, (CH₂)₄CH₃, triol sugar) | 0.36 (CH₂Cl₂:MeOH = 5:1) | 660 (M + H) (ESI) | (CDCl₃:CD₃OD = 4:1) 7.53-7.48 (m, 4H), 7.25-7.23 (m, 4H), 4.91 (d, 1H, J=3.4 Hz), 4.23-4.20 (m, 1H), 3.93-3.67 (m, 9H), 3.56-3.51 (m, 2H), 2.72-2.62 (m, 4H), 2.27 (m, 2H), 1.73-1.53 (m, 8H), 1.86-1.26 (m, 10H), 0.93-0.87 (m, 6H) |
| 129 | (structure with C₂₃H₄₇-n acyl, C₅H₁₁-n chain, H2O, sugar) | 0.11 (CH₂Cl₂:MeOH = 10:1) | 704 (M+) (ESI) | 4.92-4.90 (m, 1H), 4.24-4.17 (m, 1H), 3.97-3.87 (m, 2H), 3.83-3.65 (m, 6H), 3.58-3.50 (m, 2H), 2.21 (t, 2H, J=7.4 Hz), 1.75-1.15 (m, 50H), 0.97-0.84 (m, 6H) |

Test of Production of Cytokines by Glycolipid Derivative (in vitro)

Splenocytes were prepared from the spleens of C57BL/6 mice (6 to 8 weeks old, female) and suspended in a RPMI1640 medium (purchased by Nakarai) containing 10% fetal bovine serum (purchased by GIBCO), $5 \times 10^{-5}$ M 2-mercaptoethanol (purchased by GIBCO), 1 mM pyruvate (purchased by SIGMA), and 25 mM HEPE (purchased by SIGMA). These were seeded on a 96-well flat bottom plate (purchased by IWAKI) in an amount of $5 \times 10e5$ cells/well and a glycolipid derivative was added to each at a final concentration of 100 ng/ml. The results were cultured at 37° C. in the presence of 5% $CO_2$ for 72 hours, then the culture supernatent was collected. The concentration of the IL-4 and IFN-γ in the culture supernatent were measured by ELISA (BD Pharmingen EIA Kit) (Table 2).

TABLE 2

| Compound no. | IL-4 (pg/ml) | IFN-γ (pg/ml) |
| --- | --- | --- |
| 110 | 226 | 10614 |
| 111 | 256 | 7413 |
| 112 | 237 | 5832 |
| 113 | 251 | 7967 |
| 114 | 225 | 8067 |
| 115 | 137 | 2481 |
| 116 | 226 | 5268 |
| 117 | 181 | 5485 |
| 127 | 159 | 2506 |
| 129 | 232 | 7179 |
| α-Galcer | 201 | 21900 |
| control | 10 | 18 |

As a result, in the case of α-GalCer, as previously reported, it was confirmed that IFN-γ was produced remarkably dominantly. On the other hand, it was learned that the compounds of the present invention had weaker IFN-γ producing activities compared with α-GalCer and caused IL-4 to be predominantly produced.

INDUSTRIAL APPLICABILITY

According to the present invention, by chemically synthesizing glycolipid derivatives, where the substituent of the Sphingosine base part is a short chain carbon alkyl group, substituted or unsubstituted cycloalkyl group, substituted or unsubstituted aryl group, or substituted or unsubstituted aralkyl group, these can be mass produced economically and efficiently. Drugs containing these as active ingredients for the treatment of diseases where the Th1/Th2 immune balance is shifted toward the Th1 bias or diseases where the Th1 cells cause the symptoms to worsen or Th2 type cytokine producing derivatives are provided. Further, intermediates useful for the production of these compounds are also provided.

The invention claimed is:

1. A method for preparing a glycolipid derivative comprising:

reacting a compound having a formula (II):

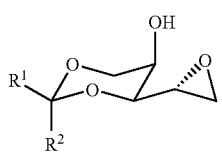

(II)

wherein $R^1$ and $R^2$ independently indicate a hydrogen atom; $C_1$ to $C_4$ alkyl group which may be substituted with a substituent selected from the group consisting of halogen atom, methoxy group, ethoxy group and nitro group; $C_6$ to $C_{12}$ aryl group which may be substituted with a substituent selected from the group consisting of fluorine atom, chlorine atom, bromine atom, methoxy group, nitro group, cyano group and trifluoromethyl group, or $R^1$ and $R^2$ bond together to indicate a propylene group, butylene group, pentylene group or hexylene group, whereby a cyclic structure is formed, with any one of alkyl metal reagents having the formulae, (IIIa), (IIIb), (IIIc), (IIId):

  (IIIa)

  (IIIb)

  (IIIc)

  (IIId)

where $R^3$ indicates a $C_1$ to $C_7$ linear alkyl group which may be substituted at a branch point with a substituent selected from the group consisting of methyl group, ethyl group, propyl group, butyl group, pentyl group, hexyl group, heptyl group, cyclopentyl group, cyclohexyl group, isobutyl group, cycloheptyl group, isopentyl group and isohexyl group; $C_3$ to $C_8$ cycloalkyl group which may be substituted with a substituent selected from the group consisting of methyl group, ethyl group, propyl group, butyl group, methoxy group, chlorine atom, fluorine atom and trifluoromethyl group; $C_6$ to $C_{18}$ aryl group which may be substituted with a substituent selected from the group consisting of methyl group, ethyl group, methoxy group, fluorine atom, chlorine atom, phenyl group, 2-fluorophenyl group, phenoxy group, phenylmethyl group, cyclopentyl group, cyclopentoxy group, trifluoromethyl group, acylamino group, cyano group, cycloheptyl group and cycloheptyloxy group; or $C_7$ to $C_{18}$ aralkyl group which may be substituted with a substituent selected from the group consisting of fluorine atom, chlorine atom, methyl group, ethyl group, methoxy group, trifluoromethyl group, cyclopentyl group and cycloheptyloxy group, M indicates Li, MgCl, MgBr or MgI, and X indicates a chlorine atom, bromine atom, iodine atom or fluorine atom to obtain a compound having the formula (IV):

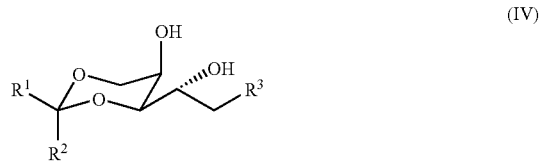

(IV)

where $R^1$, $R^2$ and $R^3$ are as defined above, reacting the compound having the formula (IV) with an alkylsulfonyl halide, arylsulfonyl halide, aralkylsulfonyl halide, alkylsulfonic acid anhydride, arylsulfonic acid anhydride or aralkylsulfonic acid anhydride to obtain a compound having the formula (V):

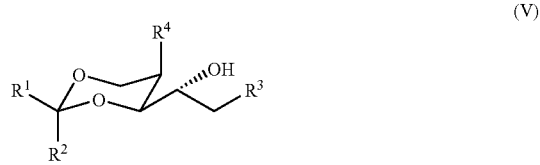

(V)

where $R^1$, $R^2$ and $R^3$ are the same as defined above and $R^4$ indicates an alkylsulfonyloxy group, arylsulfonyloxy group or aralkylsulfonyloxy group, reacting the compound having the formula (V) with an azidation agent to obtain a compound having the formula (VIa):

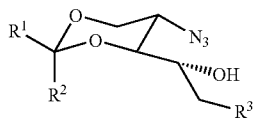
(VIa)

where $R^1$, $R^2$ and $R^3$ are the same as defined above, removing the protective acetal group of the compound having the formula (VIa) to obtain a compound having the formula (VII), or removing the protective acetal group of the compound having the formula (V) to obtain a compound having the formula (VIb):

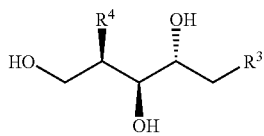
(VIb)

where $R^3$ and $R^4$ are the same as defined above, subsequently reacting the compound having the formula (VIb) with an azidation agent to obtain a compound having the formula (VII):

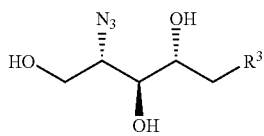
(VII)

where $R^3$ is as defined above, again acetalizing the compound having the formula (VII) to obtain a compound having the formula (VIIIa):

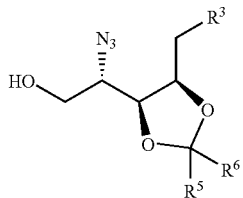
(VIIIa)

where $R^3$ is the same as defined above, $R^5$ and $R^6$ independently indicate a hydrogen atom; a $C_1$ to $C_5$ alkyl group which may be substituted by a substituent selected from the group consisting of fluorine atom and methoxy group; a $C_6$ to $C_{12}$ aryl group selected from the group consisting of phenyl group, p-tolyl group, m-tolyl group and naphtyl group; a $C_7$ to $C_{12}$ aralkyl group which may be substituted by a substituent selected from the group consisting of methyl group, ethyl group, fluorine atom and methoxy group, or $R^5$ and $R^6$ bond together to indicate a propylene group, butylene group or pentylene group, whereby a cyclic structure is formed, or protecting the two secondary hydroxy groups of the compound having the formula (VII) to obtain a compound having the formula (VIIIb)

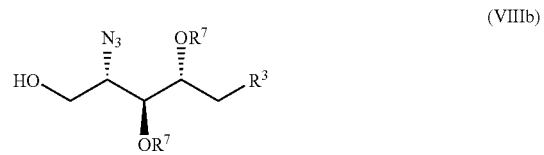
(VIIIb)

where, $R^3$ is the same as defined above and $R^7$ indicates a benzyl group, p-methoxybenzyl group, 3,4-dimethoxybenzyl group, p-nitrobenzyl group, diphenylmethyl group or di(p-nitrophenyl)methyl group, reacting the compound having the above formula (VIIIa) or (VIIIb) with a compound having the formula (IX) in the presence of boron trifluoride or tetra-n-butylammonium halide:

(IX)

where $R^7$ and X are the same as defined above to obtain a compound having the formula (Xa) or (Xb):

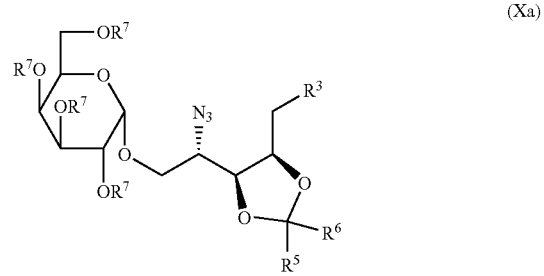
(Xa)

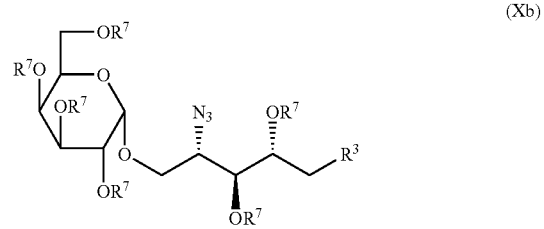
(Xb)

where $R^3$, $R^5$, $R^6$ and $R^7$ are the same as defined above, reducing the azide group of the compound having the formula (Xa) or (Xb) to an amino group to obtain a compound having the formula (XIa) or (XIb):

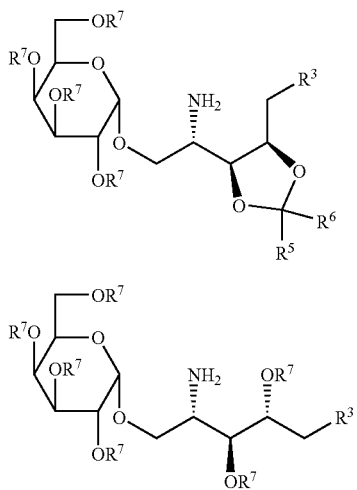

(XIa)

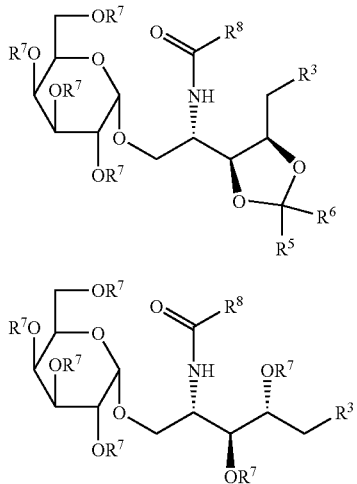

(XIb)

where $R^3$, $R^5$, $R^6$ and $R^7$ are the same as defined above,
acylating the amino group of the compound having the formula (XIa) or (XIb) to obtain a compound having the formula (XIIa) or (XIIb):

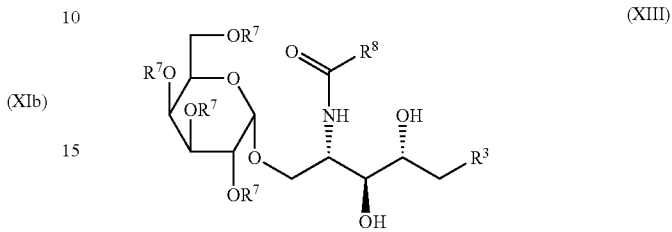

(XIIa)

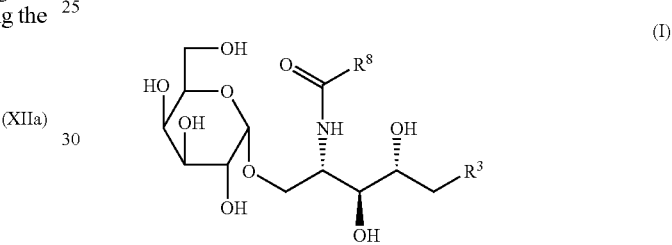

(XIIb)

where $R^3$, $R^5$, $R^6$ and $R^7$ are the same as defined above and $R^8$ indicates —$(CH_2)_m$—$CH_3$, where m is an integer of 10 to 25, a $C_6$ to $C_{35}$ aryl group which may be substituted with a substituent selected from the group consisting of alkyl group, alkoxy group and amide group, or a $C_7$ to $C_{35}$ aralkyl group which may be substituted with a substituent selected from the group consisting of alkyl group, alkoxy group and amide group,
removing the protective acetal of the compound having the formula (XIIa) to obtain the compound having the formula (XIII):

(XIII)

where $R^3$, $R^7$ and $R^8$ are the same as defined above, and
removing the remaining protective groups of the compound having the above formula (XIIb) or (XIII) to obtain a compound having the formula (I):

(I)

where $R^3$ and $R^8$ are the same as defined above.

2. A method for preparing a glycolipid derivative as claimed in claim 1, wherein $R^3$ in the formula (I), (IIIa), (IIIb), (IIIc), (IIId), (IV), (V), (VIa), (VIb), (VII), (VIIIa), (VIIIb), (Xa), (Xb), (XIa), (XIb), (XIIa), (XIIb) and (XIII) indicates $c_1$-$c_5$ linear alkyl, which may be substituted.

3. A method for preparing a glycolipid derivative as claimed in claim 1, wherein $R^3$ in the formula (I), (IIIa), (IIIb), (IIIc), (IIId), (IV), (V), (VIa), (VIb), (VII), (VIIIa), (VIIIb), (Xa), (Xb), (XIa), (XIb), (XIIa), (XIIb) and (XIII) indicates $c_4$ linear alkyl, which may be substituted.

4. A method for preparing a glycolipid derivative as claimed in claim 1, wherein the step of reacting the compound having the formula (VIIIa) or (VIIIb) with the compound having the formula (IX) is performed in the presence of tetra-n-butylammonium bromide.

* * * * *